United States Patent
Feige et al.

(10) Patent No.: US 11,358,998 B2
(45) Date of Patent: Jun. 14, 2022

(54) CRETION-COMPETENT MUTEINS OF THE HUMAN IL-27 ALPHA-SUBUNIT

(71) Applicant: TECHNISCHE UNIVERSITAET MUENCHEN, Munich (DE)

(72) Inventors: Matthias Feige, Munich (DE); Stephanie Mueller, Munich (DE)

(73) Assignee: TECHNISCHE UNIVERSITAET MUENCHEN, Munich (DE)

( * ) Notice: Subject to any disclaimer, the term of this patent is extended or adjusted under 35 U.S.C. 154(b) by 61 days.

(21) Appl. No.: 16/609,726

(22) PCT Filed: May 4, 2018

(86) PCT No.: PCT/EP2018/061561
§ 371 (c)(1),
(2) Date: Oct. 30, 2019

(87) PCT Pub. No.: WO2018/202876
PCT Pub. Date: Nov. 8, 2018

(65) Prior Publication Data
US 2020/0062817 A1    Feb. 27, 2020

(30) Foreign Application Priority Data
May 4, 2017   (EP) .................................. 17169358

(51) Int. Cl.
*A61K 38/20*    (2006.01)
*C07K 14/54*    (2006.01)
*A61P 37/06*    (2006.01)
*A61K 38/00*    (2006.01)

(52) U.S. Cl.
CPC .............. *C07K 14/54* (2013.01); *A61P 37/06* (2018.01); *A61K 38/00* (2013.01)

(58) Field of Classification Search
CPC ................................ C07K 14/54; A61K 38/00
See application file for complete search history.

(56) References Cited

U.S. PATENT DOCUMENTS

2015/0087602 A1* 3/2015 von Maltzahn ....... A23L 33/175
514/21.2

FOREIGN PATENT DOCUMENTS

JP            2006249033 A        9/2006

OTHER PUBLICATIONS

International Search Report dated Jul. 19, 2018 in PCT/EP2018/061561 (5 pages).
Written Opinion dated Jul. 19, 2018 in PCT/EP2018/061561 (5 pages).
Pflanz et al., "IL-27, a heterodimeric cytokine composed of EBI3 and p28 protein, induces proliferation of naive CD4+T cells", Immunity. Jun. 2002;16(6):779-90.
Shimozato et al., "The secreted form of p28 subunit of interleukin (IL)-27 inhibits biological functions of IL-27 and suppresses anti-allogeneic immune responses", Immunology. Sep. 2009;128(1 Suppl):e816-25. doi: 10.1111/i.1365-2567.2009.03088.x. Epub Mar. 23, 2009.
Stumhofer et al., "A role for IL-27p28 as an antagonist of gp130-mediated signaling", Nat Immunol. Dec. 2010;11 (12):1119-26. doi: 10.1038/ni.1957. Epub Nov. 7, 2010.
Altschul et al., Gapped BLAST and PSI-BLAST: a new generation of protein database search programs. Nucl. Acids Res.1997;25: 3389-3402.
Anelli et al., Thiol-mediated protein retention in the endoplasmic reticulum: the role of ERp44. EMBO J. Oct. 1, 2003;22(19):5015-5022.
Awasthi et al., A dominant function for interleukin 27 in generating interleukin 10-producing anti-inflammatory T cells. Nat Immunol. Dec. 2007;8(12):1380-1389.
Batten et al., Interleukin 27 limits autoimmune encephalomyelitis by suppressing the development of interleukin 17-producing T cells. Nat Immunol. Sep. 2006;7(9):929-936.
Behnke et al., Members of the Hsp70 Family Recognize Distinct Types of Sequences to Execute ER Quality Control. Mol Cell. Sep. 1, 2016;63(5):739-752.
Braakman and Hebert, Analysis of Disulfide Bond Formation. Curr Protoc Protein Sci. May 2001;Chapter 14: Unit14.1.
Case et al., AMBER 14: Reference Manual. Univ CA, San Francisco Technical Report Mar. 2014:825 pages.
Crabe et al., The IL-27 p28 subunit binds cytokine-like factor 1 to form a cytokine regulating NK and T cell activities requiring IL-6R for signaling. J Immunol. Dec. 15, 2009;183(12):7692-7702.
Devergne et al., Expression of Epstein-Barr Virus-Induced Gene 3, an Interleukin-12 p40-Related Molecule, throughout Human Pregnancy: Involvement of Syncytiotrophoblasts and Extravillous Trophoblasts. Am J Pathol. Nov. 2001;159(5):1763-1776.
Dietrich et al., A Soluble Form of IL-27Ra Is a Natural IL-27 Antagonist. J Immunol. Jun. 1, 2014;192(11):5382-5389.

(Continued)

*Primary Examiner* — Dong Jiang
(74) *Attorney, Agent, or Firm* — Acuity Law Group, PC; Michael A. Whittaker

(57) ABSTRACT

The present invention refers to a secretion-competent mutein of the α-subunit of human Interleukin 27 and to a human heterodimeric Interleukin 27. The present invention further refers to a nucleic acid molecule comprising a nucleotide sequence encoding a secretion-competent mutein of the α-subunit of human Interleukin 27 or the human heterodimeric Interleukin 27, to a host cell containing a nucleic acid molecule comprising a nucleotide sequence encoding a secretion-competent mutein of the α-subunit of human Interleukin 27 or of the human heterodimeric Interleukin 27. The invention also refers to an immune modulator comprising a secretion-competent mutein of the α-subunit of human Interleukin 27 or of the human heterodimeric Interleukin 27, to the respective use thereof as well as to a method of producing said secretion-competent muteins and to a secretion-incompetent mutein of the α-subunit of mouse Interleukin 27 and a secretion-competent mutein of the β-subunit of mouse Interleukin 27.

14 Claims, 27 Drawing Sheets

Figure 2:
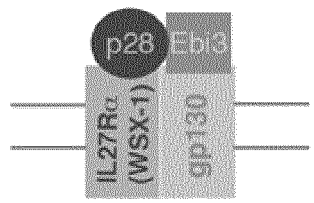
Figure 2:
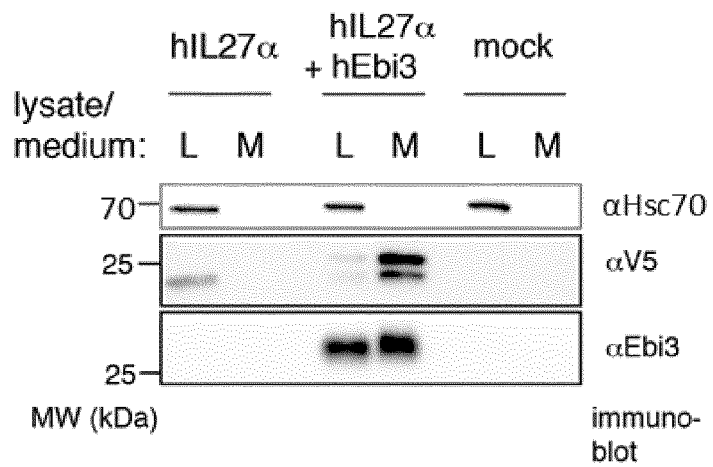
Figure 2:
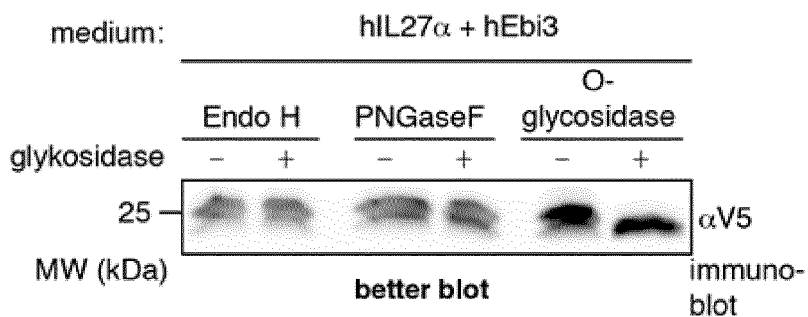
Figure 2:
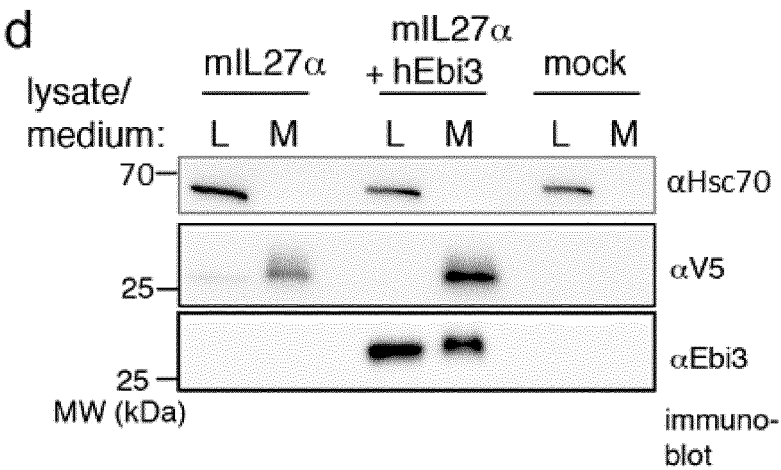

Specification includes a Sequence Listing.

(56) References Cited

OTHER PUBLICATIONS

Duitman et al., How a Cytokine Is Chaperoned through the Secretory Pathway by Complexing with Its Own Receptor: Lessons from Interleukin-15 (IL-15)/IL-15 Receptor α. Mol Cell Biol. Aug. 2008;28(15):4851-4861.
Elson et al., CLF associates with CLC to form a functional heteromeric ligand for the CNTF receptor complex. Nat Neurosci. Sep. 2000;3(9):867-872.
Feige et al., Dimerization-dependent Folding Underlies Assembly Control of the Clonotypic αβT Cell Receptor Chains. J Biol Chem. Oct. 30, 2015;290(44):26821-26831.
Fitzgerald et al., Suppression of autoimmune inflammation of the central nervous system by interleukin 10 secreted by interleukin 27-stimulated T cells. Nat Immunol. Dec. 2007;8(12):1372-1379.
Flynn et al., Peptide-binding specificity of the molecular chaperone BiP. Nature. Oct. 24, 1991;353(6346):726-730.
Garbers et al., An Interleukin-6 Receptor-dependent Molecular Switch Mediates Signal Transduction of the IL-27 Cytokine Subunit p28 (IL-30) via a gp130 Protein Receptor Homodimer. J Biol Chem. Feb. 8, 2013;288(6):4346-54.
Gubler et al., Coexpression of two distinct genes is required to generate secreted bioactive cytotoxic lymphocyte maturation factor. Proc Natl Acad Sci USA. May 15, 1991;88(10):4143-4147.
Hendershot et al., In Vivo Expression of Mammalian BiP ATPase Mutants Causes Disruption of the Endoplasmic Reticulum. Mol Biol Cell. Mar. 1995;6(3):283-296.
Hendershot et al., Inhibition of immunoglobulin folding and secretion by dominant negative BiP ATPase mutants. Proc Natl Acad Sci USA. May 28, 1996,93(11):5269-5274.
Jorgensen et al., Comparison of Simple Potential Functions for Simulating Liquid Water. J Chem Phys. 1983;79 (2):926-935.
Langrish et al., IL-12 and IL-23: master regulators of innate and adaptive immunity. Immunol Rev. Dec. 2004;202:96-105.
Lund et al., The choice of phorbol 12-myristate 13-acetate differentiation protocol influences the response of THP-1 macrophages to a pro-inflammatory stimulus. J Immunol Methods. Mar. 2016;430:64-70.
Lupardus and Garcia, The structure of interleukin-23 reveals the molecular basis of p40 subunit sharing with interleukin-12. J Mol Biol. Oct. 17, 2008;382(4):931-941.
Maier et al., ff14SB: Improving the Accuracy of Protein Side Chain and Backbone Parameters from ff99SB. J Chem Theory Comput. Aug. 11, 2015;11(8):3696-3713.
Oppmann et al., Novel p19 Protein Engages IL-12p40 to Form a Cytokine, IL-23, with Biological Activities Similar as Well as Distinct from IL-12. Immunity. Nov. 2000;13(5):715-725.

Patel and Kuchroo, Th17 Cell Pathway in Human Immunity: Lessons from Genetics and Therapeutic Interventions. Immunity. Dec. 15, 2015;43(6):1040-1051.
Petes et al., Interleukin (IL)-6 Inhibits IL-27- and IL-30-Mediated Inflammatory Responses in Human Monocytes. Front Immunol. Feb. 15, 2018;9:256.
Pflanz et al., WSX-1 and glycoprotein 130 constitute a signal-transducing receptor for IL-27. J Immunol. Feb. 15, 2004;172(4):2225-2231.
Reitberger et al., Assembly-induced folding regulates interleukin 12 biogenesis and secretion. J Biol Chem. May 12, 2017;292(19):8073-8081.
Scheller et al., No inhibition of IL-27 signaling by soluble gp130. Biochem Biophys Res Commun. Jan. 28, 2005;326 (4):724-728.
Sievers et al., Fast, scalable generation of high-quality protein multiple sequence alignments using Clustal Omega. Mol Syst Biol. Oct. 11, 2011;7:539.
Stumhofer et al., Interleukin 27 negatively regulates the development of interleukin 17-producing T helper cells during chronic inflammation of the central nervous system. Nat Immunol. Sep. 2006;7(9):937-945.
Stumhofer et al., Interleukins 27 and 6 induce STAT3-mediated T cell production of interleukin 10. Nat Immunol. Dec. 2007;8(12):1363-1371.
Tormo et al., A Polyglutamic Acid Motif Confers IL-27 Hydroxyapatite and Bone-Binding Properties. J Immunol. Mar. 15, 2013;190(6):2931-2937.
Vignali and Kuchroo, IL-12 Family Cytokines: Immunological Playmakers. Nat Immunol. Jul. 19, 2012;13 (8):722-728.
Wang et al., A novel IL-23p19/Ebi3 (IL-39) cytokine mediates inflammation in Lupus-like mice. Eur J Immunol. Jun. 2016;46(6):1343-1350.
Wirtz et al., Protection from lethal septic peritonits by neutralizing the biological function of interleukin 27. J Exp Med. Aug. 7, 2006;203(8):1875-1881.
Yan et al., Interleukin-30 (IL-27p28) alleviates experimental sepsis by modulating cytokine profile in NKT cells. J Hepatol. May 2016;64(5):1128-1136.
Yoon et al., Charged residues dominate a unique interlocking topography in the heterodimeric cytokine interleukin-12. EMBO J. Jul. 17, 2000;19(14):3530-3541.
Yoshida and Hunter, The Immunobiology of Interleukin-27. Annu Rev Immunol. 2015;33:417-443.
Zhang, I-TASSER server for protein 3D structure prediction. BMC Bioinformatics. Jan. 23, 2008;9:40.
International Preliminary Report on Patentability issued in PCT/EP2018/061561 dated Nov. 5, 2019 (7 pages).

\* cited by examiner

Figure 1

```
         10         20         30         40         50
  MGQTAGDLGW RLSLLLLPLL LVQAGVWGFP RPPGRPQLSL QELRREFTVS
         60         70         80         90        100
  LHLARKLLSE VRGQAHRFAE SHLPGVNLYL LPLGEQLPDV SLTFQAWRRL
        110        120        130        140        150
  SDPERLCFIS TTLQPFHALL GGLGTQGRWT NMERMQLWAM RLDLRDLQRH
        160        170        180        190        200
  LRFQVLAAGF NLPEEEEEEE EEEEEERKGL LPGALGSALQ GPAQVSWPQL
        210        220        230        240
  LSTYRLLHSL ELVLSRAVRE LLLLSKAGHS VWPLGFPTLS PQP
``` a b c d

Figure 3 d

RMSD= 1.0 Å

Figure 5 a

| Species | Sequence |
|---|---|
| CALLORHINCHUS_MILII | ------------------MAVFFLLLLSLTELVLSAPTD-------PNALNLSFHQSLN |
| ALLIGATOR_MISSISSIPPIENSIS | ---------------MRTLG--LAV-VLSALLG-A---GGSRPP-PPPRWALGLGPEFRSSWK |
| SARCOPHILUS_HARRISII | ---------------MFSSIFQGLNLLLFSLLLNKAVTCGFPWPRRQPPHGLLDMRSEFKISLR |
| CRITECULUS_GRISEUS | ---------------MGQVTGGLGWRLSLLLLPLLLVQAGAWGFPTG-----PLSLQELRREFTVSLY |
| MUS_MUSCULUS | ---------------MGQVTGDLGWRLSLLLLPLLLVQAGSWGFPTD-----PLSLQELRREFTVSLY |
| RATTUS_NORVEGICUS | ---------------MGQVTGGLGWRLSLLLLPLLMVQTGSWGFPAD-----PLSLQELRREFTVSLY |
| ORYCTOLAGUS_CUNICULUS | ---------------MGQTAGNLGWRLSLLLLSLLLVRAGVWGFPRPPQS-----PQELRREFTVSLH |
| MACACA_MULATTA | ---------------MGQTAGNLGWRLSLLLLPLLLVQAGVWGFPRPPGRPPGRPQLSLQELRREFTVSLH |
| HOMO_SAPIENS | MGQT--------AGDLGWRLSLLLLPLLLVQAGVWGFPRPPGRPPGRQLSVQKLQREFTVSLH |
| GORILLA_GORILLA_GORILLA | MKDRPEDGPYPQVLAGTNRLSLLLLPLLLVQAGVWGFPRPPGRPPGRQLSLQELRREFTVSLH |
| BOS_TAURUS | ---------------MGQTAGNLGWRLSLLLLFLLLARAGVWGFPRPPGRPPGRPPLSLQELQREFKVSLH |
| SUS_SCROFA | ---------------MGQMADDLGWRLSLLLLSLLLARAGVWGFPRPPGRPPGRPPLSLQELQREFKVSLH |
| ORCINUS_ORCA | ---------------MGQTAGDLGWRVSLLLLSLLLARAGVWGFPRPPGRPLRSLQELQREFKVSLH |
| URSUS_MARITIMUS | ---------------MGQMAGDLGWRLSLLLLSLLLARAGVWGFPRPPGRSPLSLQELQREFKVSLQ |
| EQUUS_CABALLUS | ---------------MGQTAGDLGWRLSLLLLSLLLARAGVWGFPRPPGRSPLSLQELQREFKVSLH |
|  | *    : .:: :    *    .        *  . : * |

Figure 5 cont'd

| Species | Sequence |
|---|---|
| CALLORHINCHUS_MILII | LSRKILQDVQHLLLKYKQEKIGNPSFEDYNLMLGSLPSCQVDYRSWLEQQDEERILLNCR |
| ALLIGATOR_MISSISSIPPIENSIS | LAQKLLVETRELTRDFVLRHLPGVQLQ-LLPLSEQLLPGSLRTRDWLGLTVLARIQGLGA |
| SARCOPHILUS_HARRISII | LARKLLSEIRGIAHLFADTHLVGVSLD-FLPLTEQLPNVTMTFKTWLQLSDPDRICLLSS |
| CRITECULUS_GRISEUS | LARKLLSEAQGYVHSFAESRLPGVNLD-LLPLGHHLPNVSLTFQAWRHLSDPERICFLST |
| MUS_MUSCULUS | LARKLLSEVQGYVHSFAESRLPGVNLD-LLPLGYHLPNVSLTFQAWHHLSDSERICFLAT |
| RATTUS_NORVEGICUS | LARKLLSEVQGYVHSFAESRLPGVNLD-LLPVGHHLPNVSLTFQAWRHLSDSDRICFLAT |
| ORYCTOLAGUS_CUNICULUS | LARKLLSEVRGQAHRFAEAHLPGVNLD-LLPLGEQFPNVSLTFQVWRQLSDSERICFLSA |
| MACACA_MULATTA | LARKLLSEVRGQAHRFAESHLPGVNLD-LLPLGEQFPDVSLTFQTWRRLSDLERICFLST |
| HOMO_SAPIENS | LARKLLSEVRGQAHRFAESHLPGVNLY-LLPLGEQLPDVSLTFQAWRRLSDPERICFIST |
| GORILLA_GORILLA_GORILLA | LARKLLSEVRGQAHRFAESHLPGVNLY-LLPLGEQLPDVSLTFQAWRRLSDPERICFIST |
| BOS_TAURUS | LARKLLSEVRVQAHHFAESHLPGVNLD-LLPLAEQLPNVSTTFQAWRGLSALSRIDLVME |
| SUS_SCROFA | LARKLLSEVRVQARHFAESHLPGVNLD-LLPLGEQLPNVSLNFQAWRGLSDPERICFLSM |
| ORCINUS_ORCA | LSRKLLSEVRVQARDFAESHLPGVNLD-LLPLGEQLPNVSLTFQAWRGLSDPERIRFLSM |
| URSUS_MARITIMUS | LARKLLSEVRTQAHHFAESHLPGVSLD-LLPLGDQLPNVSLTFQAWHSLSDPERICFLSM |
| EQUUS_CABALLUS | LARKLLSEVRAQAHRFAESHLPGVSLD-LLPLGDQLPNVSMTFQAWRSLSDPERICFLSM |
| | *::.*:*      : .  :    . :  :   : :         *:    .    *: |

Figure 5 cont'd

```
CALLORHINCHUS_MILII              DLQVFWMHVDTKRVHELGQSQDSALLESMEAISLDLRDLISQLNSQISALNGSSPDTSTL
ALLIGATOR_MISSISSIPPIENSIS       ALPQYRGALARLGLPG---GDPE-FAQRLQDVDWDLRDLAHHVAYQLSVARAAA-----
SARCOPHILUS_HARRISII             LLGHFQTPLGELEGHQ---GWKGSLRKRLWTAQLDLRDLRSHLHYQMKAIGYSSREDEEA
CRITECULUS_GRISEUS               TLRPFPALLEGLGNQG---TWTSSERGQLWAMRLDLRDLHRHFRFQVLAAGFNQSAEEEE
MUS_MUSCULUS                     TLRPFPAMLGGLGTQG---TWTSSEREQLWAMRLDLRDLHRHLRFQVLAAGFKQSKEEED
RATTUS_NORVEGICUS                TLRPFPALLGGLETQR---TWTSSEREQLWAMRLDLRDLHRHLRFQVLAVGFSQSEEEKE
ORYCTOLAGUS_CUNICULUS            ALRPFRGLLGELGTSQ---PG-------HCLTPGLLLQVLAAGCDLPEQEER
MACACA_MULATTA                   TLQPFRALLGGLGTQG---RWTNTERMQLWAMRLDLRDLQRHLRFQVLAAGFNLPEEEEE
HOMO_SAPIENS                     TLQPFHALLGGLGTQG---RWTNMERMQ-WAMRLDLRDLQRHLRFQVLAAGFNLPEEEEE
GORILLA_GORILLA_GORILLA          TLQPFHALLGGLGTQG---RWTNMERMQLWAMRLDLRDLQRHLRFQVLAAGFNLPEEEEE
BOS_TAURUS                       WME--TGVVLGMGPRE---SWTSSERMQLQATRLDLRDLQQHLRFQVLAAGFNLPEE--H
SUS_SCROFA                       TLRPFHTLLGGLGSQG---FWTSSERMQ-WAIRLDLRDLQQHLRFQVLAAGFNLPGQEEE
ORCINUS_ORCA                     TLHPFHTLLGGLGSQG---FWTSSERLQLWAMRLDLRDLQQHLRFQVLAAGFNLPEE--E
URSUS_MARITIMUS                  MLRPFHVLLGRLGNQG---GWTSSEKMQLWTVRLDLRDLQRHLRFQVLAAGLNLPEE--E
EQUUS_CABALLUS                   TLRPFHALLGGLGSQG---GWTSSERMQLWAMRLDLRDLQRHLHFQVLAAGFNLPEE--E
                                                                          *        *:      .
```

Figure 5 cont'd

```
CALLORHINCHUS_MILII              T-----------LP------NDVLNPLYDWHSRLQGYIIFRDLEVYLNKVVRDFTVLKK
ALLIGATOR_MISSISSIPPIENSIS       ------------------PPPRPPPAPRAVWRRLQATAVTLRSLEAVLARAARDFALLRR
SARCOPHILUS_HARRISII             R-----------------GPEERALRRISLTVRQVSWPQLLRTYQLLRSLELVLARAVRDFLLLSK
CRITECULUS_GRISEUS               EEEEEEEEEGKELLLGALDGPKQVSSQVSWPQLLYTYQLLHSLELVLSRAVRDLLLLTM
MUS_MUSCULUS                     KEEEEEEEEKKLPLGALGGPNQVSSQVSWPQLLYTYQLLHSLELVLSRAVRDLLLLSL
RATTUS_NORVEGICUS                EEEEDEEEEEGKELLLGALGGPNQVSSQVSWPQLLYAYQLLHSLELVLSRAVRDLLLLSL
ORYCTOLAGUS_CUNICULUS            -----------EEGKGLLPGAPGGPSPAWAQLSWPQLLYNYQLLHSLELVLSRAVRDLLLLSK
MACACA_MULATTA                   E-E-EEEEEERKGLLPGALGNASQGPAQVSWPQLLSTYRLLHSLELVLSRAVRDLLLLSK
HOMO_SAPIENS                     E-E-EEEEEEERKGLLPGALGSALQGPAQVSWPQLLSTYRLLHSLELVLSRAVRELLLSK
GORILLA_GORILLA_GORILLA          E-EEEEEEEERKGLLPGALGSALQGPAQVSWPQLLSTYRLLHSLELVLSRAVRELLLSQ
BOS_TAURUS                       ------ENEEEKGLLPGALGAPLQISAQVSWSRFLYTYRLLHSLELLLSRTVRDLLLLSR
SUS_SCROFA                       ------ENEAGRELLPGAPGGPSKPAAQVSWPRLLYTYQLLHSLELVLSRAMRDFLLLSR
ORCINUS_ORCA                     ------ENEEGEGLLPGALGGPLQMSAQPSWPQLLYTYQSLHSLELVLARAVRDLLLLSQ
URSUS_MARITIMUS                  ------N-EERKGLLEWAPGGPSQISAQPSWPQLLYTYQLLHSLELVLARAVRDLLLLSQ
EQUUS_CABALLUS                   ------ENEKGKELLTGAPGSPSQTSVQVSWPQLLYTYQLLHSLELVLSRAVRDLLLLSQ
                                                      *         ::**  *  :: *:::  :*
```

Figure 5 cont'd

| Species | Sequence |
|---|---|
| CALLORHINCHUS_MILII | H------- |
| ALLIGATOR_MISSISSIPPIENSIS | LVPAPL-- |
| SARCOPHILUS_HARRISII | EVAQSQSLAT |
| CRITECULUS_GRISEUS | SPHPDPALGS |
| MUS_MUSCULUS | PRRPGSAWDS |
| RATTUS_NORVEGICUS | PRRPDSACDP |
| ORYCTOLAGUS_CUNICULUS | AGHPVQALGLPTTQPQP |
| MACACA_MULATTA | AGHSVWPLGFPTLGPQP |
| HOMO_SAPIENS | AGHSVWPLGFPTLSPQP |
| GORILLA_GORILLA_GORILLA | AGHSVWPLGFPTSSPQP |
| BOS_TAURUS | AGNSVQALGFPTPSSQP |
| SUS_SCROFA | AGNPAPALGFPTPSSPP |
| ORCINUS_ORCA | AGNPAQALGFPTPSSQP |
| URSUS_MARITIMUS | AGNPAPALGCSTSSSQP |
| EQUUS_CABALLUS | AGNPAQALGCPTPSSQP | a b

Figure 11

ER import sequence

```
human   MTPQLLLALVLWASCPPCSGRKGPPAALTLPRVQCRASRYPIAVQCSWTLPPAPNSTSPV 60
murine  MSKLLFLSLALWASRSPGYTE-TALVALSQPRVQCHASRYPVAVQCSWTPLQAPNSTRST 59
        *  :: *** *.    *  *  **** ****.*** ** * *****
```

```
human   SFIATYRLGMAARGHSWPCLQQTPTSTSCTTDVQLFSMAPYVLNVTAVHPWGSSSSFVP 120
murine  SFIATYRLGVATQQQSQPCLQRSPQASRCTPDVHLFSTVPYMLNVTAVHPGGASSSLLA 119
        *********  :: . ** *: .  :* * ** **:.***:*******  ***  .
```

```
human   FITEHIIKPDPPEGVRLSPLAERQLQVQWEPPGSWPFPEIFSLKYWIRYKRQGAARFHRV 180
murine  FVAERIIKPDPPEGVRLRTA-GQRLQVLWHPPASWPFPDIFSLKYRLRYRRRGASHFRQV 178
        *: *:************   * :****  *.* *****:******  **:::**::*:*
```

```
human   GPIEATSFILRAVRPRARYVQVAAQDLTDYGELSDWSLPATATMSLGK- 229
murine  GPIEATTFTLRNSKPHAKYCIQVSAQDLTDYGKPSDWSLPGQVESAPHKP 228
        ****** * **..:* *:* :**:********  ****** .  *
```

CRETION-COMPETENT MUTEINS OF THE HUMAN IL-27 ALPHA-SUBUNIT

CROSS-REFERENCE TO RELATED APPLICATIONS

The present invention is filed under 35 U.S.C. § 371 as the U.S. national phase of International Application No. PCT/EP2018/061561, filed May 4, 2018, which designated the U.S. and claims the right of priority of European patent application No. 17169358.3, filed with the European Patent Office on May 4, 2017. The entire disclosures of the above-identified priority applications are hereby fully incorporated herein by reference.

SEQUENCE LISTING

The instant application contains a Sequence Listing which has been submitted in ASCII format via EFS-Web and is hereby incorporated by reference in its entirety. Said ASCII copy, created on Oct. 25, 2019, is named SCH-5400-US_SeqListing.txt and is 75 kilobytes in size.

FIELD OF THE INVENTION

The present invention refers to a secretion-competent mutein (mutant proteins) of the alpha-subunit of human Interleukin 27 (SEQ ID NO: 1) and to a secretion-competent mutein of human heterodimeric Interleukin 27, wherein the alpha-subunit thereof is a secretion-competent mutein of the alpha-subunit of human Interleukin 27 (SEQ ID NO: 1). The invention also refers to a secretion-competent mutein of the alpha-subunit of human Interleukin 27, wherein the mutein comprises at least 76% sequence identity to the alpha-subunit of human Interleukin 27 (SEQ ID NO: 1). The invention also refers to a secretion-competent mutein of human heterodimeric Interleukin 27, wherein the alpha-subunit thereof comprises at least 76% sequence identity to the alpha-subunit of human Interleukin 27 (SEQ ID NO: 1). Interleukin 27 comprises the alpha-subunit p28 and the beta-subunit EBI3. The invention further refers to a nucleic acid molecule comprising a nucleotide sequence encoding a secretion-competent mutein of the alpha-subunit of human Interleukin 27 or encoding a secretion-competent mutein of the human heterodimeric Interleukin 27, wherein the alpha-subunit thereof is a secretion-competent mutein of the alpha-subunit of human Interleukin 27 as described herein. The invention further refers to a host cell containing a nucleic acid molecule comprising a nucleotide sequence encoding a secretion-competent mutein of the alpha-subunit of human Interleukin 27 or a secretion-competent mutein of the human heterodimeric Interleukin 27, wherein the alpha-subunit thereof is a secretion-competent mutein of the alpha-subunit of human Interleukin 27 as described herein. The invention also refers to an immune modulator comprising a secretion-competent mutein of the alpha-subunit of human Interleukin 27 or a secretion-competent mutein of the human heterodimeric Interleukin 27, wherein the alpha-subunit thereof is a secretion-competent mutein of the alpha-subunit of human Interleukin 27 as described herein, to the use of a secretion-competent mutein of the alpha-subunit of human Interleukin 27 as described herein or a secretion-competent mutein of the human heterodimeric Interleukin 27 as described herein for the manufacture of a medicament, to a method of treating an Interleukin 27-mediated disease comprising the step of administering a composition comprising a mutein of the present invention to a mammal in need thereof as well as to a method of producing a secretion-competent mutein of the alpha-subunit of human Interleukin 27 or a secretion-competent mutein of the human heterodimeric Interleukin 27, wherein the alpha-subunit thereof is a secretion-competent mutein of the alpha-subunit of human Interleukin 27 as described herein or a secretion-competent mutein comprising at least 76% sequence identity to the alpha-subunit of human Interleukin 27. Additionally, the present invention refers to any mutein as described herein for use in the treatment of infectious diseases, auto-immune diseases, cancer, transplantation-related diseases, such as Graft-versus-Host-disease, chronic inflammatory diseases, such as chronic inflammatory bowel disease, acute inflammatory diseases, sepsis, septic shock, diabetes or asthma. The invention further refers to a secretion-incompetent mutein of the α-subunit of mouse Interleukin 27 (SEQ ID NO: 10), wherein at least one of the two cysteine residues at amino acid positions 103 and 158 is/are mutated or deleted. Due to such a mutation or deletion, the α-subunit of mouse Interleukin 27 (SEQ ID NO: 10), which is in general secretion-competent, becomes secretion-incompetent, meaning that the secretion now depends on the presence of EBI3. Thereby, the α-subunit of mouse Interleukin 27 (SEQ ID NO: 10) behaves like the α-subunit of human Interleukin 27 (SEQ ID NO: 1), which is extremely necessary for mouse models, which aim at imaging the human immune system.

The present invention also provides a secretion-competent mutein of the beta-subunit of mouse Interleukin 27 (SEQ ID NO: 35), wherein at least one of the amino acid residues at amino acid position 198 is mutated or deleted. The human beta-subunit of Interleukin 27 can be secreted alone, while—naturally—the mouse beta-subunit of Interleukin 27 is secretion-incompetent. Both, the mutein of the α-subunit of mouse Interleukin 27 (SEQ ID NO: 10) and the secretion-competent mutein of the beta-subunit of mouse Interleukin 27 (SEQ ID NO: 35) as described herein together display a phenocopy of the human system.

Additionally, the present invention also provides a mutein of mouse Interleukin 27, comprising an α-subunit p28 and a β-subunit EBI3, wherein the α-subunit is a secretion-incompetent mutein of the α-subunit of mouse Interleukin 27 (SEQ ID NO: 10) as described herein and/or wherein the β-subunit is a secretion-competent mutein of the β-subunit of mouse Interleukin 27 (SEQ ID NO: 35) as described herein.

BACKGROUND OF THE INVENTION

A central tenet of the human immune system is the balanced regulation of pro- and anti-inflammatory responses. This allows rapid eradication of threats while protecting the host. Interleukins (ILs) are structurally diverse small secreted proteins that mediate pro- and anti-inflammatory responses to maintain this balance. Among those, the Interleukin 12 (IL-12) family, which comprises four established members (IL-12, IL-23, IL-27 and IL-35)[1], epitomizes this concept of balanced immune regulation: IL-12 and IL-23 are mostly pro-inflammatory cytokines, whereas IL-35 performs immune-suppressive roles[1,2]. IL-27 is functionally diverse with immunomodulatory pro- and anti-inflammatory functions, acting on different types of T cells[3]. It can promote pro-inflammatory responses and synergize with IL-12 to induce interferon γ (IFNγ) production by naïve T cells and natural killer (NK) cells[4]; but IL-27 can also dampen immune responses by inducing IL-10 as an anti-inflammatory cytokine[5-7] or inhibiting responses of $T_H17$ cells[8,9], a cell type that has come into focus due to its role in a large variety of immune-mediated human diseases[10].

Interleukin 12 (IL-12) cytokines regulate T cell function and development, decisively influencing pro-versus anti-inflammatory responses. Each family member is a heterodimer, and additionally their isolated subunits regulate immune reactions. This endows the IL-12 family with unparalleled regulatory capacities but also puts high demands on their biosynthesis. The inventors of the present invention have surprisingly found out that differences in a single amino acid determine if IL-12 family subunits can be secreted autonomously, acting as an independent cytokine, or if they depend on heterodimerization for secretion.

Features shared by the IL-12 family, however, go beyond this central role in connecting innate and adaptive immunity. All IL-12 cytokines show structural hallmarks that set this family apart from other interleukins: Each of the IL-12 family members is a heterodimer composed of a 4-helical bundle α-subunit (IL-12α/p35, IL-23α/p19 and IL-27α/p28, respectively) and of a β-subunit composed of two fibronectin (Fn) domains (EBI3) or two Fn and one immunoglobulin (Ig) domains (IL-12β/p40)[11,12]. Of note, despite their distinct roles in regulating immune responses, all heterodimeric IL-12 family members are made up of only these three α- and two β-subunits and even further members may exist[13]. IL-12β is shared by the pro-inflammatory family members IL-12 and IL-23 and EBI3 is shared by the immunomodulatory/anti-inflammatory members IL-27 and IL-35. This raises important questions about structural features that mediate assembly specificity versus promiscuity within this family. It also poses an extra demand on the machinery of protein folding and quality control in the endoplasmic reticulum (ER), where all IL-12 family members are assembled prior to secretion. Insights into IL-12 family cytokine folding and assembly are very limited so far. It has been shown that all human α-subunits are retained in cells in isolation and depend on assembly with their cognate β-subunit in order to be secreted[4,14,15]. In the case of the family's founding member, IL-12, assembly-induced folding of the IL-12α-subunit by IL-12β underlies these processes[16], but otherwise the underlying mechanisms remain ill-defined.

Concerning the present invention, the inventors have focused on the structurally ill-characterized yet functionally highly diverse family member IL-27. Interestingly, when discovering IL-27, it was found that in contrast to its human orthologue, the mouse IL-27alpha-subunit (p28) can be secreted in isolation without its beta-subunit, whereas the secretion of human IL-27α strictly depends on EBI3[4]. And importantly, the mouse IL-27 alpha-subunit has been shown to exert immunomodulatory effects on IL-27 signaling by competing for IL-27 receptor binding[17]. This differences raise intriguing structural and evolutionary questions about assembly control of IL-27 in the ER and the different physiological roles of heterodimeric IL-27 versus its isolated alpha-subunit IL-27α. Moreover, the mouse IL-27 alpha-subunit is under discussion as possible competitive inhibitor of IL-27 signalling or could even exercise autonomous immunoregulatory functions. Accordingly, it would be desirable to have a human secretion-competent α-subunit of human IL-27 that can be secreted without the presence of its β-subunit. It is thus an object of the present invention to provide such secretion-competent proteins. Another object of the present invention is to provide a mouse IL-27 alpha-subunit which can only be secreted together with its beta-subunit EBI3 as the basis for mouse models that better resemble the human immune system.

Thus, the inventors of the present invention have analysed the underlying structural determinants and have revealed that a conformational switch coupled to disulfide bond formation regulates retention versus secretion concerning muteins of the alpha-subunit of IL-27. Using these insights, the inventors provide a more human-like IL-12 system in mice and add a new biologically active member to the human interleukin repertoire. The findings of the present inventors reveal a close link between protein folding and immunoregulation that can be used to engineer an organism's cytokine repertoire.

SUMMARY OF THE INVENTION

In a first aspect, the present invention provides a secretion-competent mutein of the α-subunit of human Interleukin 27 (SEQ ID NO: 1), wherein at least one of the amino acid residues of the α-subunit of human Interleukin 27 (SEQ ID NO: 1) selected from the group consisting of sequence positions 160, 161, 162, 163, 164, 165, 180, 181 and 182 is mutated. The invention also provides a secretion-competent mutein of the α-subunit of human Interleukin 27 (SEQ ID NO: 1), wherein the mutein comprises at least 76% sequence identity to the α-subunit of human Interleukin 27 (SEQ ID NO: 1). The present invention also provides a secretion-competent mutein of the α-subunit of human Interleukin 27 (SEQ ID NO: 1), wherein at least one of the amino acid residues of the α-subunit of human Interleukin 27 (SEQ ID NO: 1) selected from the group consisting of sequence positions 160, 161, 162, 163, 180, 181 and 182 is mutated. The invention also provides a secretion-competent mutein of the α-subunit of human Interleukin 27 (SEQ ID NO: 1), wherein the mutein comprises at least 76% sequence identity to the α-subunit of human Interleukin 27 (SEQ ID NO: 1).

In a further aspect, the present invention provides a secretion-competent mutein of the α-subunit of human Interleukin 27 (SEQ ID NO: 1), wherein at least one of the amino acid residues at sequence positions 160 to 165 is mutated and/or wherein at least one of the amino acid residues at sequence positions 180 to 182 is mutated. The present invention also provides a secretion-competent mutein of the α-subunit of human Interleukin 27 (SEQ ID NO: 1), wherein at least one of the amino acid residues at sequence positions 160 to 163 is mutated and/or wherein at least one of the amino acid residues at sequence positions 180 to 182 is mutated. Additionally, the present invention provides a secretion-competent mutein comprising at least 76% sequence identity to the α-subunit of human Interleukin 27 (SEQ ID NO: 1), wherein at least one of the amino acid residues at sequence positions 160 to 165 is mutated and/or wherein at least one of the amino acid residues at sequence positions 180 to 182 is mutated. Additionally, the present invention provides a secretion-competent mutein comprising at least 76% sequence identity to the α-subunit of human Interleukin 27 (SEQ ID NO: 1), wherein at least one of the amino acid residues at sequence positions 160 to 163 is mutated and/or wherein at least one of the amino acid residues at sequence positions 180 to 182 is mutated.

In another aspect, the present invention provides a secretion-competent mutein of the α-subunit of human Interleukin 27 (SEQ ID NO: 1), wherein at least one of the amino acid residues of the α-subunit of human Interleukin 27 (SEQ ID NO: 1) selected from the group consisting of sequence positions 161, 162, 163, 164 and 165 is mutated. Further, the present invention provides a secretion-competent mutein comprising at least 76% sequence identity to the α-subunit of human Interleukin 27 (SEQ ID NO: 1), wherein at least one of the amino acid residues of the α-subunit of human Interleukin 27 (SEQ ID NO: 1) selected from the group consisting of sequence positions 161, 162, 163, 164 and 165 is mutated. In another aspect, the present invention provides a secretion-competent mutein of the α-subunit of human Interleukin 27 (SEQ ID NO: 1), wherein at least one of the amino acid residues of the α-subunit of human Interleukin 27 (SEQ ID NO: 1) selected from the group consisting of sequence positions 161, 162 and 163 is mutated.

In a further aspect, the present invention provides a secretion-competent mutein of the α-subunit of human Interleukin 27 (SEQ ID NO: 1), wherein at least one of the amino acid residues of the α-subunit of human Interleukin 27 (SEQ ID NO: 1) selected from the group consisting of sequence positions 160, 161, 162, 163, 164, 165, 180, 181 and 182 is mutated to cysteine. In a further aspect, the present invention provides a secretion-competent mutein of the α-subunit of human Interleukin 27 (SEQ ID NO: 1), wherein at least one of the amino acid residues of the α-subunit of human Interleukin 27 (SEQ ID NO: 1) selected from the group consisting of sequence positions 160, 161, 162, 163, 180, 181 and 182 is mutated to cysteine. Further, the present invention provides a secretion-competent mutein of the α-subunit of human Interleukin 27 (SEQ ID NO: 1), wherein the mutein comprises at least 76% sequence identity to the α-subunit of human Interleukin 27 (SEQ ID NO: 1), wherein at least one of the amino acid residues of the α-subunit of human Interleukin 27 (SEQ ID NO: 1) selected from the group consisting of sequence positions 160, 161, 162, 163, 164, 165, 180, 181 and 182 is mutated to cysteine. Further, the present invention provides a secretion-competent mutein of the α-subunit of human Interleukin 27 (SEQ ID NO: 1), wherein the mutein comprises at least 76% sequence identity to the α-subunit of human Interleukin 27 (SEQ ID NO: 1), wherein at least one of the amino acid residues of the α-subunit of human Interleukin 27 (SEQ ID NO: 1) selected from the group consisting of sequence positions 160, 161, 162, 163, 180, 181 and 182 is mutated to cysteine.

In a further aspect, the present invention provides a secretion-competent mutein of the α-subunit of human Interleukin 27 (SEQ ID NO: 1), wherein at least one of the amino acid residues of the α-subunit of human Interleukin 27 (SEQ ID NO: 1) selected from the group consisting of sequence positions 161, 162, 163, 164 and 165 is mutated to cysteine. Additionally, the present invention provides a secretion-competent mutein of the α-subunit of human Interleukin 27 (SEQ ID NO: 1), wherein the mutein comprises at least 76% sequence identity to the α-subunit of human Interleukin 27 (SEQ ID NO: 1), wherein at least one of the amino acid residues of the α-subunit of human Interleukin 27 (SEQ ID NO: 1) selected from the group consisting of sequence positions 161, 162, 163, 164 and 165 is mutated to cysteine.

The term "secreting" or "secretion" is the active export of a protein from a cell into the extracellular environment. Generally secretion occurs through a secretory pathway in the cell, for example, in eukaryotic cells, this generally involves the endoplasmic reticulum and the golgi apparatus.

A mutein according to the present invention is "secretion-competent" or "comprises secretion competence", when the mutein is able to perform a complete passage through the secretory pathway of the cell and through the cytoplasmic membrane.

In contrast thereto, the term "non-secretion competent" muteins means in the context of the present invention muteins, which are not naturally secreted from the cell into the extracellular environment. This term also comprises that the "non-secretion" competent mutein can only be secreted from the cell into the extracellular environment when the β-subunit EBI3 is present. The term "secretion-incompetent" is used interchangeably herein with the term "non-secretion competent". These terms can also comprise that the respective mutein comprises a modulating secretion competency.

In a second aspect, the present invention provides a secretion-competent mutein of human Interleukin 27, which is secretion-competent as heterodimer, comprising an α-subunit p28 and a β-subunit EBI3, wherein the α-subunit is a secretion-competent mutein of the α-subunit of human Interleukin 27 (SEQ ID NO: 1). In a further embodiment thereof, the α-subunit is a secretion-competent mutein comprising at least 76% sequence identity to the α-subunit of human Interleukin 27 (SEQ ID NO: 1) as described herein.

In a third aspect, the present invention provides a nucleic acid molecule comprising a nucleotide sequence encoding the secretion-competent mutein of human Interleukin 27 or the secretion-competent mutein of the α-subunit of human Interleukin 27 (SEQ ID NO: 1) according to the present invention. In a further embodiment thereof, the nucleic acid molecule comprises a nucleotide sequence encoding a secretion-competent mutein of the α-subunit of human Interleukin 27 (SEQ ID NO: 1), wherein the secretion-competent mutein comprises at least 76% sequence identity to the α-subunit of human Interleukin 27 (SEQ ID NO: 1). In yet another aspect, the invention provides the nucleic acid molecule as described herein for use as a therapeutic agent.

In a fourth aspect, the present invention provides also a host cell containing a nucleic acid molecule according to the present invention.

In a fifth aspect, the present invention provides an immune modulator comprising a mutein according to the present invention.

In a sixth aspect, the present invention provides the use of a mutein according to the present invention for the manufacture of a medicament for treating infectious diseases, autoimmune diseases, cancer, transplantation-related diseases, such as Graft-versus-Host-disease, chronic inflammatory diseases, such as chronic inflammatory bowel disease, acute inflammatory diseases, sepsis, septic shock, diabetes or asthma in a mammal.

In a related aspect, the present invention provides a mutein according to the present invention for use as a medicament. Further, the present invention provides a mutein according to the present invention for use in the treatment of infectious diseases, autoimmune diseases, cancer, transplantation-related diseases, such as Graft-versus-Host-disease, chronic inflammatory diseases, such as chronic inflammatory bowel disease, acute inflammatory diseases, sepsis, septic shock, diabetes or asthma.

The present invention also provides a method of treating an Interleukin 27-mediated disease, preferably an infectious disease, an autoimmune disease, cancer, transplantation-related diseases, such as Graft-versus-Host-disease, a chronic inflammatory disease, such as chronic inflammatory bowel disease, acute inflammatory diseases, sepsis, septic shock, diabetes or asthma in a mammal, comprising the step of administering a composition comprising a mutein as described herein to a mammal in need thereof.

Additionally, the present invention provides a method for producing a mutein as described herein, comprising the steps of:

introducing into a nucleic acid molecule encoding the human Interleukin 27 polypeptide or the human Interleukin 27 α-subunit polypeptide or a polypeptide comprising at least 76% sequence identity to the human Interleukin 27 α-subunit polypeptide a nucleotide sequence mutating at least one amino acid residues of human Interleukin 27 or of the α-subunit of human Interleukin 27 or of a polypeptide comprising at least 76% sequence identity to the human Interleukin 27 α-subunit polypeptide selected from the group consisting of sequence positions 160, 161, 162, 163, 164, 165, 180, 181 and 182, and introducing the obtained nucleic acid molecule for expression into a suitable host cell or into a suitable cell extract or cell lysate.

The present invention also provides a method for producing a mutein as described herein, comprising the steps of:

introducing into a nucleic acid molecule encoding the human Interleukin 27 polypeptide or the human Interleukin 27 α-subunit polypeptide a nucleotide sequence mutating at least one amino acid residues of human Interleukin 27 or of the α-subunit of human Interleukin 27 selected from the group consisting of sequence positions 160, 161, 162, 163, 180, 181 and 182, and introducing the obtained nucleic acid molecule for expression into a suitable host cell or into a suitable cell extract or cell lysate.

The present invention also provides a method for producing a mutein as described herein, comprising the steps of:

introducing into a nucleic acid molecule encoding the human Interleukin 27 polypeptide or the human Interleukin 27 α-subunit polypeptide a nucleotide sequence mutating at least one amino acid residues of human Interleukin 27 or of the α-subunit of human Interleukin 27 selected from the group consisting of sequence positions 161, 162 and 163, and introducing the obtained nucleic acid molecule for expression into a suitable host cell or into a suitable cell extract or cell lysate.

In yet another aspect the invention provides a secretion-incompetent mutein of the α-subunit of mouse Interleukin 27 (SEQ ID NO: 10), wherein at least one of the two cysteines at amino acid positions 103 and 158 is/are mutated (i.e. replaced by another amino acid residue) or deleted. This means in this embodiment that the secretion of this mutein is not-autonom, but depends on the presence of EBI3. This secretion-dependent mutein of the α-subunit of mouse Interleukin 27 (SEQ ID NO:10) thus behaves like the human α-subunit of Interleukin 27 (SEQ ID NO:1).

In another aspect, the present invention also provides a secretion-competent mutein of the beta-subunit of mouse Interleukin 27 (SEQ ID NO: 35), wherein the amino acid residue at amino acid positions 198 is mutated or deleted. It is preferred in this embodiment that a secretion-competent mutein of the beta-subunit of mouse Interleukin 27 (SEQ ID NO: 35) is provided, wherein the amino acid residue at amino acid positions 198 is replaced by a tyrosine (SEQ ID NO: 36).

These aspects of the invention will be more fully understood in view of the following drawings, detailed description and non-limiting examples.

BRIEF DESCRIPTION OF THE DRAWINGS

The accompanying drawings are included to further an understanding of the embodiments that are incorporated in and constitute a part of this specification. The drawings illustrate embodiments and together with the description serve to explain principles of embodiments. Other embodiments and many of the intended advantages of embodiments will be readily appreciated, as they become better understood by reference to the detailed description. The elements of the drawings are not necessarily to scale relative to each other.

FIG. 1 shows the protein sequence of the wild-type α-subunit of human Interleukin 27 (SEQ ID NO:1) as also deposited under UniProtKB accession number Q8NEV9.

FIG. 2 shows that human and murine IL-27α differ in their secretion behavior from mammalian cells. FIG. 2(*a*) shows schematically heterodimeric IL-27 comprising the α-subunit p28 and the β-subunit EBI3 and how they are bound to its heterodimeric receptor. FIG. 2(*b*) shows that human IL-27α depends on co-expression of its β-subunit EBI3 for secretion. The human IL-27α-subunit (hIL-27α) was transfected alone or co-expressed with the human IL-27 β-subunit EBI3 (hEBI3, SEQ ID NO: 9) in 293T cells as indicated (mock displays an empty pSVL vector). 2% lysate (L) or medium (M) were immunoblotted against Hsc70 as loading control, the V5 epitope tag (hIL-27α) or hEBI3 (SEQ ID NO: 9). FIG. 2(*c*) shows that O-glycosylation gives rise to two species of secreted V5-tagged hIL-27α. 4% medium of cells co-transfected with hIL-27α (SEQ ID NO: 1) and hIL-27β (hEBI3 is β-subunit, SEQ ID NO: 9) was treated (displayed by the symbol +) with N-glycosidases (EndoH, PNGaseF) or an O-glycosidase as indicated, and subsequently immunoblotted against V5. Controls without enzyme are signed by (–). FIG. 2(*d*) shows that murine IL-27α can be secreted in isolation. The mouse IL-27α (mIL-27α) (SEQ ID NO: 10) subunit was transfected alone or co-expressed with hEBI3 (SEQ ID NO: 9) in 293T cells as indicated (mock displays empty pSVL vector). 2% lysate (L) or medium (M) were immunoblotted against Hsc70 as loading control, V5 (mIL-27α) or hEBI3 (SEQ ID NO: 9). The protein sequence of the wild-type alpha-subunit of mouse Interleukin 27 (SEQ ID NO: 10) is also deposited as genebank identifier NP_663611.1.

FIG. 3 shows that oxidative folding permits secretion of IL-27α in isolation. FIG. 3(*a*) shows potentially folding-relevant differences in the amino acid sequence of human and murine IL-27α. Identical residues are highlighted in grey (not black) without a box with dashed line, homologous residues are highlighted by a box with dashed line. Differences with a potential impact on (ER) folding are highlighted with a box with solid line, namely, the presence or absence of a predicted N-glycosylation site, an extra cysteine, or a lysine insertion interrupting a poly-glutamate stretch. Arrows indicate the position of cysteines. FIG. 3(*b*) shows the substitution of leucine 162 with cysteine (L162C, SEQ ID NO: 2) in human IL-27α, which leads to its secretion in isolation. hIL-27α (SEQ ID NO: 1), hIL-27α$^{D89N}$(SEQ ID NO: 31), hIL-27α$^{L162C}$ (SEQ ID NO: 2), hIL-27α$^{K168\ insertion}$ (SEQ ID NO: 32) or empty pSVL vector (mock) were transfected in 293T cells and 2% lysate (L) or medium (M) were immunoblotted against Hsc70 and V5. FIG. 3(*c*) shows structural models of mIL-27α (SEQ ID NO: 10) and hIL-27α (SEQ ID NO: 1). Homology models of mIL-27α (SEQ ID NO: 10) and hIL-27α (SEQ ID NO: 1) were generated using iTasser. Cysteines in mIL-27α (SEQ ID NO: 10) and the corresponding residues in hIL-27α (SEQ ID NO: 1) are shows in a CPK representation. FIG. 3(*d*) shows the superposition of murine and human IL-27αstructural models. RMSD calculations were performed using Yasara structure. FIG. 3(*e*) shows that secreted hIL-27α$^{L162C}$(SEQ ID NO: 2) forms a disulfide bridge. Left: Secreted hIL-27α$^{L162C}$ (SEQ ID NO: 2) was analyzed by non-reducing SDS-PAGE. 2% medium of cells were transfected, as indicated, with hIL-27α$^{L162c}$ (SEQ ID NO: 2), hEBI3 (SEQ ID NO: 9) or empty pSVL vector (mock) and were immunoblotted against V5 and EBI3. Where indicated with (+) in the line β-Me, samples were treated with β-mercaptoethanol. Dashed lines are shown to guide the eye and highlight mobility differences between reduced/non-reduced samples. Right: Same conditions were applied as in the experiment seen left, however, as indicated with (−) in the line β-Me, without treatment of β-mercaptoethanol.

Figure 4:
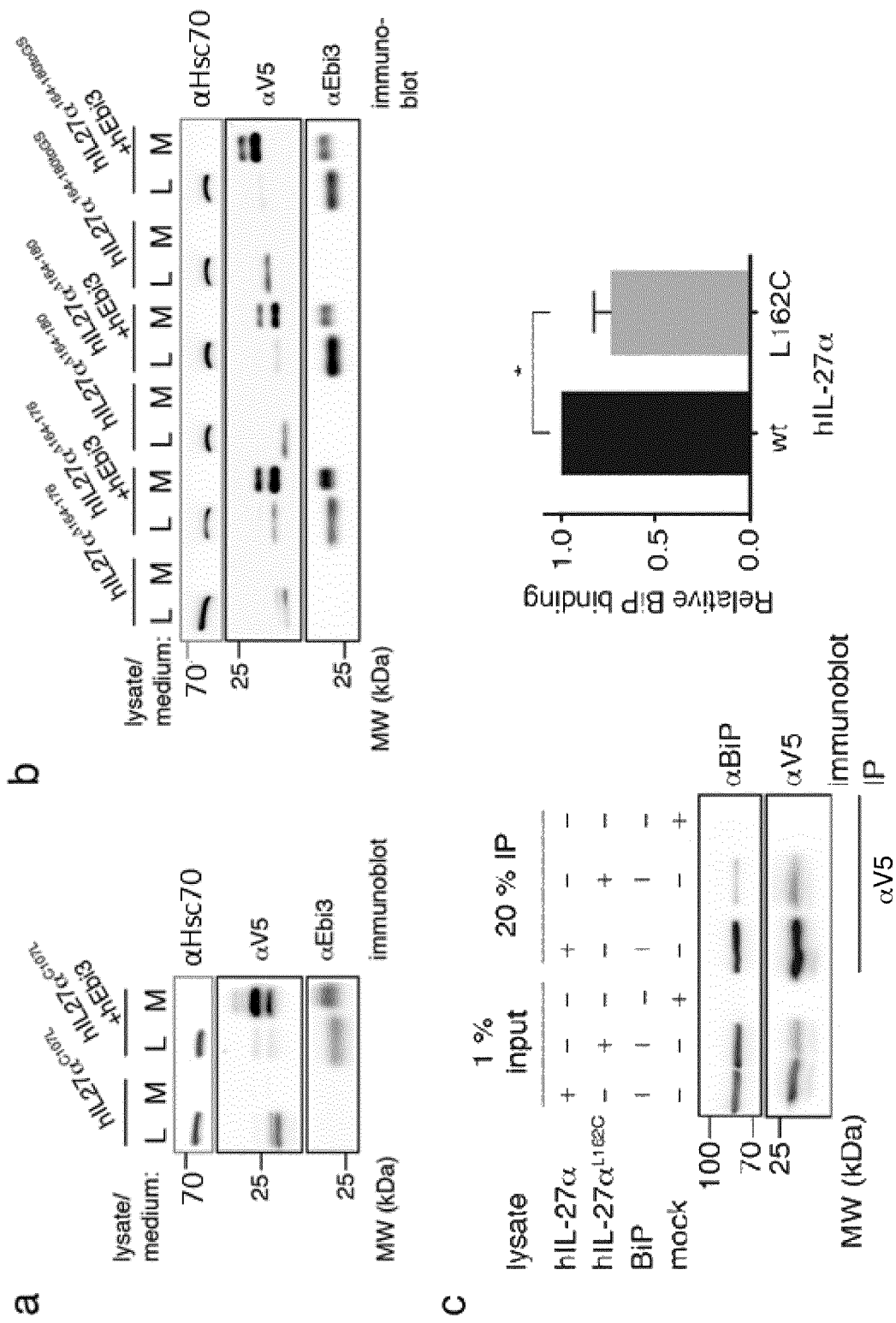
Figure 4:
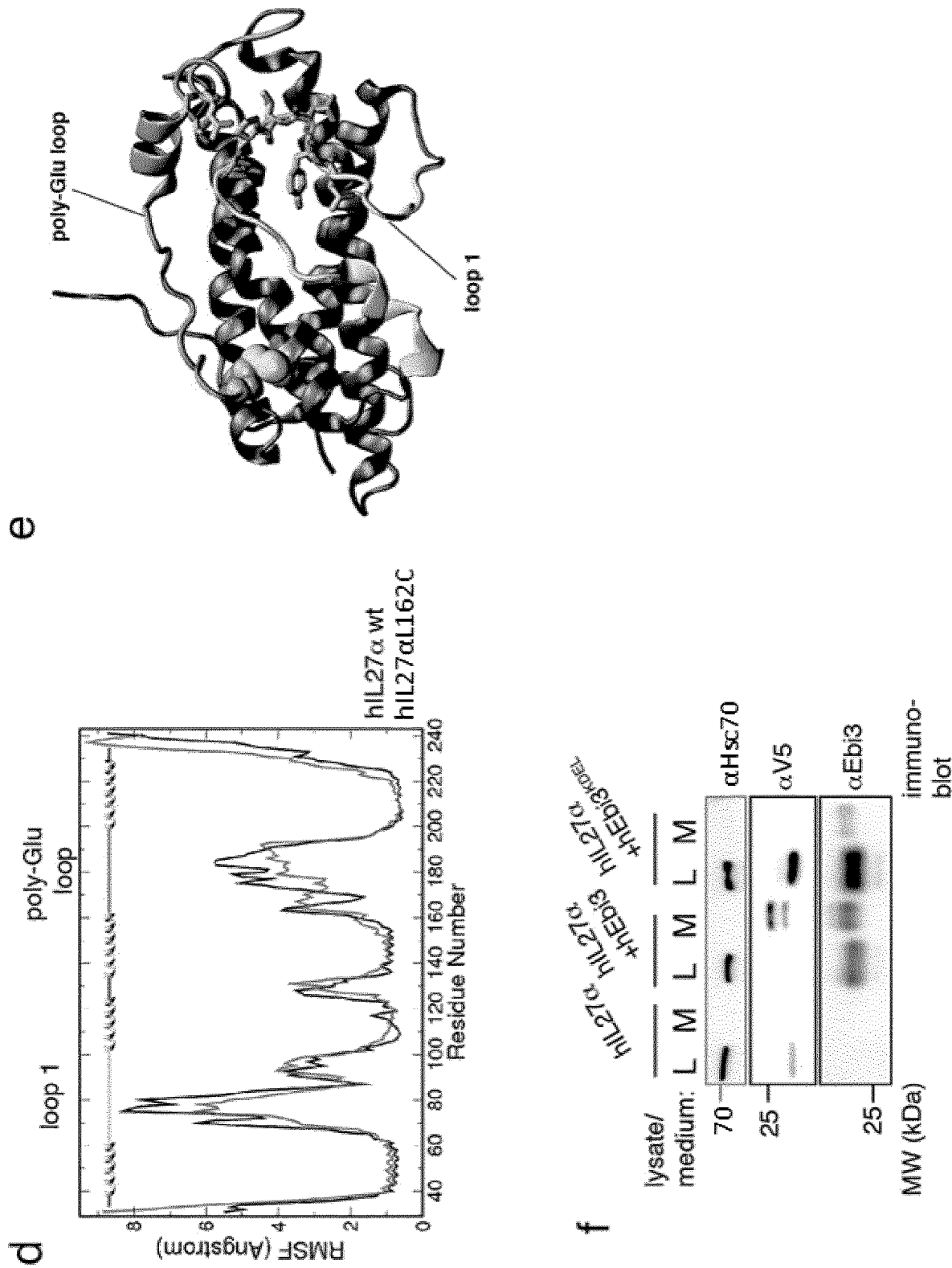

FIG. 4 shows determinants and chaperone recognition of incompletely folded hIL-27α (SEQ ID NO: 1). FIG. 4(a) shows that the single free cysteine does not lead to ER retention of hIL-27α (SEQ ID NO: 1). hIL-27α$^{107L}$ (SEQ ID NO: 28) is retained in the cell when expressed alone and secreted upon co-expression of hEBI3 (SEQ ID NO: 9). 293T cells were transfected with hIL-27α$^{C107L}$ (SEQ ID NO: 28) and hEBI3 (SEQ ID NO: 9) as indicated and 2% of lysate (L) or medium (M) was immunoblotted against Hsc70, V5 and EBI3. FIG. 4(b) shows that the flexible poly-glutamate loop does not cause ER retention of hIL-27α (SEQ ID NO: 1). hIL-27α$^{Δ164-176}$ (SEQ ID NO: 24), hIL-27α$^{Δ164-180}$ (SEQ ID NO: 25) and hIL-27α$^{164-180toGS}$ (SEQ ID NO: 26) are retained in the cell in isolation, whereas co-expression of hEBI3 (SEQ ID NO: 9) induces their secretion. hIL-27α$^{Δ164-176}$ (SEQ ID NO: 24), hIL-27α$^{Δ164-180}$ (SEQ ID NO: 25) or hIL-27α$^{164-180toGS}$ (SEQ ID NO: 26) and hEBI3 (SEQ ID NO: 9) were co-transfected in cells as indicated and 2% of lysate (L) or medium (M) were immunoblotted against Hsc70, V5 and EBI3. FIG. 4(c) shows that the chaperone BiP binds significantly better to wild type hIL-27α (SEQ ID NO: 1) than to hIL-27α$^{L162c}$ (SEQ ID NO: 2). 20% lysate of cells were transfected with hIL-27α (SEQ ID NO: 1) or hIL-27α$^{L162c}$ (SEQ ID NO: 2) and hamster BiP or empty pSVL vector (mock) and, as indicated, were immunoprecipitated with anti-V5 antibody and immunoblotted against BiP and V5 (N=4±SD; *p<0.05). Normalization was performed as described in the Examples section with the signals of the wild type (wt) set to 1. FIG. 4(d) shows molecular dynamics simulations and reveals locally confined reduced flexibility in hIL-27α$^{L162c}$ (SEQ ID NO: 2). The root means square fluctuation (RMSF) for wt hIL-27α (SEQ ID NO: 1) and hIL-27α$^{L162c}$ (SEQ ID NO: 2) with its disulfide bridge formed are overlayed. FIG. 4(e) shows regions with reduced flexibility in hIL-27α$^{L162c}$ (SEQ ID NO: 2) with its formed disfulfide bridge as compared to wt hIL-27α (shown as balls). A putative cluster of hydrophobic residues is shown in a stick representation. FIG. 4(f) shows that hIL-27α needs to be secreted as a heterodimer with hEBI3 (SEQ ID NO: 9). 293T cells were transfected with hIL-27α (SEQ ID NO: 1) alone or together with hEBI3 (SEQ ID NO: 9) or hEBI3$^{KDEL}$ (SEQ ID NO: 27). 2% of lysate (L) or medium (M) was immunoblotted against Hsc70, V5 and EBI3.

Figure 5:
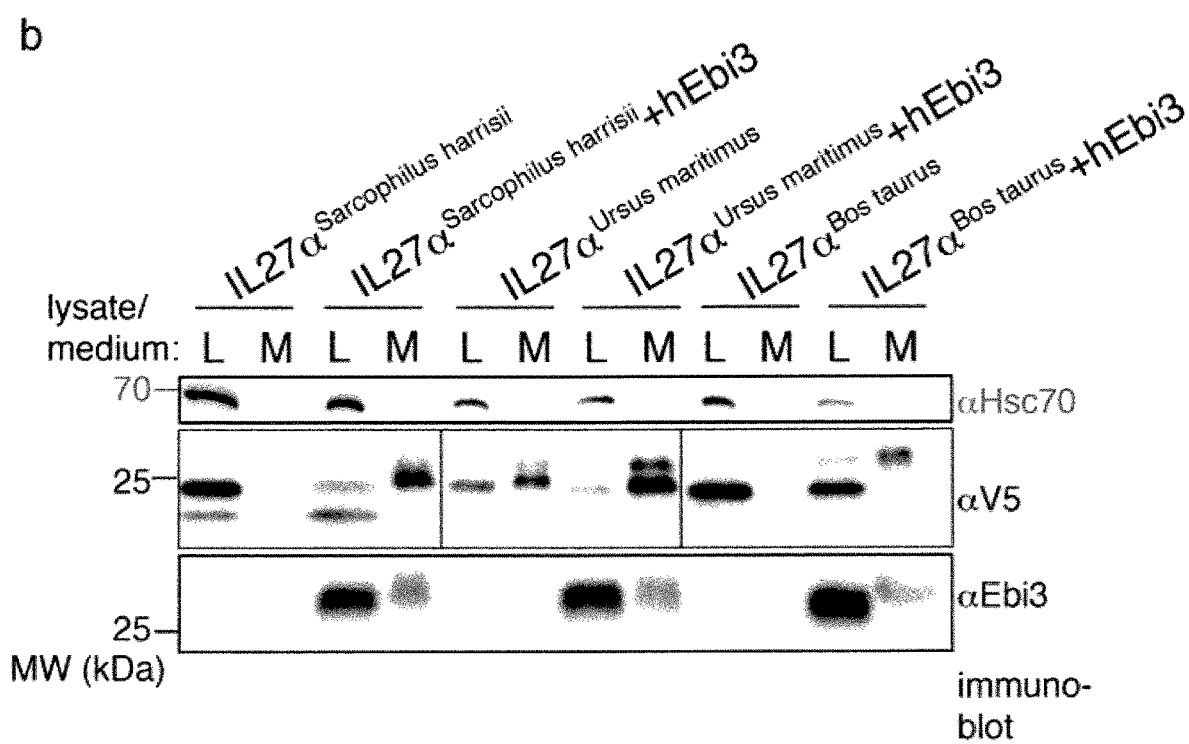
Figure 5:
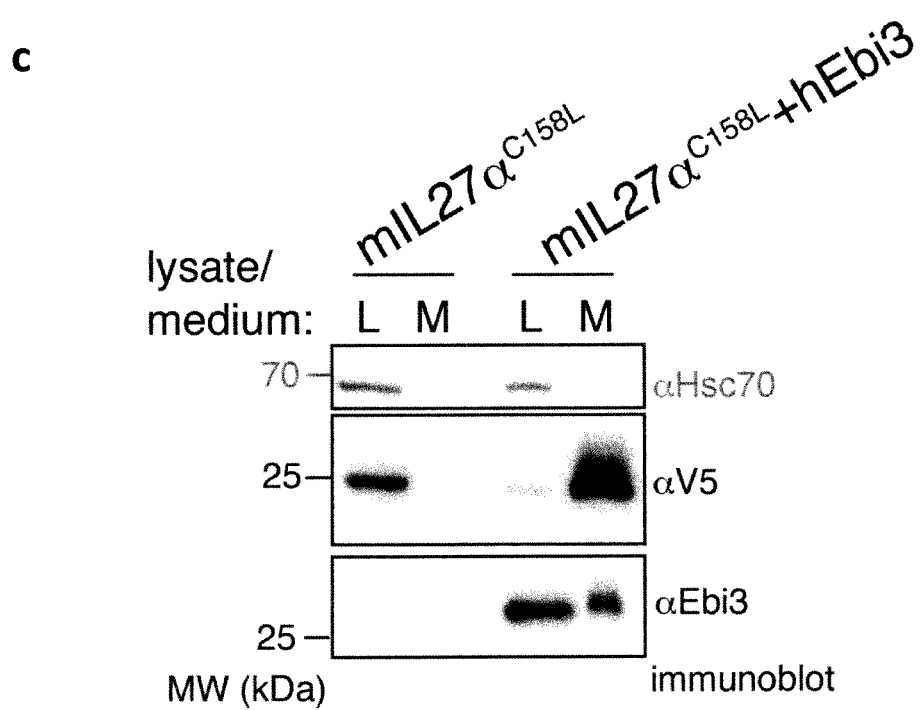

FIG. 5 displays a species comparison of IL-27α secretion. FIG. 5(a) shows a sequence alignment of IL-27α from different species and reveals differences in their cysteine content and localization. Cysteines and corresponding positions are highlighted by boxes. FIG. 5(b) shows IL-27α from three different species as indicated, which were either expressed in isolation or in the presence of human EBI3 (SEQ ID NO: 9). 2% of lysate (L) or medium (M) of cells transfected with the indicated constructs was immunoblotted against Hsc70, V5 and hEBI3 (SEQ ID NO: 9). Due to the different expression levels/intenstities of IL-27α from different species, the middle blot is separated in sections with optimal exposure each. FIG. 5(c) shows that the substitution of cysteine 158 with leucine (C158L) in mouse IL-27α (SEQ ID NO: 29) leads to its dependency of EBI3 co-expression for secretion. The indicated constructs were transfected in 293T cells and 2% lysate (L) or medium (M) were immunoblotted against Hsc70, V5 and EBI3.

Figure 6:
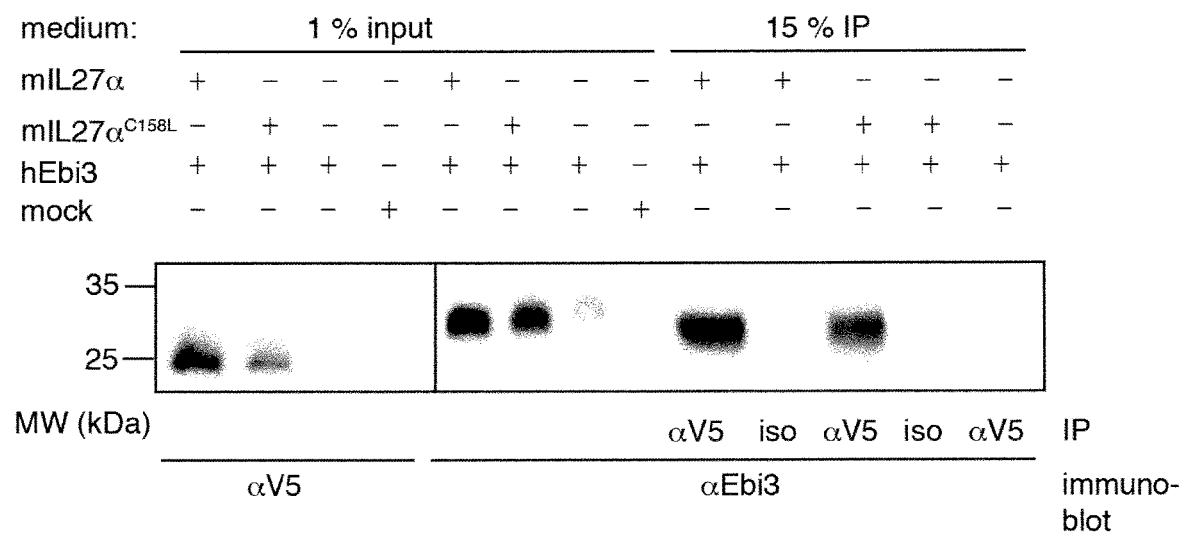

FIG. 6 shows the interaction between the murine IL-27α subunits (SEQ ID NO: 10) (SEQ ID NO: 29) and hEBI3 (SEQ ID NO: 9). Secreted mIL-27α (SEQ ID NO: 10) and mIL-27α$^{C158L}$ (SEQ ID NO: 29) both interact with hEBI3 (SEQ ID NO: 9). 1% medium of cells transfected with mIL-27α (SEQ ID NO: 10), mIL-27α$^{C158L}$ (SEQ ID NO: 29), empty pSVL vector (mock) and/or hEBI3 (SEQ ID NO: 9) as indicated was immunoblotted against V5 and EBI3 (SEQ ID NO: 9) (inputs). 15% medium of cells transfected with mIL-27α (SEQ ID NO: 10), mIL-27α$^{C158L}$ (SEQ ID NO: 29) and/or hEBI3 (SEQ ID NO: 9) were immunoprecipitated with α-V5 or an isotype control antibody and immunoblotted against EBI3.

Figure 7:
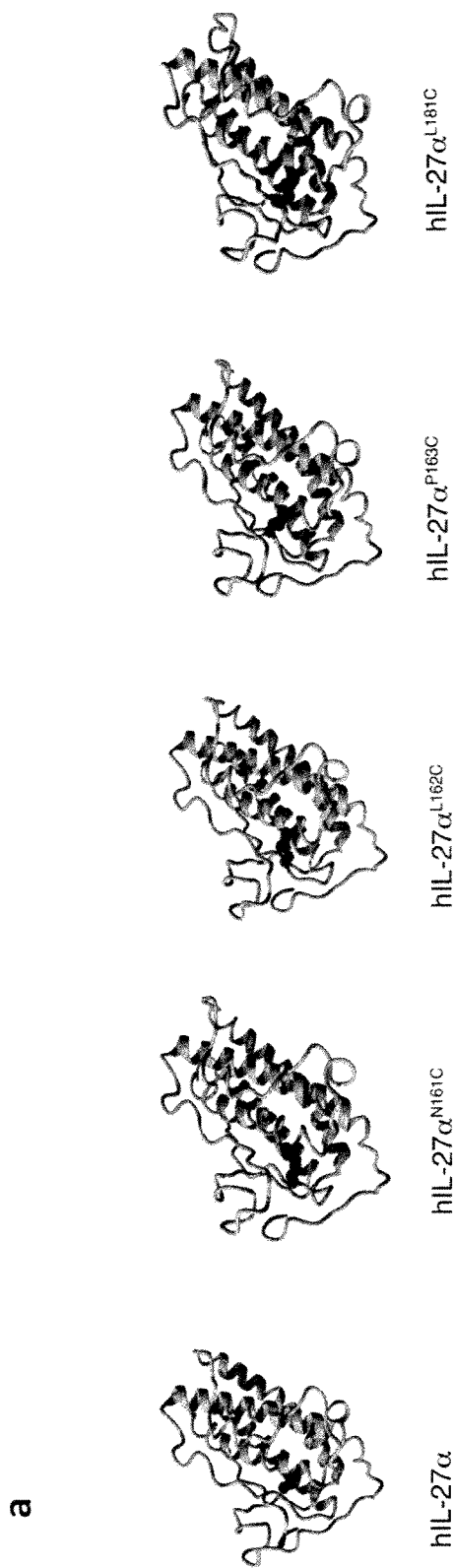
Figure 7:
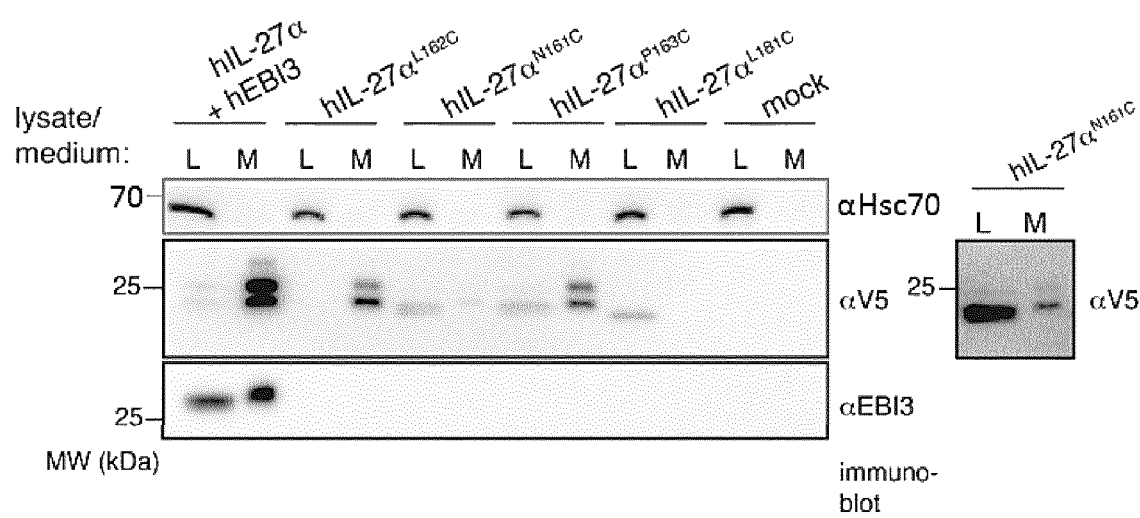
Figure 7:
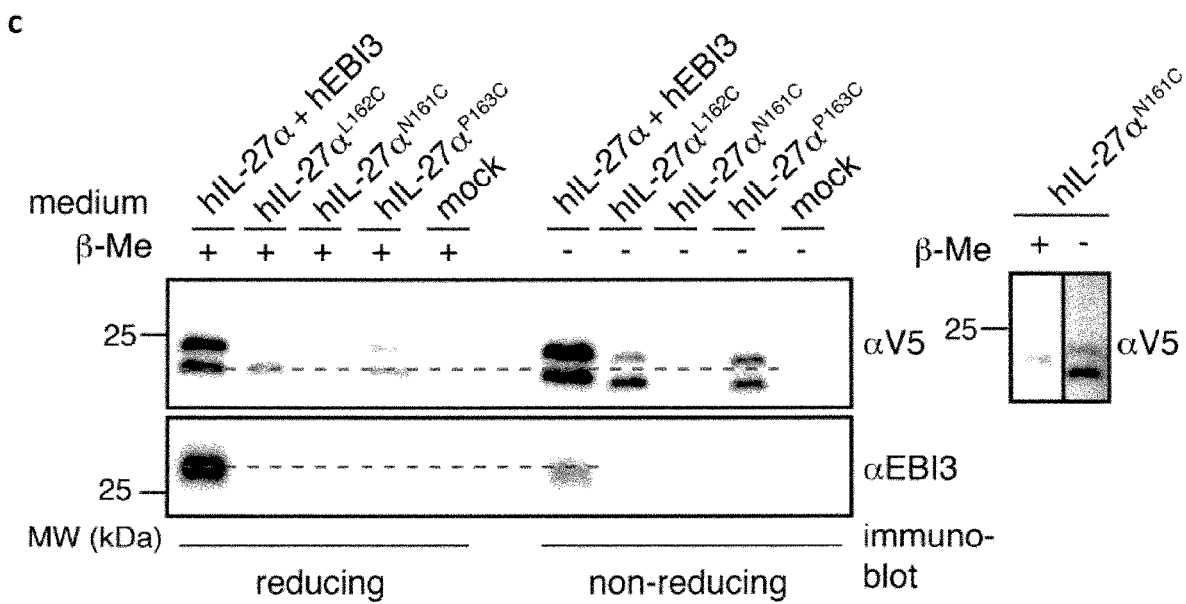

FIG. 7 shows that disulfide bond formation at and near the amino acid position 162 of hIL-27α leads to its secretion competency. FIG. 7(a) shows the structural models of hIL-27α (SEQ ID NO: 1), hIL-27α N161C (SEQ ID NO: 4), hIL-27α L162C (SEQ ID NO: 2), hIL-27α P163C (SEQ ID NO: 5), and hIL-27α L181C (SEQ ID NO: 7). The structural model of hIL-27α was generated by iTasser. Muteins (hIL-27α$^{N161C}$, hIL-27α$^{L162C}$, hIL-27α$^{P163C}$ and hIL-27α$^{L181C}$) were generated with Yasara structure. A disulfide bond was introduced between the two cysteines in silico and structures were subsequently energy minimized using Yasara structure. Cysteines are highlighted in ball/CPK representation. FIG. 7(b) shows that in addition to hIL-27α$^{L162C}$, the muteins hIL-27α$^{N161C}$ and hIL-27α$^{P163C}$ are secretion competent in isolation. hIL-27α and hEBI3, hIL-27α$^{N161C}$, hIL-27α$^{L162C}$, hIL-27α$^{P163C}$, hIL-27α$^{L181C}$ or empty pSVL vector (mock) were transfected in 293T cells and 2% medium (M) were immunoblotted against Hsc70, V5 and EBI3. An image with increased contrast is shown on the side for hIL-27α$^{N161C}$. FIG. 7(c) shows that in addition to hIL-27α$^{L162C}$, hIL-27α$^{N161C}$ and hIL-27α$^{P163C}$ form a disulfide bond. Secreted hIL-27α, hIL-27α$^{N161C}$, hIL-27α$^{L162C}$ and hIL-27α$^{P163C}$ were analyzed by non-reducing SDS-PAGE. 2% medium of cells transfected as depicted was immunoblotted against V5 and EBI3. Where indicated (+) samples were treated with β-mercaptoethanol. Dashed lines are shown to highlight mobility differences between reduced/non-reduced samples. An image with increased contrast is shown on the side for hIL-27α$^{N161C}$.

Figure 8:
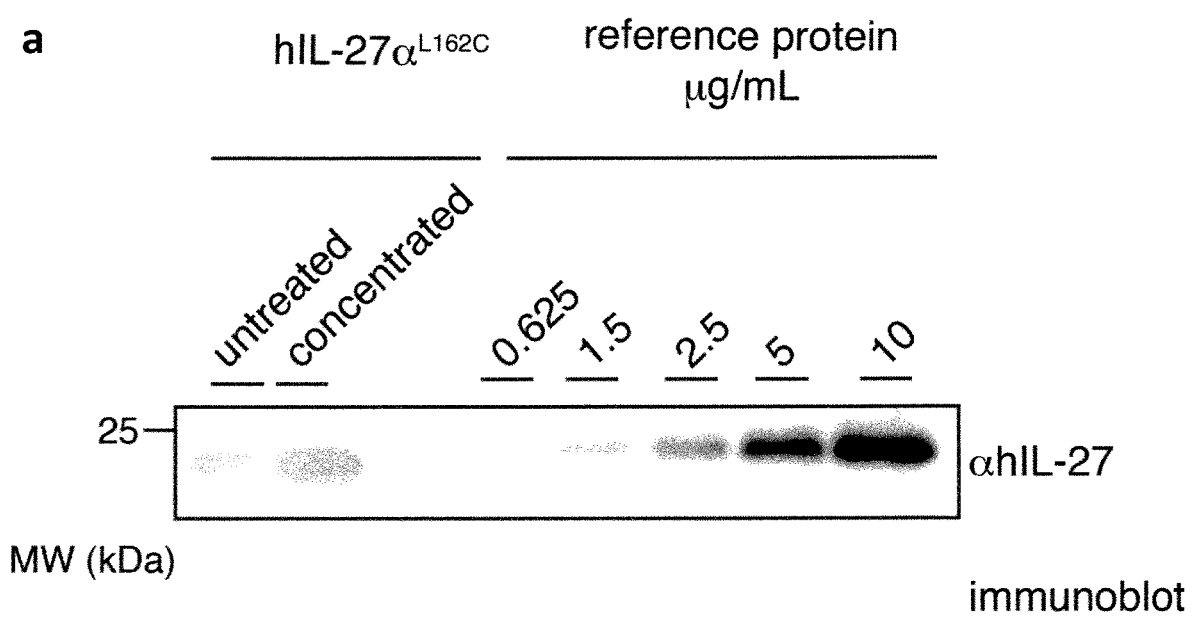
Figure 8:
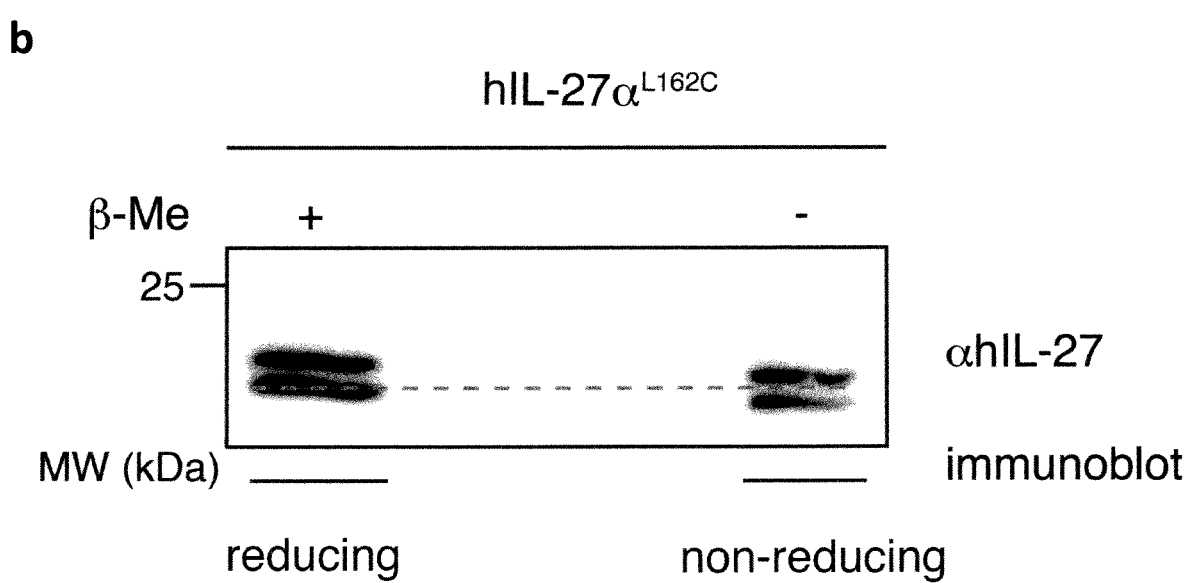

FIG. 8 shows in FIG. 8(a) the concentration determination of Expi293-secreted hIL-27α$^{L162C}$ using hIL-27α$^{L156C}$ His$_6$ from bacteria as a reference. Same volumes of cell supernatants of hIL-27α$^{L162C}$ expressing Expi293 cells and hIL-27α$^{L156C}$ His$_6$ standards with different concentrations were loaded onto SDS-PAGE gels and immunoblotted against IL-27α. The Expi293-expressed hIL-27α$^{L162C}$ concentration was determined by a linear fit to the signals of the bacterially expressed hIL-27α$^{L156C}$ His$_6$ standards. Where indicated, samples were further concentrated by ultrafiltration. Additionally, FIG. 8(b) shows that Expi293 expressed hIL-27α$^{L162C}$ forms a disulfide bond. 0.03% cell supernatant of hIL-27α$^{L162C}$-transfected Expi293 cells was analyzed on SDS-PAGE gel under reducing and non-reducing conditions and immunoblotted against hIL-27α. Where indicated (+) samples were treated with β-mercaptoethanol. Dashed lines are shown to guide the eye and highlight mobility differences between reduced/non-reduced samples.

Figure 9:
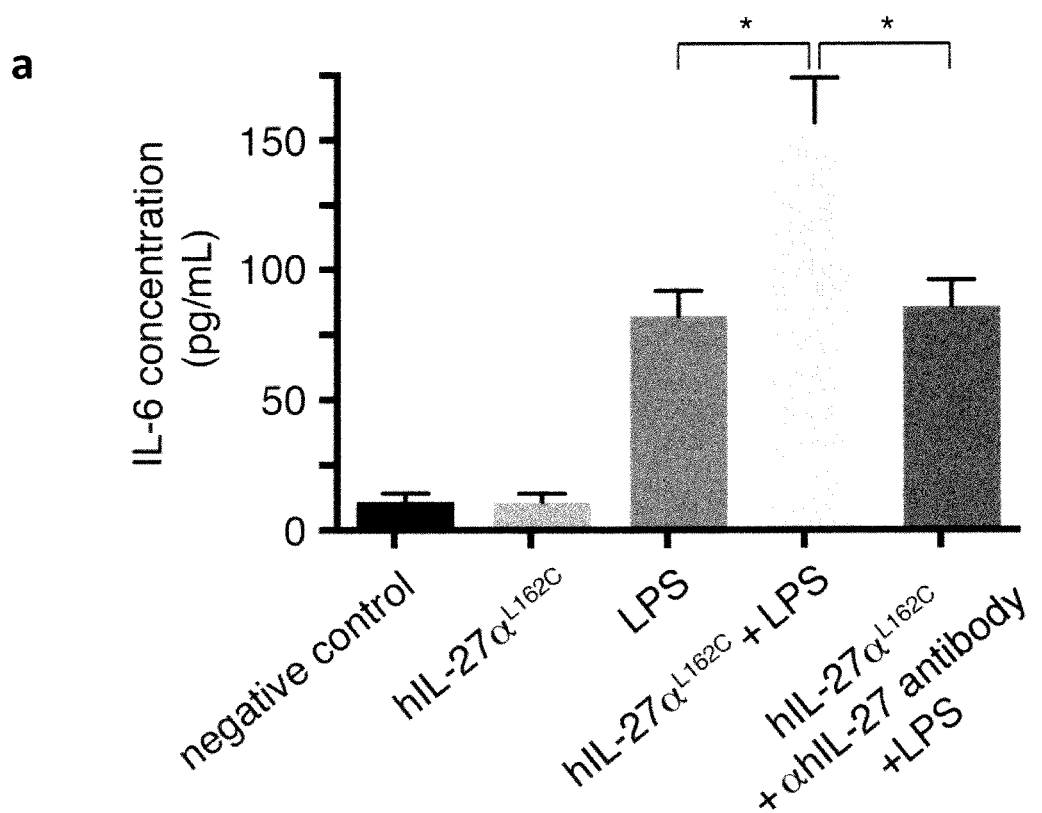
Figure 9:
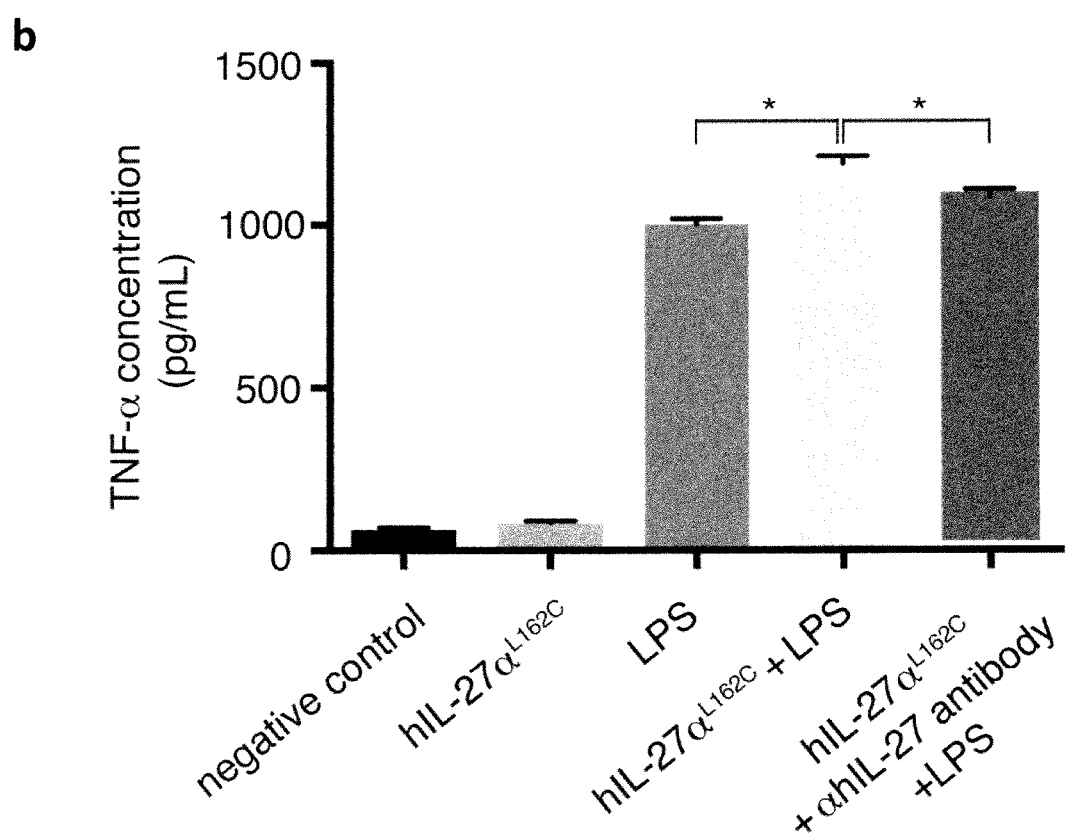

FIG. 9 shows that IL-27α$^{L162C}$ adds a new member to the human cytokine repertoire. FIG. 9(a) shows that hIL-27α$^{L162C}$ increases the secretion of the pro-inflammatory cytokine IL-6 from LPS-stimulated THP-1 macrophages (N=8±SEM, *p<0.05). Effects can be inhibited by an antihuman IL-27 antibody. FIG. 9(b) shows that hIL-27α$^{L162C}$ increases the secretion of the pro-inflammatory cytokine TNF-α from LPS-stimulated (1 µg/mL) THP-1 macrophages (N=6±SEM, *p<0.05). THP-1 macrophages were stimulated with 0.5 µg/mL Expi293-expressed hIL-27α$^{L162C}$ and secreted TNF-α levels were determined using ELISA. Effects are specific, as they can be inhibited by an anti-hIL-27 antibody.

Figure 10:
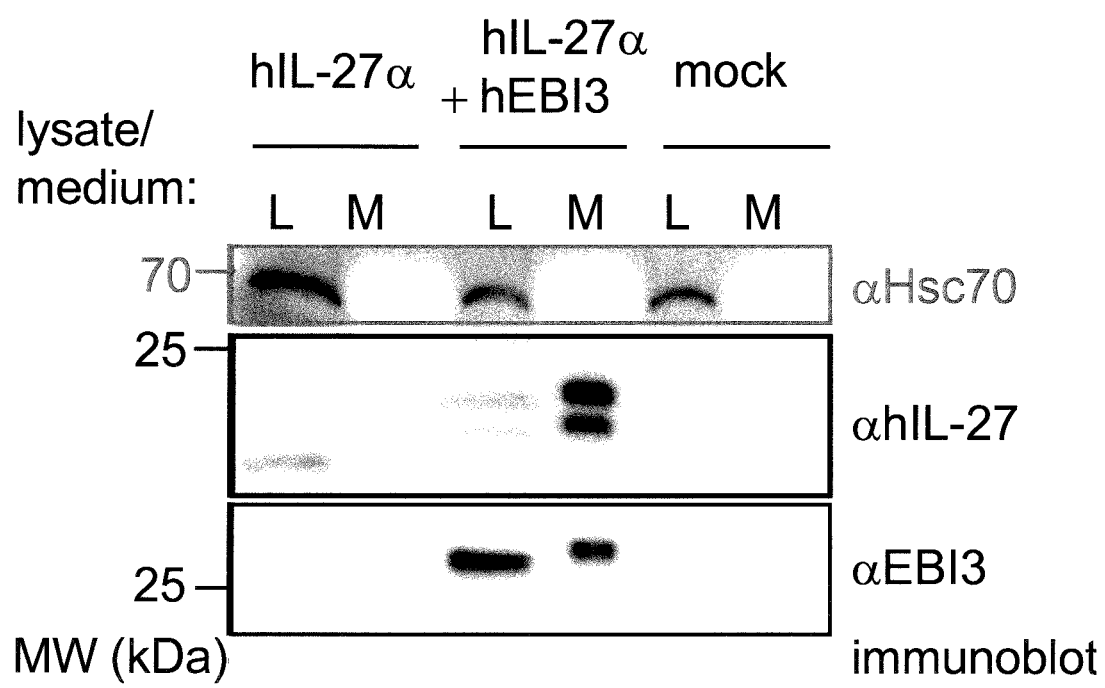
Figure 10:
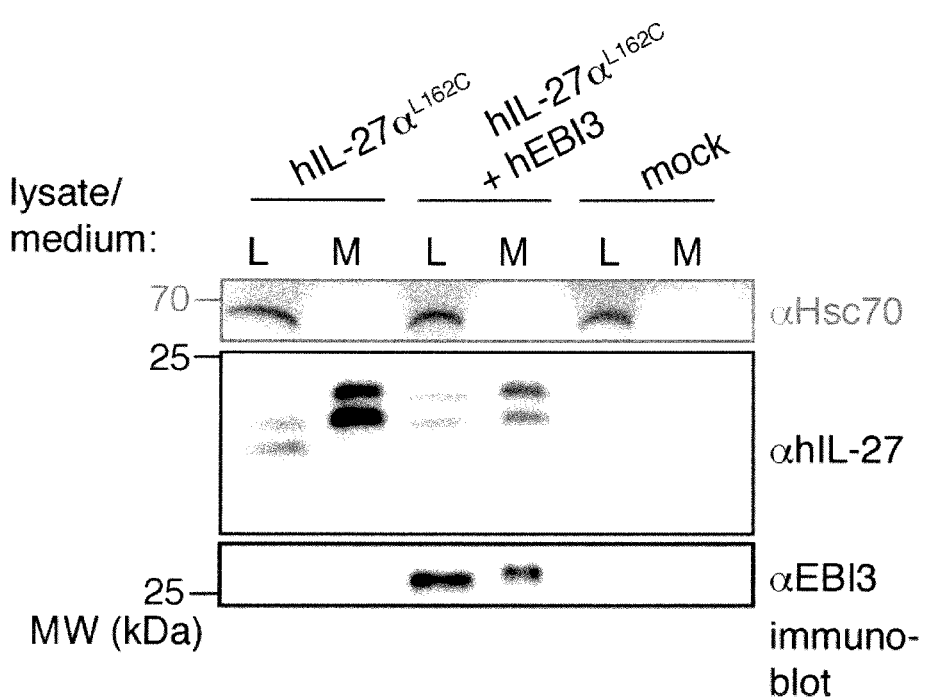

FIG. 10 shows that the presence of an epitope tag does not influence the secretion-competence of the muteins of the present invention. FIG. 10(a) shows that even without a tag human alpha-subunit of Interleukin 27 depends on Ebi3 for secretion. FIG. 10(b) further shows that the mutein hIL-27α$^{L162C}$ (SEQ ID NO: 2) is also secretion-competent without a tag.

FIG. 11 shows the amino acid alignment of human (SEQ ID NO: 9) and mouse beta-subunit of Interleukin 27 (SEQ ID NO: 35), wherein the straight boxes show the cysteines, which are present in human and mouse beta-subunit of Interleukin 27, while the dashed box shows the cysteine, which is present in the mouse beta-subunit of Interleukin 27, but not in the human beta-subunit of Interleukin 27. This reveals that the mouse beta-subunit of Interleukin 27 (SEQ ID NO: 35) has a free cysteine, which is not present in the secretion-competent human beta-subunit of Interleukin 27 (SEQ ID NO: 9).

DETAILED DESCRIPTION OF THE INVENTION

The following language and descriptions of certain preferred embodiments of the present invention are provided in order to further an understanding of the principles of the present invention. However, it will be understood that no limitations of the present invention are intended, and that further alterations, modifications, and applications of the principles of the present invention are also included.

In general, the present invention is directed to a secretion-competent mutein of the α-subunit of human Interleukin 27 (SEQ ID NO: 1), wherein at least one of the amino acid residues of the α-subunit of human Interleukin 27 (SEQ ID NO: 1) selected from the group consisting of sequence positions 160, 161, 162, 163, 164, 165, 180, 181 and 182 is mutated. The present invention also provides a secretion-competent mutein of the α-subunit of human Interleukin 27 (SEQ ID NO: 1), wherein at least one of the amino acid residues of the α-subunit of human Interleukin 27 (SEQ ID NO: 1) selected from the group consisting of sequence positions 160, 161, 162, 163, 180, 181 and 182 is mutated. Further, the present invention also provides these secretion-competent muteins of the α-subunit of human Interleukin 27 (SEQ ID NO: 1) as described herein, wherein the mutein comprises at least 76% sequence identity to the α-subunit of human Interleukin 27 (SEQ ID NO: 1).

Additionally, the present invention is directed to a secretion-competent mutein of the α-subunit of human Interleukin 27 (SEQ ID NO: 1) as described herein, wherein at least one of the amino acid residues at sequence positions 160 to 165 is mutated and/or wherein at least one of the amino acid residues at sequence positions 180 to 182 is mutated. Further, the present invention provides a secretion-competent mutein of the α-subunit of human Interleukin 27 (SEQ ID NO: 1), wherein the mutein comprises at least 76% sequence identity to the α-subunit of human Interleukin 27 (SEQ ID NO: 1) and wherein at least one of the amino acid residues at sequence positions 160 to 165 is mutated and/or wherein at least one of the amino acid residues at sequence positions 180 to 182 is mutated.

In a further aspect, the present invention provides a secretion-competent mutein of the α-subunit of human Interleukin 27 (SEQ ID NO: 1), wherein at least one of the amino acid residues of the α-subunit of human Interleukin 27 (SEQ ID NO: 1) selected from the group consisting of sequence positions 161, 162, 163, 164 and 165 is mutated. In a further aspect, the present invention provides a secretion-competent mutein of the α-subunit of human Interleukin 27 (SEQ ID NO: 1), wherein at least one of the amino acid residues of the α-subunit of human Interleukin 27 (SEQ ID NO: 1) selected from the group consisting of sequence positions 161, 162 and 163 is mutated. Further, the present invention provides a secretion-competent mutein of the α-subunit of human Interleukin 27 (SEQ ID NO: 1), wherein the mutein comprises at least 76% sequence identity to the α-subunit of human Interleukin 27 (SEQ ID NO: 1) and wherein at least one of the amino acid residues of the α-subunit of human Interleukin 27 (SEQ ID NO: 1) selected from the group consisting of sequence positions 161, 162, 163, 164 and 165 is mutated. Further, the present invention provides a secretion-competent mutein of the α-subunit of human Interleukin 27 (SEQ ID NO: 1), wherein the mutein comprises at least 76% sequence identity to the α-subunit of human Interleukin 27 (SEQ ID NO: 1) and wherein at least one of the amino acid residues of the α-subunit of human Interleukin 27 (SEQ ID NO: 1) selected from the group consisting of sequence positions 161, 162 and 163 is/are mutated.

In another aspect, the present invention provides a secretion-competent mutein of the α-subunit of human Interleukin 27 (SEQ ID NO: 1), wherein at least one of the amino acid residues of the α-subunit of human Interleukin 27 (SEQ ID NO: 1) selected from the group consisting of sequence positions 160, 161, 162, 163, 164, 165, 180, 181 and 182 is mutated to cysteine. Further, the present invention provides a secretion-competent mutein of the α-subunit of human Interleukin 27 (SEQ ID NO: 1), wherein the mutein comprises at least 76% sequence identity to the α-subunit of human Interleukin 27 (SEQ ID NO: 1) and wherein at least one of the amino acid residues of the α-subunit of human Interleukin 27 (SEQ ID NO: 1) selected from the group consisting of sequence positions 160, 161, 162, 163, 164, 165, 180, 181 and 182 is mutated to cysteine.

In another aspect, the present invention provides a secretion-competent mutein of the α-subunit of human Interleukin 27 (SEQ ID NO: 1), wherein at least one of the amino acid residues of the α-subunit of human Interleukin 27 (SEQ ID NO: 1) selected from the group consisting of sequence positions 160, 161, 162, 163, 180, 181 and 182 is mutated to cysteine. Further, the present invention provides a secretion-competent mutein of the α-subunit of human Interleukin 27 (SEQ ID NO: 1), wherein the mutein comprises at least 76% sequence identity to the α-subunit of human Interleukin 27 (SEQ ID NO: 1) and wherein at least one of the amino acid residues of the α-subunit of human Interleukin 27 (SEQ ID NO: 1) selected from the group consisting of sequence positions 160, 161, 162, 163, 180, 181 and 182 is mutated to cysteine.

In a further aspect, the present invention provides a secretion-competent mutein of the α-subunit of human Interleukin 27 (SEQ ID NO: 1), wherein at least one of the amino acid residues of the α-subunit of human Interleukin 27 (SEQ ID NO: 1) selected from the group consisting of sequence positions 161, 162, 163, 164 and 165 is mutated to cysteine. The present invention provides a secretion-competent mutein of the α-subunit of human Interleukin 27 (SEQ ID NO: 1), wherein at least one of the amino acid residues of the α-subunit of human Interleukin 27 (SEQ ID NO: 1) selected from the group consisting of sequence positions 161, 162 and 163 is mutated to cysteine. Further, the present invention provides a secretion-competent mutein of the α-subunit of human Interleukin 27 (SEQ ID NO: 1), wherein the mutein comprises at least 76% sequence identity to the α-subunit of human Interleukin 27 (SEQ ID NO: 1) and wherein at least one of the amino acid residues of the α-subunit of human Interleukin 27 (SEQ ID NO: 1) selected from the group consisting of sequence positions 161, 162, 163, 164 and 165 is mutated to cysteine. Further, the present invention provides a secretion-competent mutein of the α-subunit of human Interleukin 27 (SEQ ID NO: 1), wherein the mutein comprises at least 76% sequence identity to the α-subunit of human Interleukin 27 (SEQ ID NO: 1) and wherein at least one of the amino acid residues of the α-subunit of human Interleukin 27 (SEQ ID NO: 1) selected from the group consisting of sequence positions 161, 162 and 163 is mutated to cysteine.

In a further aspect, the present invention provides a secretion-competent mutein of the α-subunit of human Interleukin 27 (SEQ ID NO: 1) comprising an amino acid sequence with at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or even 100% sequence identity to the α-subunit of human Interleukin 27 (SEQ ID NO: 1), wherein in this mutein at least one of the amino acid residues selected from the group consisting of sequence positions 160, 161, 162, 163, 164, 165, 180, 181 and 182 is/are mutated compared to the α-subunit of human Interleukin 27 (SEQ ID NO: 1).

The present invention also provides a secretion-competent mutein of the α-subunit of human Interleukin 27 (SEQ ID NO: 1) comprising an amino acid sequence with at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or even 100% sequence identity to the α-subunit of human Interleukin 27 (SEQ ID NO: 1), wherein in this mutein at least one of the amino acid residues selected from the group consisting of sequence positions 161, 162 and 163 is/are mutated compared to the α-subunit of human Interleukin 27 (SEQ ID NO: 1).

The present invention additionally provides a secretion-competent mutein of the α-subunit of human Interleukin 27 comprising an amino acid sequence with at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or even 100% sequence identity to the α-subunit of human Interleukin 27 (SEQ ID NO: 1), wherein in this mutein at least one of the amino acid residues selected from the group consisting of sequence positions 161, 162, 163, 164 and 165 is/are mutated compared to the α-subunit of human Interleukin 27 (SEQ ID NO: 1).

The present invention additionally provides a secretion-competent mutein of the α-subunit of human Interleukin 27 comprising an amino acid sequence with at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or even 100% sequence identity to the α-subunit of human Interleukin 27 (SEQ ID NO: 1), wherein in this mutein at least one of the amino acid residues selected from the group consisting of sequence positions 161, 162 and 163 is/are mutated compared to the α-subunit of human Interleukin 27 (SEQ ID NO: 1).

In a further aspect, the present invention provides a secretion-competent mutein of the α-subunit of human Interleukin 27 comprising an amino acid sequence with at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or even 100% sequence identity to the α-subunit of human Interleukin 27 (SEQ ID NO: 1), wherein in this mutein at least one of the amino acid residues selected from the group consisting of sequence positions 160, 161, 162, 163, 164, 165, 180, 181 and 182 is mutated to cysteine compared to the α-subunit of human Interleukin 27 (SEQ ID NO: 1).

In a further aspect, the present invention provides a secretion-competent mutein of the α-subunit of human Interleukin 27 comprising an amino acid sequence with at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or even 100% sequence identity to the α-subunit of human Interleukin 27 (SEQ ID NO: 1), wherein in this mutein at least one of the amino acid residues selected from the group consisting of sequence positions 160, 161, 162, 163, 164 and 165 is/are mutated to cysteine compared to the α-subunit of human Interleukin 27 (SEQ ID NO: 1).

The present invention additionally provides a secretion-competent mutein of the α-subunit of human Interleukin 27 comprising an amino acid sequence with at least 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or even 100% sequence identity to the α-subunit of human Interleukin 27 (SEQ ID NO: 1), wherein in this mutein at least one of the amino acid residues selected from the group consisting of sequence positions 161, 162 and 163 is mutated to cysteine compared to the α-subunit of human Interleukin 27 (SEQ ID NO: 1).

It is noted here that the present invention is based on the inventor's analysis of the molecular determinants of IL-27α retention versus secretion. This analysis revealed that the presence or absence of a single Cys residue defines the ability of IL-27α to form an internal disulfide bridge, fold, pass ER quality control and be secreted. The inventors surprisingly found that in the absence of such a single disulfide bridge, IL-27α depends on interaction with its beta-subunit EBI3 for secretion. A single point mutation within IL-27α thus determines assembly-dependent versus autonomous secretion in mouse and man. The present invention structurally and mechanistically reveals the underlying reactions and makes it able to extend the findings to various different species, thus, providing insights into how protein folding influences an organism's cytokine repertoire and immune regulation. Lastly, due to the present invention, it is possible to design an autonomously folding human IL-27 alpha-subunit, which acts as a novel immune modulator. In this context, it is noted that the term "human IL-27 alpha-subunit" or "human IL-27 α-subunit" as used herein refers to the polypeptide sequence of SEQ ID NO: 1 that has been deposited under UniProtKB accession number Q8NEV9. The term "human IL-27 beta-subunit" or "EBI3" as used herein refers to the polypeptide sequence deposited under UniProtKB accession number Q14213 that associates with the human IL-27 alpha-subunit to form the IL-27 Interleukin, a heterodimeric cytokine which functions in innate immunity. The term "mouse IL-27 alpha-subunit" or "mIL-27α" as used herein refers to the polypeptide sequence deposited under genbank indentifier NP 663611.1. The term "mouse IL-27 beta-subunit" or "mEBI3" as used herein refers to the polypeptide sequence deposited under UniProtKB accession number O35228. Accordingly, the term "IL-27" or "Interleukin 27" refers to the heterodimeric cytokine formed by the IL-27 alpha- and IL-27 beta-subunit.

The inventors of the present invention have found that a single cysteine residue toggles IL-27α between being secretion competent in isolation or depending on heterodimerization with EBI3 as a prerequisite to leave the cell. On the other hand, introducing a point mutation into one of the cysteines in mouse IL-27α (SEQ ID NO: 10) renders it dependent on EBI3 for secretion. This establishes a molecular phenocopy of the human IL-27 system for future studies and may also reveal novel functions of IL-27 versus IL-27α. This is important since in mice, deletion of EBI3 will indeed ablate IL-27—but not free IL-27α. In fact, removing its interaction partner EBI3 may potentially even increase levels of free IL-27α with its independent functions. Analogously, deleting IL-27α will ablate IL-27 but also IL-27α functions in mice. It is shown by the inventors of the present invention that this can be circumvented by introducing a single point mutation into one of the cysteines in mouse IL-27α, thus rendering it dependent on EBI3 for secretion as a molecular phenocopy of the human system. Vice versa, by a single point mutant the inventors of the present invention provide a secretion-competent human IL-27α with biological activity on immune cells. The secretion-competent IL-27α according to the present invention, does not block IL-27 function but acts as a cytokine itself. This is of particular relevance since murine IL-27α dampens Graft-versus-Host disease and counteracts sepsis. No good treatment options for these diseases are available yet but interleukins are promising candidates. The muteins of the present invention may provide the basis for new treatment options thereof.

The term "secreting" or "secretion" is used in the present invention in its regular meaning to mean the active export of a protein from a (eukaryotic such as a human) cell into the extracellular environment. Generally secretion occurs through a secretory pathway in the cell, for example, in eukaryotic cells, which involves the endoplasmic reticulum and the golgi apparatus. Accordingly, a mutein according to the present invention is "secretion-competent" or "comprises secretion competence", when the mutein is able to perform a complete passage through the secretory pathway of the cell and through the cytoplasmic membrane. In contrast thereto, the term "non-secretion competent" muteins refers in the present invention to muteins, which are not naturally secreted from the cell into the extracellular environment.

In accordance with the above disclosure, in the mutein of the α-subunit of human Interleukin 27 of the present invention, at least one of the amino acid residues at sequence positions 160 to 163 and/or at least one of the amino acid residues at sequence positions 180 to 182 can be mutated. It is preferred that in accordance with the above disclosure, in the mutein of the α-subunit of human Interleukin 27 of the present invention at least one of the amino acid residues at sequence positions 161 to 163 can be mutated. It is also preferred that in accordance with the above disclosure, in the mutein of the α-subunit of human Interleukin 27 of the present invention at least one of the amino acid residues at sequence positions 180 to 182 can be mutated. This means, a mutein of the present invention can comprise a single mutation at one of these sequence positions but also a mutation at two or more of these sequence positions. The mutation can be any amino acid that renders the mutein secretion-competent, for example, a cysteine residue or a non-natural amino acid that comprises a free thiol group.

In one embodiment of the present invention, in the mutein of the α-subunit of human Interleukin 27 comprising an amino acid sequence with at least 76% sequence identity to the α-subunit of human Interleukin 27 (SEQ ID NO: 1), the amino acid residue at sequence position 160 can be replaced by cysteine.

In another embodiment of the present invention, in the mutein of the α-subunit of human Interleukin 27 comprising an amino acid sequence with at least 76% sequence identity to the α-subunit of human Interleukin 27 (SEQ ID NO: 1), the amino acid residue at sequence position 161 can be replaced by cysteine.

In another embodiment of the present invention, in the mutein of the α-subunit of human Interleukin 27 comprising an amino acid sequence with at least 76% sequence identity to the α-subunit of human Interleukin 27 (SEQ ID NO: 1), the amino acid residue at sequence position 162 can be replaced by cysteine.

In yet another embodiment of the present invention, in the mutein of the α-subunit of human Interleukin 27 comprising an amino acid sequence with at least 76% sequence identity to the α-subunit of human Interleukin 27 (SEQ ID NO: 1), the amino acid residue at sequence position 163 can be replaced by cysteine.

In another embodiment of the present invention, in the mutein of the α-subunit of human Interleukin 27 comprising an amino acid sequence with at least 76% sequence identity to the α-subunit of human Interleukin 27 (SEQ ID NO: 1), the amino acid residue at sequence position 164 can be replaced by cysteine (SEQ ID NO: 33).

In another embodiment of the present invention, in the mutein of the α-subunit of human Interleukin 27 comprising an amino acid sequence with at least 76% sequence identity to the α-subunit of human Interleukin 27 (SEQ ID NO: 1), the amino acid residue at sequence position 165 can be replaced by cysteine (SEQ ID NO: 34).

In still another embodiment of the present invention, in the mutein of the α-subunit of human Interleukin 27 comprising an amino acid sequence with at least 76% sequence identity to the α-subunit of human Interleukin 27 (SEQ ID NO: 1), the amino acid residue at sequence position 180 can be replaced by cysteine.

In a further embodiment of the present invention, in the mutein of the α-subunit of human Interleukin 27 comprising an amino acid sequence with at least 76% sequence identity to the α-subunit of human Interleukin 27 (SEQ ID NO: 1), the amino acid residue at sequence position 181 can be replaced by cysteine.

In yet another embodiment of the present invention, in the mutein of the α-subunit of human Interleukin 27 comprising an amino acid sequence with at least 76% sequence identity to the α-subunit of human Interleukin 27 (SEQ ID NO: 1), the amino acid residue at sequence position 182 can be replaced by cysteine.

In yet another embodiment of the present invention, in the mutein comprising an amino acid sequence with at least 76% sequence identity to the α-subunit of human Interleukin 27 (SEQ ID NO: 1), the amino acid residue at at least one of sequence positions 160, 161, 162, 163, 164, 165, 180, 181 and 182 can be replaced by a non-natural amino acid, such as, but not limited to, selenocysteine or pyrrolysine or by a non-natural amino acid, which builds a covalent bond. In yet another embodiment of the present invention, in the mutein comprising an amino acid sequence with at least 76% sequence identity to the α-subunit of human Interleukin 27 (SEQ ID NO: 1), the amino acid residues at at least two of the sequence positions 160, 161, 162, 163, 164, 165, 180, 181 and 182 can be replaced by equally-charged amino acids, such as, but not limited to, aspartic acid (asp) and glutamic acid (glu) or arginine (arg) and lysine (lys). Thereby, for example, a salt bridge can be build by the mentioned replacements.

The present invention also refers to the muteins as described herein, wherein the mutein further comprises one or more disulfide-bridge(s).

In yet another embodiment of the present invention, in the mutein of the α-subunit of human Interleukin 27 comprising an amino acid sequence with at least 76% sequence identity to the α-subunit of human Interleukin 27 (SEQ ID NO: 1), the amino acid residue at at least one of sequence positions 161, 162, 163, 164 and 165 can be replaced by a non-natural amino acid, such as, but not limited to, selenocysteine or pyrrolysine or by a non-natural amino acid, which builds a covalent bond. In yet another embodiment of the present invention, in the mutein of the α-subunit of human Interleukin 27 comprising an amino acid sequence with at least 76% sequence identity to the α-subunit of human Interleukin 27 (SEQ ID NO: 1), the amino acid residues at at least two of the sequence positions 161, 162, 163, 164 and 165 can be replaced by equally-charged amino acids, such as, but not limited to, aspartic acid (asp) and glutamic acid (glu) or arginine (arg) and lysine (lys). Thereby, for example, a salt bridge can be build by the mentioned replacements.

In line with the above, it is within the scope of the present invention that the above mentioned muteins of the α-subunit of human Interleukin 27 comprising an amino acid sequence with at least 76% sequence identity to the α-subunit of human Interleukin 27 (SEQ ID NO: 1), which are mutated at the amino acid residues 160, 161, 162, 163, 164, 165, 180, 181 and 182 to cysteines, can form muteins with 1, 2, 3, 4, 5, 6 or 7 cysteines at any of the mentioned positions 160, 161, 162, 163, 164, 165, 180, 181 and 182 of the muteins comprising an amino acid sequence with at least 76% sequence identity to the α-subunit of human Interleukin 27 (SEQ ID NO: 1). It is also thus possible that a mutein of the α-subunit of human Interleukin 27 comprising an amino acid sequence with at least 76% sequence identity to the α-subunit of human Interleukin 27 (SEQ ID NO: 1) of the present invention can further comprise one or more disulfide-bridges.

In one embodiment of the present invention, in the mutein of the α-subunit of human Interleukin 27 (SEQ ID NO: 1) of the present invention, the amino acid residue at sequence position 160 can be replaced by cysteine (SEQ ID NO: 3).

In another embodiment of the present invention, in the mutein of the α-subunit of human Interleukin 27 (SEQ ID NO: 1) of the present invention, the amino acid residue at sequence position 161 can be replaced by cysteine (SEQ ID NO: 4).

In another embodiment of the present invention, in the mutein of the α-subunit of human Interleukin 27 (SEQ ID NO: 1) of the present invention, the amino acid residue at sequence position 162 can be replaced by cysteine (SEQ ID NO: 2).

In yet another embodiment of the present invention, in the mutein of the α-subunit of human Interleukin 27 (SEQ ID NO: 1) of the present invention, the amino acid residue at sequence position 163 can be replaced by cysteine (SEQ ID NO: 5).

In another embodiment of the present invention, in the mutein of the α-subunit of human Interleukin 27 (SEQ ID NO: 1) of the present invention, the amino acid residue at sequence position 164 can be replaced by cysteine (SEQ ID NO: 33).

In another embodiment of the present invention, in the mutein of the α-subunit of human Interleukin 27 (SEQ ID NO: 1) of the present invention, the amino acid residue at sequence position 165 can be replaced by cysteine (SEQ ID NO: 34).

In still another embodiment of the present invention, in the mutein of the α-subunit of human Interleukin 27 (SEQ ID NO: 1) of the present invention, the amino acid residue at sequence position 180 can be replaced by cysteine (SEQ ID NO: 6).

In a further embodiment of the present invention, in the mutein of the α-subunit of human Interleukin 27 (SEQ ID NO: 1) of the present invention, the amino acid residue at sequence position 181 can be replaced by cysteine (SEQ ID NO: 7).

In yet another embodiment of the present invention, in the mutein of the α-subunit of human Interleukin 27 (SEQ ID NO: 1) of the present invention, the amino acid residue at sequence position 182 can be replaced by cysteine (SEQ ID NO: 8).

In yet another embodiment of the present invention, in the mutein of the α-subunit of human Interleukin 27 (SEQ ID NO: 1) of the present invention, the amino acid residue at at least one of sequence positions 160, 161, 162, 163, 164, 165, 180, 181 and 182 can be replaced by a non-natural amino acid, such as, but not limited to, selenocysteine or pyrrolysine or by a non-natural amino acid, which builds a covalent bond.

In yet another embodiment of the present invention, in the mutein of the α-subunit of human Interleukin 27 (SEQ ID NO: 1) of the present invention, the mutein further comprises one or more salt bridges. Preferably, wherein the one or more salt bridge is build by replacing at least two of the sequence positions 160, 161, 162, 163, 164, 165, 180, 181 and 182 by equally-charged amino acids, more preferably by replacing two of the sequence positions 160, 161, 162, 163, 164, 165, 180, 181 and 182 by aspartic acid and glutamic acid or arginine and lysine.

In line with the above, it is within the scope of the present invention that the above mentioned mutations of the α-subunit of human Interleukin 27 (SEQ ID NO: 1) at the amino acid residues 160, 161, 162, 163, 164, 165, 180, 181 and 182 to cysteine can form muteins with 1, 2, 3, 4, 5, 6 or 7 cysteines at any of the mentioned positions 160, 161, 162, 163, 164, 165, 180, 181 and 182 of the α-subunit of human Interleukin 27. It is also thus possible that a mutein of the α-subunit of human Interleukin 27 of the present invention can further comprise one or more disulfide-bridges.

In addition or alternatively, the mutein of the α-subunit of human Interleukin 27 of the present invention can further comprise one or more salt bridges that act as structural homologue of the intra-chain disulfide bridge formed, for example, between the naturally occurring cysteine residue present at sequence position 107 of the α-subunit of human Interleukin 27 and a cysteine residue introduced at any of the positions 160, 161, 162, 163, 164, 165, 180, 181 and 182 of the α-subunit of human Interleukin 27. The salt bridge may, for example, arise from the anionic carboxylate (RCOO⁻) group of either aspartic acid or glutamic acid and the cationic ammonium (RNH$_3^+$) from lysine or the guanidinium (RNHC(NH$_2$)$_2^+$) of arginine. Although these are the most common, other residues with ionizable side chains such as histidine, tyrosine, and serine can also participate in the formation of a salt bridge. Thus, muteins of the α-subunit of human Interleukin 27 of the present invention may comprise an amino acid such as aspartic acid or glutamic acid that has a negatively charged side chain moiety under physiological conditions such as aspartic acid or glutamic acid at any of the positions 160, 161, 162, 163, 164, 165, 180, 181 and 182 of the α-subunit of human Interleukin 27 and an amino acid such as lysine or arginine that has a positively charged side chain moiety under physiological conditions at sequence position 107 of the α-subunit of human Interleukin 27.

Alternatively, muteins of the α-subunit of human Interleukin 27 as described herein, also secretion-competent muteins comprising at least 76% sequence identity to the α-subunit of human Interleukin 27 (SEQ ID NO: 1), may comprise an amino acid such as aspartic acid or glutamic acid that has a negatively charged side chain moiety under physiological conditions such as aspartic acid or glutamic acid at sequence position 107 of the α-subunit of human Interleukin 27 and an amino acid such as lysine or arginine that has a positively charged side chain moiety under physiological conditions at any of the positions 160, 161, 162, 163, 164, 165, 180, 181 and 182 of the α-subunit of human Interleukin 27.

The present invention also provides a secretion-competent mutein of human Interleukin 27, comprising an α-subunit p28 and a β-subunit EBI3, wherein the α-subunit is a secretion-competent mutein of the α-subunit of human Interleukin 27 (SEQ ID NO: 1) as described herein. For example, in one embodiment thereof, the α-subunit is a secretion-competent mutein of the α-subunit of human Interleukin 27 comprising at least 76% sequence identity to the α-subunit of human Interleukin 27 (SEQ ID NO: 1) as described herein.

In such a mutein of human Interleukin 27 according to the present invention, at least one of the amino acid residues of the α-subunit of human Interleukin 27 (SEQ ID NO: 1) at sequence positions 160 to 165 can be mutated and/or at least one of the amino acid residues at sequence positions 180 to 182 can be mutated. In such a mutein of human Interleukin 27 according to the present invention, at least one of the amino acid residues of the α-subunit of human Interleukin 27 (SEQ ID NO: 1) at sequence positions 160 to 163 can be mutated and/or at least one of the amino acid residues at sequence positions 180 to 182 can be mutated.

In a further embodiment of the present invention, in such a mutein of human Interleukin 27 of the present invention, at least one of the amino acid residues of the α-subunit of human Interleukin 27 (SEQ ID NO: 1) selected from the group consisting of sequence positions 161, 162, 163, 164 and 165 is/are mutated. In a further embodiment of the present invention, in such a mutein of human Interleukin 27 of the present invention, at least one of the amino acid residues of the α-subunit of human Interleukin 27 (SEQ ID NO: 1) selected from the group consisting of sequence positions 160 to 163 is/are mutated.

In a further embodiment of the present invention, in such a mutein of human Interleukin 27 of the present invention, at least one of the amino acid residues of the α-subunit of human Interleukin 27 (SEQ ID NO: 1) selected from the group consisting of sequence positions 161, 162 and 163 is/are mutated.

In such a mutein of human Interleukin 27 of the present invention, at least one of the amino acid residues of the α-subunit of human Interleukin 27 (SEQ ID NO: 1) selected from the group consisting of sequence positions 160, 161, 162, 163, 164, 165, 180, 181 and 182 is/are mutated to cysteine.

In such a mutein of human Interleukin 27 of the present invention, at least one of the amino acid residues of the α-subunit of human Interleukin 27 (SEQ ID NO: 1) selected from the group consisting of sequence positions 160, 161, 162, 163, 180, 181 and 182 is/are mutated to cysteine.

In a further embodiment of the present invention, in such a mutein of human Interleukin 27 of the present invention, at least one of the amino acid residues of the α-subunit of human Interleukin 27 (SEQ ID NO: 1) selected from the group consisting of sequence positions 161, 162, 163, 164 and 165 is/are mutated to cysteine.

In a further embodiment of the present invention, in such a mutein of human Interleukin 27 of the present invention, at least one of the amino acid residues of the α-subunit of human Interleukin 27 (SEQ ID NO: 1) selected from the group consisting of sequence positions 160 to 163 is/are mutated to cysteine.

In a further embodiment of the present invention, in such a mutein of human Interleukin 27 of the present invention, at least one of the amino acid residues of the α-subunit of human Interleukin 27 (SEQ ID NO: 1) selected from the group consisting of sequence positions 161, 162 and 163 is/are mutated to cysteine.

In such a mutein of human Interleukin 27 of the present invention at least one of the amino acid residues of the α-subunit of human Interleukin 27 (SEQ ID NO: 1) at sequence positions 160 to 165 can be mutated. In another embodiment, such a mutein of human Interleukin 27 of the present invention at least one of the amino acid residues of the α-subunit of human Interleukin 27 (SEQ ID NO: 1) at sequence positions 160 to 163 can be mutated.

Further, in the mutein of human Interleukin 27 of the present invention at least one of the amino acid residues of the α-subunit of human Interleukin 27 (SEQ ID NO: 1) at sequence positions 180 to 182 can be mutated.

In line with the above, in the mutein of human Interleukin 27 of the present invention, the amino acid residue of the α-subunit of human Interleukin 27 (SEQ ID NO: 1) at sequence position 160 can be replaced by cysteine.

In addition or alternatively, in the mutein of human Interleukin 27 of the present invention, the amino acid residue of the α-subunit of human Interleukin 27 (SEQ ID NO: 1) at sequence position 161 can be replaced by cysteine.

In addition or alternatively, in the mutein of human Interleukin 27 of the present invention the amino acid residue of the α-subunit of human Interleukin 27 (SEQ ID NO: 1) at sequence position 162 can be replaced by cysteine (SEQ ID NO: 2).

It is also possible that in the mutein of human Interleukin 27 of the present invention, the amino acid residue of the α-subunit of human Interleukin 27 (SEQ ID NO: 1) at sequence position 163 is replaced by cysteine.

In addition or alternatively, in the mutein of human Interleukin 27 of the present invention the amino acid residue of the α-subunit of human Interleukin 27 (SEQ ID NO: 1) at sequence position 164 can be replaced by cysteine (SEQ ID NO: 33).

In addition or alternatively, in the mutein of human Interleukin 27 of the present invention the amino acid residue of the α-subunit of human Interleukin 27 (SEQ ID NO: 1) at sequence position 165 can be replaced by cysteine (SEQ ID NO: 34).

In yet other embodiments, in the mutein of human Interleukin 27 of the present invention, the amino acid residue of the α-subunit of human Interleukin 27 (SEQ ID NO: 1) at sequence position 180, the amino acid residue of the α-subunit of human Interleukin 27 (SEQ ID NO: 1) at sequence position 181, or the amino acid residue of the α-subunit of human Interleukin 27 (SEQ ID NO: 1) at sequence position 182 can be replaced by cysteine.

In other embodiments of the present invention, in the mutein of human Interleukin 27 of the present invention, at least one of the amino acid residues of the α-subunit of human Interleukin 27 (SEQ ID NO: 1) selected from the group consisting of sequence positions 161, 162, 163, 164 and 165 is mutated to cysteine. In other embodiments of the present invention, in the mutein of human Interleukin 27 of the present invention, at least one of the amino acid residues of the α-subunit of human Interleukin 27 (SEQ ID NO: 1) selected from the group consisting of sequence positions 161, 162 and 163 is mutated to cysteine.

In yet another embodiment, in the mutein of human Interleukin 27 of the present invention the amino acid residue of the α-subunit of human Interleukin 27 (SEQ ID NO: 1) at at least one of sequence positions 160, 161, 162, 163, 164, 165, 180, 181 and 182 can be replaced by a non-natural amino acid, such as, but not limited to, selenocysteine or pyrrolysine or by a non-natural amino acid, which builds a covalent bond. In yet another embodiment of the present invention, in the mutein of human Interleukin 27 of the present invention the amino acid residues of the α-subunit of human Interleukin 27 (SEQ ID NO: 1) at at least two of the sequence positions 160, 161, 162, 163, 164, 165, 180, 181 and 182 can be replaced by equally-charged amino acids, such as, but not limited to, aspartic acid (asp) and glutamic acid (glu) or arginine (arg) and lysine (lys). Thereby, for example, a salt bridge can be build by these mentioned replacements.

In yet another embodiment of the present invention, in the mutein of human Interleukin 27 of the present invention the amino acid residue of the α-subunit of human Interleukin 27 (SEQ ID NO: 1) at at least one of sequence positions 161, 162, 163, 164 and 165 can be replaced by a non-natural amino acid, such as, but not limited to, selenocysteine or pyrrolysine or by a non-natural amino acid, which builds a covalent bond. In yet another embodiment of the present invention, in the mutein of human Interleukin 27 of the present invention the amino acid residues of the α-subunit of human Interleukin 27 (SEQ ID NO: 1) at at least two of the sequence positions 161, 162, 163, 164 and 165 can be replaced by equally-charged amino acids, such as, but not limited to, aspartic acid (asp) and glutamic acid (glu) or arginine (arg) and lysine (lys). Thereby, for example, a salt bridge can be build by these mentioned replacements.

In yet another embodiment of the present invention, in the mutein of human Interleukin 27 of the present invention the amino acid residue of the α-subunit of human Interleukin 27 (SEQ ID NO: 1) at at least one of sequence positions 161, 162 and 163 can be replaced by a non-natural amino acid, such as, but not limited to, selenocysteine or pyrrolysine or by a non-natural amino acid, which builds a covalent bond. In yet another embodiment of the present invention, in the mutein of human Interleukin 27 of the present invention the amino acid residues of the α-subunit of human Interleukin 27 (SEQ ID NO: 1) at at least two of the sequence positions 161, 162 and 163 can be replaced by equally-charged amino acids, such as, but not limited to, aspartic acid (asp) and glutamic acid (glu) or arginine (arg) and lysine (lys). Thereby, for example, a salt bridge can be build by these mentioned replacements.

It is within the scope of the present invention, that the above mentioned mutations of the human Interleukin 27 at the amino acid residues 160, 161, 162, 163, 164, 165, 180, 181 and 182 to cysteine can form muteins with 1, 2, 3, 4, 5, 6 or 7 cysteines at any of the mentioned positions 160, 161, 162, 163, 164, 165, 180, 181 and 182 of human Interleukin 27.

The mutein of human Interleukin 27 of the present invention may thus further comprise one or more disulfide-bridges as explained above. Additionally or alternatively, the mutein of human Interleukin 27 of the present invention can further comprise one or more salt bridges as explained above.

The present invention also provides a nucleic acid molecule comprising a nucleotide sequence encoding the secretion-competent mutein of human Interleukin 27 of the present invention or the secretion-competent mutein of the α-subunit of human Interleukin 27 of the present invention. In an embodiment thereof, the nucleic acid molecule comprises a nucleotide sequence encoding a secretion-competent mutein of the α-subunit of human Interleukin 27 (SEQ ID NO: 1), wherein said secretion-competent mutein comprises at least 76% sequence identity to the α-subunit of human Interleukin 27 (SEQ ID NO: 1).

A nucleic acid molecule according to the present invention may comprise a nucleotide sequence encoding a mutein of SEQ ID NO: 2, SEQ ID NO: 3, SEQ ID NO: 4, SEQ ID NO: 5, SEQ ID NO: 6, SEQ ID NO: 7 or SEQ ID NO: 8.

It is preferred, that the nucleic acid molecule of the present invention is operably linked to a regulatory sequence to allow expression of the nucleic acid molecule. This regulatory sequence may comprise a promoter sequence. The term "promoter" or "promoter sequence" means a DNA sequence which initiates and directs the transcription of a gene into an RNA transcript in cells.

The nucleic acid molecule according to the present invention may be comprised in a vector. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome.

In yet another aspect the invention provides the nucleic acid molecule as described herein for use as a therapeutic agent.

The present invention also provides a host cell containing a nucleic acid molecule of the present invention as described above. A host cell can be any prokaryotic (e.g., *E. coli*) or eukaryotic cell (e.g., insect cells, yeast or mammalian cells).

The present invention also provides an immune modulator comprising a mutein of the present invention. An immune modulator is any protein, substance or composition that is able to carry out immunomodulation, which is the adjustment of the immune response to a desired level, as e.g. in immunopotentiation, immunosuppression, or induction of immunologic tolerance.

The present invention also provides the use of a mutein of the present invention for the manufacture of a medicament for treating a disease in a mammal, preferable a human. Suitable diseases include, but are not limited to, infectious diseases, autoimmune diseases, cancer, transplantation-related diseases, such as Graft-versus-Host-disease, chronic inflammatory diseases, such as chronic inflammatory bowel disease, acute inflammatory diseases, sepsis, septic shock, diabetes or asthma.

The present invention also provides a mutein of the present invention for use as a medicament. Additionally, the present invention also provides a mutein of the present invention for use in the treatment of diseases, including the afore-mentioned infectious diseases, autoimmune diseases, cancer, transplantation-related diseases, such as Graft-versus-Host-disease, chronic inflammatory diseases, such as chronic inflammatory bowel disease, acute inflammatory diseases, sepsis, septic shock, diabetes or asthma.

The present invention also provides a method of treating an Interleukin 27-mediated disease, preferably an infectious disease, an autoimmune disease, cancer, transplantation-related diseases, such as Graft-versus-Host-disease, a chronic inflammatory disease, such as chronic inflammatory bowel disease, acute inflammatory diseases, sepsis, septic shock, diabetes or asthma in a mammal, comprising the step of administering a composition comprising a mutein of the α-subunit of human Interleukin 27 of the present invention or a mutein of human Interleukin 27 of the present invention to a mammal in need thereof. Preferably, the mammal is a human.

The present invention also provides a method for producing a mutein according to the present invention, comprising the steps of:

(a) introducing into a nucleic acid molecule encoding the human Interleukin 27 polypeptide or the human Interleukin 27 α-subunit polypeptide or a polypeptide comprising at least 76% sequence identity to the human Interleukin 27 α-subunit polypeptide a nucleotide sequence mutating at least one amino acid residues of human Interleukin 27 or of the α-subunit of human Interleukin 27 or of a polypeptide comprising at least 76% sequence identity to the human Interleukin 27 α-subunit polypeptide selected from the group consisting of sequence positions 160, 161, 162, 163, 164, 165, 180, 181 and 182, and (b) introducing the obtained nucleic acid molecule for expression into a suitable host cell or into a suitable cell extract or cell lysate.

The present invention also provides a method for producing a mutein according to the present invention, comprising the steps of:

(a) introducing into a nucleic acid molecule encoding the human Interleukin 27 polypeptide or the human Interleukin 27 α-subunit polypeptide a nucleotide sequence mutating at least one amino acid residues of human Interleukin 27 or of the α-subunit of human Interleukin 27 selected from the group consisting of sequence positions 160, 161, 162, 163, 180, 181 and 182, and (b) introducing the obtained nucleic acid molecule for expression into a suitable host cell or into a suitable cell extract or cell lysate.

The present invention also provides a method for producing a mutein according to the present invention, comprising the steps of:

(a) introducing into a nucleic acid molecule encoding the human Interleukin 27 polypeptide or the human Interleukin 27 α-subunit polypeptide a nucleotide sequence mutating at least one amino acid residues of human Interleukin 27 or of the α-subunit of human Interleukin 27 selected from the group consisting of sequence positions 161, 162, and 163, and (b) introducing the obtained nucleic acid molecule for expression into a suitable host cell or into a suitable cell extract or cell lysate.

It is preferred that in the method for producing a mutein according to the present invention, in step (a) into a nucleic acid molecule encoding the human Interleukin 27 polypeptide or the human Interleukin 27 α-subunit polypeptide or the polypeptide comprising at least 76% sequence identity to the human Interleukin 27 α-subunit polypeptide, a nucleotide sequence is introduced mutating at least one of the amino acid residues at sequence positions 160 to 165.

It is preferred that in the method for producing a mutein according to the present invention, in step (a) into a nucleic acid molecule encoding the human Interleukin 27 polypeptide or the human Interleukin 27 α-subunit polypeptide or the polypeptide comprising at least 76% sequence identity to the human Interleukin 27 α-subunit polypeptide, a nucleotide sequence is introduced mutating at least one of the amino acid residues at sequence positions 160 to 163.

It is further preferred that in the method for producing a mutein according to the present invention, in step (a) into a nucleic acid molecule encoding the human Interleukin 27 polypeptide or the human Interleukin 27 α-subunit polypeptide or the polypeptide comprising at least 76% sequence identity to the human Interleukin 27 α-subunit polypeptide, a nucleotide sequence is introduced mutating at least one of the amino acid residues at sequence positions 161 to 163.

It is also preferred that in the method for producing a mutein according to the present invention, in step (a) into a nucleic acid molecule encoding the human Interleukin 27 polypeptide or the human Interleukin 27 α-subunit polypeptide or the polypeptide comprising at least 76% sequence identity to the human Interleukin 27 α-subunit polypeptide, a nucleotide sequence is introduced mutating at least one of the amino acid residues at sequence positions 180 to 182.

In the method for producing a mutein according to the present invention, in step (a) into a nucleic acid molecule encoding the human Interleukin 27 polypeptide or the human Interleukin 27 α-subunit polypeptide or the polypeptide comprising at least 76% sequence identity to the human Interleukin 27 α-subunit polypeptide, a nucleotide sequence can be introduced mutating at least one of the amino acid residues at sequence positions 160 to 165 and/or at sequence positions 180 to 182.

In a preferred embodiment, in the method for producing a mutein according to the present invention, in step (a) into a nucleic acid molecule encoding the human Interleukin 27 polypeptide or the human Interleukin 27 α-subunit polypeptide or the polypeptide comprising at least 76% sequence identity to the human Interleukin 27 α-subunit polypeptide, a nucleotide sequence can be introduced mutating at least one of the amino acid residues at sequence positions 160 to 163.

It is further preferred that in the method for producing a mutein according to the present invention, in step (a) into a nucleic acid molecule encoding the human Interleukin 27 polypeptide or the human Interleukin 27 α-subunit polypeptide or the polypeptide comprising at least 76% sequence identity to the human Interleukin 27 α-subunit polypeptide, a nucleotide sequence is introduced mutating at least one of the amino acid residues at sequence positions 160 to 165 to cysteine.

It is further preferred that in the method for producing a mutein according to the present invention, in step (a) into a nucleic acid molecule encoding the human Interleukin 27 polypeptide or the human Interleukin 27 α-subunit polypeptide or the polypeptide comprising at least 76% sequence identity to the human Interleukin 27 α-subunit polypeptide, a nucleotide sequence is introduced mutating at least one of the amino acid residues at sequence positions 160 to 163 to cysteine.

It is further preferred that in the method for producing a mutein according to the present invention, in step (a) into a nucleic acid molecule encoding the human Interleukin 27 polypeptide or the human Interleukin 27 α-subunit polypeptide or the polypeptide comprising at least 76% sequence identity to the human Interleukin 27 α-subunit polypeptide, a nucleotide sequence is introduced mutating at least one of the amino acid residues at sequence positions 161 to 163 to cysteine.

It is preferred that in the method for producing a mutein according to the present invention, in step (a) into a nucleic acid molecule encoding the human Interleukin 27 polypeptide or the human Interleukin 27 α-subunit polypeptide or the polypeptide comprising at least 76% sequence identity to the human Interleukin 27 α-subunit polypeptide, a nucleotide sequence is introduced mutating at least one of the amino acid residues at sequence positions 180 to 182 to cysteine.

In the method for producing a mutein according to the present invention, in step (a) into a nucleic acid molecule encoding the human Interleukin 27 polypeptide or the human Interleukin 27 α-subunit polypeptide or the polypeptide comprising at least 76% sequence identity to the human Interleukin 27 α-subunit polypeptide, a nucleotide sequence can be introduced mutating at least one of the amino acid residues at sequence positions 160 to 165 and/or at sequence positions 180 to 182 to cysteine. It is further preferred that in the method for producing a mutein according to the present invention, in step (a) into a nucleic acid molecule encoding the human Interleukin 27 polypeptide or the human Interleukin 27 α-subunit polypeptide or the polypeptide comprising at least 76% sequence identity to the human Interleukin 27 α-subunit polypeptide, a nucleotide sequence can be introduced mutating at least one of the amino acid residues at sequence positions 160 to 163 and/or at sequence positions 180 to 182 to cysteine.

It is preferred that in the method for producing a mutein according to the present invention, in step (a) into a nucleic acid molecule encoding the human Interleukin 27 polypeptide or the human Interleukin 27 α-subunit polypeptide or the polypeptide comprising at least 76% sequence identity to the human Interleukin 27 α-subunit polypeptide, a nucleotide sequence is introduced mutating the amino acid residue at sequence position 160 to cysteine.

It is further preferred that in the method for producing a mutein according to the present invention, in step (a) into a nucleic acid molecule encoding the human Interleukin 27 polypeptide or the human Interleukin 27 α-subunit polypeptide or the polypeptide comprising at least 76% sequence identity to the human Interleukin 27 α-subunit polypeptide, a nucleotide sequence is introduced mutating the amino acid residue at sequence position 161 to cysteine.

It is also preferred that in the method for producing a mutein according to the present invention, in step (a) into a nucleic acid molecule encoding the human Interleukin 27 polypeptide or the human Interleukin 27 α-subunit polypeptide or the polypeptide comprising at least 76% sequence identity to the human Interleukin 27 α-subunit polypeptide, a nucleotide sequence is introduced mutating the amino acid residue at sequence position 162 to cysteine.

It is preferred that in the method for producing a mutein according to the present invention, in step (a) into a nucleic acid molecule encoding the human Interleukin 27 polypeptide or the human Interleukin 27 α-subunit polypeptide or the polypeptide comprising at least 76% sequence identity to the human Interleukin 27 α-subunit polypeptide, a nucleotide sequence is introduced mutating the amino acid residue at sequence position 163 to cysteine.

It is preferred that in the method for producing a mutein according to the present invention, in step (a) into a nucleic acid molecule encoding the human Interleukin 27 polypeptide or the human Interleukin 27 α-subunit polypeptide or the polypeptide comprising at least 76% sequence identity to the human Interleukin 27 α-subunit polypeptide, a nucleotide sequence is introduced mutating the amino acid residue at sequence position 164 to cysteine (SEQ ID NO: 33).

It is preferred that in the method for producing a mutein according to the present invention, in step (a) into a nucleic acid molecule encoding the human Interleukin 27 polypeptide or the human Interleukin 27 α-subunit polypeptide or the polypeptide comprising at least 76% sequence identity to the human Interleukin 27 α-subunit polypeptide, a nucleotide sequence is introduced mutating the amino acid residue at sequence position 165 to cysteine (SEQ ID NO: 34).

It is preferred that in the method for producing a mutein according to the present invention, in step (a) into a nucleic acid molecule encoding the human Interleukin 27 polypeptide or the human Interleukin 27 α-subunit polypeptide or the polypeptide comprising at least 76% sequence identity to the human Interleukin 27 α-subunit polypeptide, a nucleotide sequence is introduced mutating the amino acid residue at sequence position 180 to cysteine.

Further, it is preferred that in the method for producing a mutein according to the present invention, in step (a) into a nucleic acid molecule encoding the human Interleukin 27 polypeptide or the human Interleukin 27 α-subunit polypeptide or the polypeptide comprising at least 76% sequence identity to the human Interleukin 27 α-subunit polypeptide, a nucleotide sequence is introduced mutating the amino acid residue at sequence position 181 to cysteine.

It is also preferred that in the method for producing a mutein according to the present invention, in step (a) into a nucleic acid molecule encoding the human Interleukin 27 polypeptide or the human Interleukin 27 α-subunit polypeptide or the polypeptide comprising at least 76% sequence identity to the human Interleukin 27 α-subunit polypeptide, a nucleotide sequence is introduced mutating the amino acid residue at sequence position 182 to cysteine.

In yet another embodiment, in the method for producing a mutein according to the present invention, in step (a) into a nucleic acid molecule encoding the human Interleukin 27 polypeptide or the human Interleukin 27 α-subunit polypeptide or the polypeptide comprising at least 76% sequence identity to the human Interleukin 27 α-subunit polypeptide, a nucleotide sequence is introduced mutating the amino acid residue at at least one of sequence positions 160, 161, 162, 163, 164, 165, 180, 181 and 182 to a non-natural amino acid, such as, but not limited to, selenocysteine or pyrrolysine or by a non-natural amino acid, which builds a covalent bond. In yet another embodiment of the present invention, in the method for producing a mutein according to the present invention, in step (a) into a nucleic acid molecule encoding the human Interleukin 27 polypeptide or the human Interleukin 27 α-subunit polypeptide or the polypeptide comprising at least 76% sequence identity to the human Interleukin 27 α-subunit polypeptide, a nucleotide sequence is introduced replacing at at least two of the sequence positions 161, 162, 163, 164 and 165 by equally-charged amino acids, such as, but not limited to, aspartic acid (asp) and glutamic acid (glu) or arginine (arg) and lysine (lys). Thereby, for example, a salt bridge can be build by the mentioned replacements. In yet another embodiment of the present invention, in the method for producing a mutein according to the present invention, in step (a) into a nucleic acid molecule encoding the human Interleukin 27 polypeptide or the human Interleukin 27 α-subunit polypeptide or the polypeptide comprising at least 76% sequence identity to the human Interleukin 27 α-subunit polypeptide, a nucleotide sequence is introduced replacing at at least two of the sequence positions 161, 162 and 163 by equally-charged amino acids, such as, but not limited to, aspartic acid (asp) and glutamic acid (glu) or arginine (arg) and lysine (lys). Thereby, for example, a salt bridge can be build by the mentioned replacements.

The present invention also comprises that in the method for producing a mutein according to the present invention, in step (a) into a nucleic acid molecule encoding the human Interleukin 27 polypeptide or the human Interleukin 27 α-subunit polypeptide or the polypeptide comprising at least 76% sequence identity to the human Interleukin 27 α-subunit polypeptide, a nucleotide sequence is introduced mutating 1, 2, 3, 4, 5, 6 or even all 7 of the amino acid residues at sequence positions 160, 161, 162, 163, 164, 165, 180, 181 and 182 to cysteine.

The present invention also comprises that in the method for producing a mutein according to the present invention, in step (a) into a nucleic acid molecule encoding the human Interleukin 27 polypeptide or the human Interleukin 27 α-subunit polypeptide or the polypeptide comprising at least 76% sequence identity to the human Interleukin 27 α-subunit polypeptide, a nucleotide sequence is introduced mutating 1, 2, 3, 4, 5, 6 or even all 7 of the amino acid residues at sequence positions 160, 161, 162, 163, 180, 181 and 182 to cysteine.

The present invention also comprises that in the method for producing a mutein according to the present invention, in step (a) into a nucleic acid molecule encoding the human Interleukin 27 polypeptide or the human Interleukin 27 α-subunit polypeptide or the polypeptide comprising at least 76% sequence identity to the human Interleukin 27 α-subunit polypeptide, a nucleotide sequence is introduced mutating 1, 2, 3, 4, 5, 6 or even all 7 of the amino acid residues at sequence positions 160, 161, 162, 163, 164 and 165 to cysteine.

The present invention also comprises that in the method for producing a mutein according to the present invention, in step (a) into a nucleic acid molecule encoding the human Interleukin 27 polypeptide or the human Interleukin 27 α-subunit polypeptide or the polypeptide comprising at least 76% sequence identity to the human Interleukin 27 α-subunit polypeptide, a nucleotide sequence is introduced mutating 1, 2, 3, 4, 5, 6 or even all 7 of the amino acid residues at sequence positions 161, 162 and 163 to cysteine.

The present invention also provides a secretion-incompetent mutein of the α-subunit of mouse Interleukin 27 (SEQ ID NO: 10), wherein at least one of the two cysteines at amino acid positions 103 and 158 is/are mutated (i.e. replaced by another amino acid) or deleted. In this embodiment "secretion-incompetent" means that the secretion of this specific mutein of the α-subunit of mouse Interleukin 27 (SEQ ID NO: 10) depends on the presence of the beta-subunit EBI3. This secretion-dependent mutein of the α-subunit of mouse Interleukin 27 (SEQ ID NO: 10) thus behaves like the human α-subunit of Interleukin 27 (SEQ ID NO: 1). In a preferred embodiment, in the secretion-incompetent mutein of the α-subunit of mouse Interleukin 27 (SEQ ID NO: 10) at least one of the two cysteine residues at amino acid positions 103 and 158 is replaced by a hydrophobic amino acid residue. In a further preferred embodiment, in the secretion-incompetent mutein of the α-subunit of mouse Interleukin 27 (SEQ ID NO: 10) at least one of the two cysteines at amino acid positions 103 and 158 (SEQ ID NO: 29) is/are mutated to leucine or serine, or alanine. In this connection, it is noted that the α-subunit of mouse Interleukin 27 (SEQ ID NO: 10) has an amino acid length of 234 residues, while the α-subunit of human Interleukin 27 (SEQ ID NO: 1) has an amino acid length of 243 residues. The sequence identity between the SEQ ID NO: 1 and the SEQ ID NO: 10 has been determined as being 75%.

By "identity" or "sequence identity" is meant a property of sequences that measures their similarity or relationship. The term "sequence identity" or "identity" as used in the present invention means the percentage of pair-wise identical residues—following (homology) alignment of a sequence of a polypeptide of the invention with a sequence in question—with respect to the number of residues in the longer of these two sequences. Identity is measured by dividing the number of identical residues by the total number of residues and multiplying the product by 100.

The percentage of sequence homology or sequence identity can, for example, be determined herein using the program BLASTP, version blastp 2.2.5 (Nov. 16, 2002; cf. Altschul, S. F. et al. (1997) *Nucl. Acids Res.* 25, 3389-3402). In this embodiment the percentage of homology is based on the alignment of the entire polypeptide sequences (matrix: BLOSUM 62; gap costs: 11.1; cutoff value set to $10^{-3}$) including the respective sequences. It is calculated as the percentage of numbers of "positives" (homologous amino acids) indicated as result in the BLASTP program output divided by the total number of amino acids selected by the program for the alignment.

The present invention reveals that the secretion of IL-27α and thus potential immune regulation by this subunit depend on a single Cys residue for mouse and man. It could be shown by the inventors of the present invention that this characteristic was conserved in other species, including model organisms like pig and monkey. Although different cysteine configurations existed for different species, the inventors of the present invention observed complete agreement with this hypothesis for all species tested.

Whenever a disulfide bond was present in IL-27α it was secretion-competent in isolation. Otherwise its secretion was dependent on EBI3. In line with these findings, the inventors of the present invention replaced the second cysteine in mIL-27α by a leucine (C158L), so that mIL-27$\alpha^{C158L}$ was now retained in cells in isolation and its secretion was induced by EBI3, just like its human counterpart.

In another aspect, the present invention also provides a secretion-competent mutein of the beta-subunit of mouse Interleukin 27 (SEQ ID NO: 35), wherein the amino acid residue at amino acid position 198 is mutated or deleted. It is preferred in this embodiment that a secretion-competent mutein of the beta-subunit of mouse Interleukin 27 (SEQ ID NO: 36) is provided, wherein the amino acid residue at amino acid position 198 is/are replaced by tyrosine. In this connection, it has to be considered that the human beta-subunit of Interleukin 27 can be secreted alone. However, naturally, the mouse beta-subunit of Interleukin 27 is secretion-incompetent[44]. The inventors of the present invention have however discovered that due to the mutations as described herein the mouse beta-subunit of Interleukin 27 becomes secretion-competent.

In a further aspect, the present invention also provides a mutein of mouse Interleukin 27, comprising an α-subunit p28 and a β-subunit EBI3, wherein the α-subunit is a secretion-incompetent mutein of the α-subunit of mouse Interleukin 27 (SEQ ID NO: 10) as described herein and/or wherein the β-subunit is a secretion-competent mutein of the β-subunit of mouse Interleukin 27 (SEQ ID NO: 35) as described herein.

The invention is further illustrated by the following experimental Examples.

EXAMPLES

Constructs for Mammalian Expression:

Interleukin cDNAs were obtained from (hIL-27α and hEBI3) or GeneArt (mIL-27α, Thermo Fisher Scientific) and cloned into the pSVL vector (Amersham) for mammalian expression. hIL-27α (SEQ ID NO: 1), mIL-27α (SEQ ID NO: 10) and hEBI3 (SEQ ID NO: 9) amino acid sequences correspond to the UniProt accession numbers Q8NEV9, Q8K3I6, and Q14213, respectively. For a species comparison of IL-27α, sequences corresponding to genbank indentifiers NP_001158125.1 (*Bos taurus*) (SEQ ID NO: 11), XP_012398754.1 (*Sarcophilus harrisii*) (SEQ ID NO: 12), and XP_008683452.1 (*Ursus maritimus*) (SEQ ID NO: 13) were additionally synthesized by Geneart (Thermo Fisher Scientific) with optimized codon-usage for human expression. Where indicated, a (GS)$_4$-linker followed by a V5 tag was introduced at the C-terminus of the different IL-27α constructs. Mutants were generated by site-directed mutagenesis. Constructs for BiP expression have been described previously[32]. All constructs were sequenced.

Cell Culture and Transient Transfections:

HEK293T cells were grown in Dulbecco's modified Eagle's medium (DMEM) containing L-Ala-L-Gln (AQmedia, Sigma-Aldrich) supplemented with 10% (v/v) fetal bovine serum (Biochrom) at 37° C. and 5% $CO_2$. The medium was complemented with a 1% (v/v) antibiotic-antimycotic solution (25 µg/ml amphotenicin B, 10 mg/ml streptomycin, and 10,000 units of penicillin; Sigma-Aldrich) (complete DMEM). Transient transfections were carried out for 24 h in either p35 poly D-lysine coated dishes (Becton Dickinson) or p60 dishes (Techno Plastic Products) using GeneCellin (BioCellChallenge) according to the manufacturer's protocol. Equal amounts of constructs or empty vector were transfected with a total DNA amount of 3 µg (p35) or 6 µg (p60). For BiP interaction studies, a 3:1 ratio of α subunit over chaperone DNA was used.

Secretion and Redox Experiments:

For secretion and redox-status experiments by immunoblotting cells were transfected for 8 h, washed twice with PBS and then supplemented with 0.5 ml (p35) or 2 ml (p60) fresh medium for another 16 h. Prior to lysis, cells were washed twice in ice cold PBS, supplemented with 20 mM NEM if samples were to be run on non-reducing SDS-PAGE gels. Cell lysis was carried out in RIPA buffer (50 mM Tris/HCl, pH 7.5, 150 mM NaCl, 1.0% Nonidet P40 substitute, 0.5% sodium deoxycholate, 0.1% SDS, 1x Roche complete Protease Inhibitor w/o EDTA; Roche Diagnostics). 20 mM NEM was added to the lysis buffer for non-reducing SDS-PAGE gels. To analyze secreted proteins, the medium was centrifuged for 5 min, 300 g, 4° C. Subsequently, samples were supplemented with 0.1 volumes of 500 mM Tris/HCl, pH 7.5, 1.5 M NaCl (and 200 mM NEM in the case of non-reducing SDS-PAGE) and protease inhibitor and centrifuged for 15 min, 20.000 g, 4° C. Samples were supplemented with 0.2 volumes of 5x Laemmli containing either β-mercaptoethanol for reducing SDS-PAGE or 100 mM NEM for non-reducing SDS-PAGE. Endo H/PNGase F/O-glycosidase (New England Biolabs) deglycosylation experiments were carried out according to the protocols of the manufacturer.

Immunoblots and Immunoprecipitation Experiments:

For immunoblots, samples were run on 12% SDS-PAGE gels, transferred to PVDF membranes and blotted with anti-Hsc70 (Santa Cruz, sc-1059 or sc-7298, 1:1,000 in gelatin buffer (0.1% gelatin, 15 mM Tris/HCl, pH 7.5, 130 mM NaCl, 1 mM EDTA, 0.1% Triton X-100, 0.002% NaN3)), anti-V5 (Thermo Fisher Scientific, MA5-15253, 1:1,000 in TBS, 0.05% Tween, 5% milk) or anti-hIL-27 antibodies (R&D Systems, AF2526, 1:200 in TBS, 0.05% Tween, 5% milk). Anti-EBI3 and anti-BiP antisera have been described previously[33,34]. Species-specific HRP-conjugated secondary antibodies (in TBS, 0.05% Tween, 5% milk or gelatin buffer) were used (Santa Cruz). Blots were detected using Amersham ECL prime (GE Healthcare) and a Fusion Pulse 6 imager (Vilber Lourmat). Immunoprecipitations were performed using the same antibodies as for immunoblotting with suitable isotype controls (purified mouse IgG1, κ isotype control, BioLegend). After PBS-washing cells were lysed with NP40 lysis buffer (50 mM Tris/HCl, pH 7.5, 150 mM NaCl, 0.5% NP40, 0.5% DOC, 1x Roche complete Protease Inhibitor w/o EDTA; Roche Diagnostics) and centrifugation-cleared lysates (15 min, 20.000 g, 4° C.) incubated rotating o/n at 4° C. with 2 µg target-specific antibody or isotype control. For co-immunoprecipitation of BiP, the lysis buffer was supplemented with 10 U/ml apyrase (Sigma Aldrich) and 20 mM NEM. After addition of 25 µl Protein A/G agarose (Santa Cruz) for 1 h, beads were washed three times with NP40-wash buffer (50 mM Tris/HCl pH 7.5, 400 mM NaCl, 0.5% NP40, 0.5% DOC) and proteins were eluted by boiling in 2xLaemmli buffer containing β-mercaptoethanol for reducing SDS-PAGE. For immunoprecipitations of secreted proteins, the medium was treated as described for the analysis of secreted protein, precleared for 1 h with 30 µl Protein A/G agarose (Santa Cruz) and subsequently treated like the lysate, using 2.5 µg of antibody.

Recombinant Protein Production.

Human IL-27α cDNA optimized for expression in *E. coli* (without ER-import sequence) was obtained from GeneArt (Thermo Fisher Scientific) and cloned into the pET21a vector (Merck Millipore) with an N-terminal hexa-Histidine-tag and TEV protease cleavage site after the tag. The L162C mutation was introduced by site-directed mutagenesis. Proteins were expressed as inclusion bodies in selective LB medium. The culture was induced at $OD_{600}$=0.6 with 1 mM IPTG and harvested after another 4 h by centrifugation (5.000 rpm, 15 min, 4° C.). To isolate inclusion bodies, cells were lysed by sonication on ice in 100 mM Tris/HCl, pH 7.5, 100 mM NaCl, 5 mM EDTA, SigmaFAST protease inhibitor and subsequently spun down (20.000 g, 20 min, 4° C.). The cell pellet was resuspended, washed twice with 100 mM Tris/HCl, pH 7.5, 500 mM NaCl, 5 mM EDTA, 1.0% Triton X-100, and finally once with 100 mM Tris/HCl, pH 7.5, 100 mM NaCl. Inclusion bodies were solubilized in 50 mM sodium phosphate, pH 7.5, 250 mM NaCl, 6 M GdmCl and 10 mM β-mercaptoethanol at 4° C. After o/n solubilization, the solution was cleared by centrifugation (20.000 g, 20 min, 20° C.). The supernatant was diluted with 1 volume of 50 mM sodium phosphate, pH 7.5, 250 mM NaCl, 5 M GdmCl and applied to Ni-Sepharose HP column (GE Healthcare). Bound protein was washed with 50 mM sodium phosphate, pH 7.5, 250 mM NaCl, 5 M GdmCl, 30 mM imidazole, 1 mM DTT and eluted with 50 mM sodium phosphate, pH 3.5, 250 mM NaCl, 5 M GdmCl and 1 mM DTT. Eluted protein was further purified and buffer exchanged into 50 mM MES pH 6.0, 6 M urea, 1 mM EDTA by size exclusion chromatography using a HiPrep 16/60 Sephacryl S-400 HR column (GE Healthcare). Protein concentrations were determined spectrophotometrically using $A_{280\ nm}$.Human IL-27$\alpha^{L162C}$ cDNA optimized for expression in *H. sapiens* was obtained from GeneArt (Thermo Fisher Scientific) and cloned into the pHEK293 Ultra Expression Vector I (TaKaRa Clontech) for mammalian cell expression. Protein expression was carried out with the Expi293 expression system according to the manufacturer's protocol (Thermo Fisher Scientific). 48 h post-transfection, the medium was harvested by centrifugation (300 g, 15 min, 4° C.), concentrated to 1.8 to 6.2 µg/mL using Amicon Ultra-15, PLBC Ultracel-PL membrane, 3 kDa (Sigma-Aldrich) and used for immunological assays. hIL-27$\alpha^{L156C}$ His$_6$ purified from inclusion bodies in *E. coli* was used as a reference to obtain a standard curve with linear fit for quantification of hIL-27$\alpha^{L162C}$ in Expi293 supernatants using Western blot signals.

Quantification and Statistics:

Western blots were quantified using the Bio-1D software (Vilber Lourmat). Western blot signals of co-immunoprecipitated BiP were normalized for BiP expression levels by dividing by the respective BiP input signals. BiP binding was determined by dividing the normalized BiP signal by the signal of immunoprecipitated α-subunit. Statistical analyses were performed using GraphPad, version 6.0 (GraphPad Software). Where indicated, data were analyzed with two-tailed, unpaired Student's t-tests. Differences were considered statistically significant with p<0.05. Where no statistical data are shown, all experiments were performed at least three times, and one representative experiment was selected.

Sequence Analysis and Homology Modeling:

Multiple DNA sequence alignments were performed using Clustal Omega[35]. For a species comparison of IL-27α, additionally, sequences corresponding to genbank indentifiers XP_004268682.1 (*Orcinus orca*) (SEQ ID NO: 14), XP_018867076.1 (*Gorilla gorilla gorilla*) (SEQ ID NO: 15), XP_012398754.1 (*Criteculus griseus*) (SEQ ID NO: 16), XP_001496678.1 (*Equus caballus*) (SEQ ID NO: 17), EHH31550.1 (*Macaca mulatta*) (SEQ ID NO: 18), NP_001007521.1 (*Sus scrofa*) (SEQ ID NO: 19), XP_017198096.1 (*Oryctolagus cuniculus*) (SEQ ID NO: 20), XP_344963.5 (*Rattus norvegicus*) (SEQ ID NO: 21), XP_007894866.1 (*Callorhinchus milii*) (SEQ ID NO: 22) and XP_014457024.1 (*Alligator mississippiensis*) (SEQ ID NO: 23) were used. iTasser[36] was used for homology modeling of human and murine IL-27α structures. Structural alignments were generated using Yasara Structure (www.yasara.org).

Molecular Dynamics Simulations.

Comparative Molecular Dynamics (MD) simulations were performed starting from the human wt hIL-27α and hIL-27$\alpha^{L162C}$ model structures, respectively, including a disulfide bond between L162C and C107 in the case of hIL-27$\alpha^{L162C}$. All MD simulations and the analysis of root-mean square deviation (RMSD) and fluctuations (RMSF) were performed using the Amber14 package[37] and the parm14SB force field[38]. Proteins were first solvated in octahedral boxes including explicit Na$^+$ and Cl$^-$ ions (~0.15 M) and explicit (TIP3P) water molecules[39] keeping a minimum distance of 10 Å between any protein atom and the box boundary. The simulation systems were first energy minimized (5000 steps) followed by heating up to 300 K in steps of 100 K with position restraints on all non-hydrogen atoms of the proteins. Subsequently, positional restraints were gradually removed from an initial 12 kcal·mol$^{-1}$·Å$^{-2}$ to 0.5 kcal·mol$^{-1}$·Å$^{-2}$ within 0.5 ns followed by a 1 ns unrestrained equilibration phase at 310 K. All production simulations (200 ns) were performed at a temperature of 310 K and a pressure of 1 bar.

It is clear from the homology modeling and subsequent molecular dynamics simulations that a disulfide bridge between two cysteine residues can be formed, when at least one of the amino acid residues at the positions 160, 161, 162, 163, 164, 165, 180, 181 and 182 of the α-subunit of human Interleukin 27 or of human Interleukin 27 is mutated to cysteine. Such a disulfide bridge can then be formed between any of the mentioned positions 160, 161, 162, 163, 164, 165, 180, 181 and 182 and the cysteine at the amino acid position 107 of the α-subunit of human Interleukin 27 (SEQ ID NO: 1). Alternatively, it is also possible that instead of a disulfide bridge a salt bridge as defined herein can be formed between an amino acid residue present at sequence position 107 that have a charged side chain (under physiological conditions) with an amino acid residue that is present at any of the sequence positions 160, 161, 162, 163, 164, 165, 180, 181 and 182 and that has a charged side chain of opposite charge under physiological conditions.

IL-27 Cytokine and Macrophage Assays.

THP-1 cells were grown in RPMI-1640 medium containing L-Ala-L-Gln (AQmedia, Sigma-Aldrich) supplemented with 10% (v/v) fetal bovine serum (Biochrom) at 37° C. and 5% $CO_2$. The medium was complemented with a 1% (v/v) antibiotic-antimycotic solution (25 µg/ml amphotericin B, 10 mg/ml streptomycin, and 10,000 units of penicillin; Sigma-Aldrich) (complete RPMI-1640). THP-1 cells were seeded at a density of $2\times10^5$ cells/mL in 0.5 mL and differentiated to macrophages by incubation with 25 nM PMA for 48 h (Lund et al., 2016). Subsequently, the medium was exchanged against PMA-free complete RPMI-1640. After 24 h, the cells were pre-incubated for 2 h with 0.5 µg/mL of Expi293 expressed hIL-27$\alpha^{L162C}$/control medium and then stimulated for another 4 h with 1 µg/mL LPS in the presence of hIL-27$\alpha^{L162C}$/control medium. Cell supernatants were harvested by centrifugation (300 g, 15 min, 4° C.). As a control, hIL-27$\alpha^{L162C}$ was pre-mixed with anti-IL-27 antibody (R&D Systems, AF2526; final concentration: 10 µg/mL) and added to the cells. IL-6 and TNF-α levels in the macrophage supernatant were determined using human IL-6 or human TNF-α DuoSet ELISA kits following the manufacturer's instructions (R&D systems). Duplicates of each biological replicate were measured and cytokine concentrations were determined using standard curves analyzed with a linear fit.

Example 1: The Present Invention Shows that a Single Point Mutation Renders Human IL-27α Secretion-Competent in Isolation The alpha and beta subunit (IL-27α/p28 and EBI3, respectively) of IL-27 can assemble non-covalently to form the bioactive heterodimeric IL-27. IL-27 signals via the heterodimeric IL-27Rα(WSX-1)/gp130 receptor[4,18] (see FIG. 2(a)). So far, human IL-27α (hIL-27α) retains in isolation in transfected 293T cells and co-expression of its β-subunit, hEBI3 (SEQ ID NO: 9), induces its secretion (see FIG. 2(b)).

The inventors used hIL-27α with a C-terminal V5-epitope tag, separated by a flexible GS-linker, which together introduced a C-terminal O-glycosylation site into hIL-27α (see FIG. 2(c)). Since O-gylcosylation occurs in the Golgi and the inventors did not observe any modification of this site in hIL-27α in the absence of hEBI3 (see FIG. 2(b)), hIL-27α (SEQ ID NO: 1) appears to be retained in the ER in the absence of hEBI3 (SEQ ID NO: 9).

In contrast to the human IL-27alpha subunit, its mouse ortholog (mIL-27α, SEQ ID NO: 10) can be secreted in isolation (see FIG. 2(d))[4]. Of note, human EBI3 (hEBI3) (SEQ ID NO: 9) also further increased the secretion of mIL-27α (SEQ ID NO: 10) (see FIG. 2(d)), which proofs of a conserved IL-27 interface between mouse and man. In agreement with this, the interaction between the two subunits, mIL-27α (SEQ ID NO: 10) and hEBI3 (SEQ ID NO: 9), was detected by co-immunoprecipitation experiments.

The difference in secretion between human and mouse IL-27α is intriguing, in particular since immunomodulatory functions have been attributed to the mouse ortholog[17]. To identify differences between the two proteins that may cause this distinct behavior the inventors have compared their primary sequences. This sequence alignment revealed several striking differences between two otherwise highly conserved sequences of human and mouse IL-27α (see FIG. 3(a)):

First, mIL-27α (SEQ ID NO: 10) possesses a predicted N-glycosylation site, whereas its human ortholog does not, which is in agreement with our deglycosylation data (see FIG. 2(c)).

Second, two cysteines are found in the sequence of mIL-27α (SEQ ID NO: 10) (positions 103 and 158), whereas only one is found in hIL-27α (position 107).

And third, a poly-glutamate stretch in IL-27α, which has been associated with its localization to bone structures[19], is interrupted by a lysine in mIL-27α (SEQ ID NO: 10), but not in hIL-27α (SEQ ID NO: 1).

To assess the impact of these sequence differences, the inventors individually introduced corresponding mutations into hIL-27α (D89N (SEQ ID NO: 31), L162C (SEQ ID NO: 2) and K168 insertion (SEQ ID NO: 32), respectively) and monitored secretion of the mutant proteins in isolation. As expected to occur upon N-glycosylation, hIL-27α$^{D189N}$ (SEQ ID NO: 31) now shifted upwards in molecular weight. However, no secretion was observed for this mutant, and neither was hIL-27α$^{K168\ insertion}$ (SEQ ID NO: 32) secreted (see FIG. 3(b)). In striking contrast, hIL-27α$^{L162C}$(SEQ ID NO: 2) was now almost exclusively found in the media and became O-glycosylated, arguing for bona fide secretion (see FIG. 3(b)). Thus, it was surprisingly found by the inventors of the present invention that a single point mutation renders hIL-27α secretion-competent in isolation.

To understand this effect in more detail, the inventors modeled the structures of human and mouse IL-27α. Both showed 4-helical bundle structures that were superimposable with an RMSD of only 1.0 Å (see FIGS. 3(c) and (d)). Of note, within this structure the two cysteines in mouse IL-27α were in proximity and could thus form a disulfide bridge connecting the second helix of the 4-helical bundle fold with the N-terminal part of the unique poly-glutamate stretch that separates helices 3 and 4 in IL-27α (see FIG. 3(c)). To assess disulfide bridge formation in the different proteins, the inventors compared the mobility of the secreted proteins on non-reducing and reducing SDS-PAGE gels[20]. Even though no mobility shift was observed for mIL-27α (SEQ ID NO: 10), they observed a clear mobility shift for hIL-27α$^{L162C}$(SEQ ID NO: 2) under reducing versus non-reducing conditions, which was not observed for wild type (wt) hIL-27α (SEQ ID NO: 1). This shows formation of a disulfide bridge in hIL-27α$^{L162C}$ (SEQ ID NO: 2) and renders it secretion-competent in isolation.

Example 2: Assessing Molecular Determinants of Human IL-27α Retention Versus Secretion As hIL-27α (SEQ ID NO: 1) is retained in the cell when expressed in isolation and can only be secreted upon co-expression of its beta subunit EBI3 (SEQ ID NO: 9)(see FIG. 2(b)), the inventors investigated what led to retention of hIL-27α (SEQ ID NO: 1) in absence of EBI3 and why it is dependent on forming a disulfide bridge for secretion. The inventors first mutated different structural elements in hIL-27α that may be involved in its folding and retention, beginning with its free cysteine (C107, SEQ ID NO: 28, see FIG. 4(a)). Thiol-based retention of free cysteines mediated by ERp44 constitutes an important step in e.g. IgM protein quality control[21] and this single free cysteine could e.g. become inaccessible upon heterodimerization with EBI3. However, like wt hIL-27α (SEQ ID NO: 1), isolated hIL-27α$^{C107L}$ (SEQ ID NO: 28) was retained in the cell but was secreted upon co-expression of EBI3 (see FIG. 4(a)). Recognition of its free thiol thus does not account for hIL-27α retention and C107 is dispensable for assembly-induced secretion of hIL-27α (SEQ ID NO: 1) by EBI3.

Figure 3:
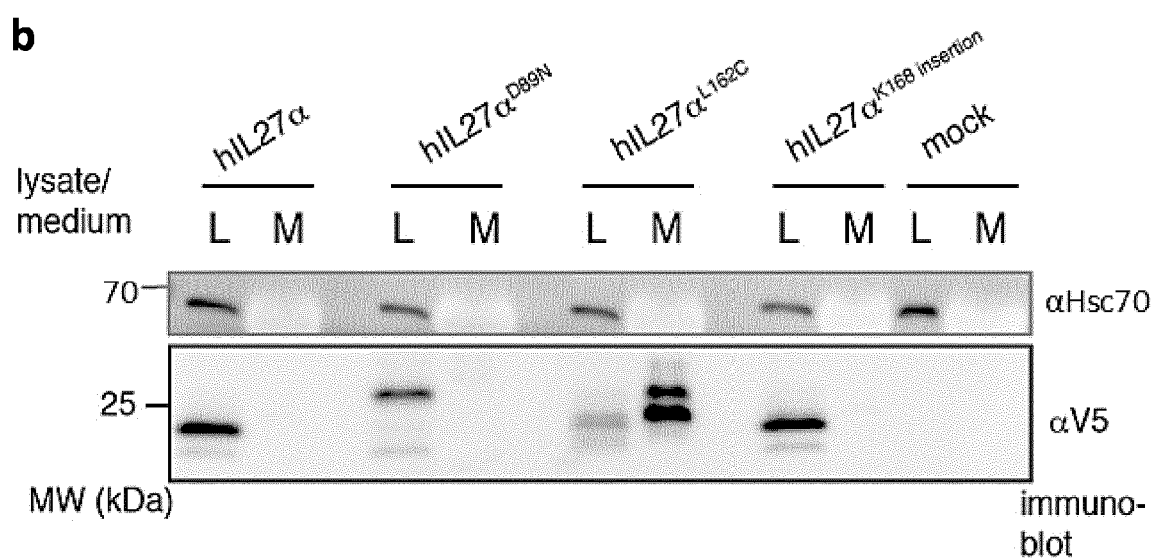
Figure 3:
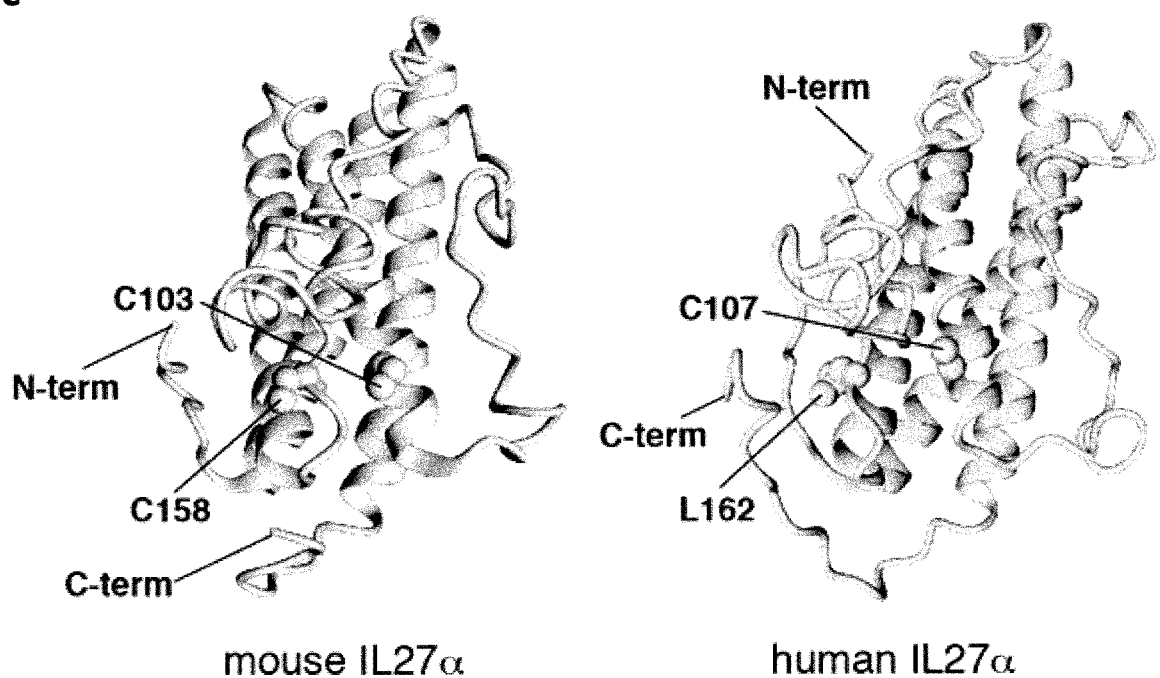
Figure 3:
Figure 3:
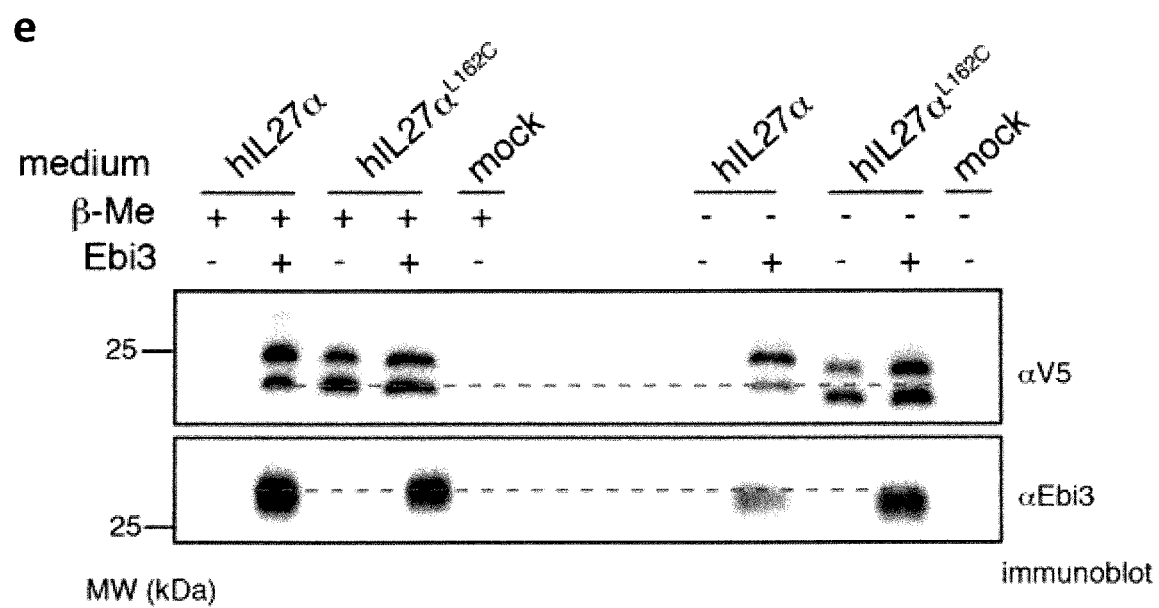

Also, the inventors have focused on a characteristic feature of IL-27α, a poly-glutamate stretch, which is predicted by homology modeling to be unstructured (see FIG. 3(c)). It may thus be involved in retention of the protein either by being recognized directly by components of the ER quality control system or by entropically destabilizing the native state of the protein. To test these hypotheses, the inventors generated two loop-deletion mutants: In hIL-27α$^{Δ164-176}$ (SEQ ID NO: 24) the poly-glutamate stretch alone was eliminated and in hIL-27α$^{Δ164-180}$ (SEQ ID NO: 25) a few additional C-terminal residues predicted to also be part of the unstructed loop were included in the deletion. For both loop-deletion mutants the inventors observed cellular retention in isolation and secretion induced by EBI3 (see FIG. 4(b)). In a third mutant, the inventors replaced the poly-glu sequence by a gly-ser linker (hIL-27α$^{Δ164-180toGS}$ (SEQ ID NO: 26)) to test for sequence specific effects of the poly-glu stretch on hIL-27α versus entropic destabilization of the native state by this flexible linker without using deletion as a more drastic approach. Again, hIL-27α$^{Δ164-180toGS}$ (SEQ ID NO: 26) was retained in the cell and EBI3 induced its secretion (see FIG. 4(b)). These findings proof of globally incomplete folding of hIL-27α (SEQ ID NO: 1) as opposed to a specific effect of the poly-glu stretch and furthermore reveal that the poly-glu loop is not necessary for EBI3-mediated secretion of hIL-27α (SEQ ID NO: 1).

Example 3: Recognition by ER Chaperones

To further assess the folding status of hIL-27α, the inventors tested if it was recognized by ER chaperones, leading to its retention. The inventors have therefore focused on the chaperone BiP (immunoglobulin heavy-chain binding protein), which binds hydrophobic amino acid stretches that are exposed by incompletely folded polypeptides in the ER[22,23]. A good correlation between protein folding in vitro, in vivo and BiP binding exists and thus BiP binding can serve as a relevant proxy to assess the folding state of a protein in the cell[24]. When the inventors tested for BiP binding to either wt hIL-27α (SEQ ID NO: 1) or hIL-27α$^{L162C}$ (SEQ ID NO: 2) by co-immunoprecipitation experiments the inventors surprisingly discovered that BiP binds to wild type (wt)hIL-27α(SEQ ID NO: 1) significantly better than to hIL-27α$^{L162C}$ (SEQ ID NO: 2)(see FIG. 4(c)).

This reveals a globally unstructured hIL-27α (SEQ ID NO: 1), which is retained in the ER in the absence of EBI3 due to chaperone binding.

Example 4: Molecular Dynamics Simulations

To obtain further structural insights into hIL-27α (SEQ ID NO: 1), the inventors performed molecular dynamics simulations on the homology model of wild type (wt)hIL-27α (SEQ ID NO: 1) as well as on hIL-27α$^{L162C}$ (SEQ ID NO: 2) with a disulfide bridge formed, which is present in this protein (see FIGS. 3(e) and (f)).

Whereas no global unfolding of either protein was observed during the simulations, the presence of the disulfide bond significantly reduced the dynamics of two large loops within hIL-27α$^{L162C}$ (SEQ ID NO: 2). For one of those, the poly-glu loop, this was expected as the disulfide bridge directly restrains its N-terminus (see FIGS. 4(d) and (e)). Interestingly, in the presence of the disulfide bond the inventors surprisingly found reduced dynamics of the loop connecting helices 1 and 2 in hIL-27α (SEQ ID NO: 1) (see FIGS. 4(d) and (e)). This loop contains several hydrophobic residues that, due to the disulfide-bridge, also become restricted in dynamics and can interact with and potentially shield hydrophobic residues in the C-terminal end of the poly-glu loop as well as in helices 2 and 4 of hIL-27α (SEQ ID NO: 1) and thus stabilizes the native state.

It is shown that EBI3 is able to release otherwise unfolded hIL-27α (SEQ ID NO: 1) from ER retention. However, it was not known up to now, if EBI3 is only needed to induce correct folding of the IL-27 alpha subunit, or if stable heterodimerization is needed for secretion of hIL-27α (SEQ ID NO: 1). To address this question, the inventors designed a human EBI3 construct that contained a C-terminally fused ER retention sequence (hEBI3$^{KDEL}$ (SEQ ID NO: 27)). When co-expressed with hEBI3$^{KDEL}$ (SEQ ID NO: 27), hIL-27α (SEQ ID NO: 1) was not secreted into the medium (see FIG. 4(f)). hIL-27α (SEQ ID NO: 1), however, shows higher levels in the presence of hEBI3$^{KDEL}$ (SEQ ID NO: 27) than in isolation, arguing that assembly with EBI3 stabilizes hIL-27α. Taken together, stable heterodimerization with EBI3 is a prerequisite for folding of hIL-27α and its release from ER retention.

Example 5: Assembly-Induced Versus Autonomous Secretion of IL-27α is Evolutionary Conserved, Affecting an Organism's Cytokine Repertoire The secretion behavior of IL-27α and thus potential immune regulation mediated by this subunit is dependent on a single Cys residue for mouse and man. It was therefore the question, if this was a feature conserved for other species.

A sequence alignment of several species revealed surprising differences:

The first cysteine residue in IL-27α was generally highly conserved, with an exception e.g. in *Bos Taurus* (SEQ ID NO: 11) (see FIG. 5(a)). Interestingly, the *Criteculus griseus* sequence (SEQ ID NO: 16) was very similar to its close relative *Mus musculus* (SEQ ID NO: 10), whereas rat (SEQ ID NO: 21) and rabbit (SEQ ID NO: 20) even had three cysteines (see FIG. 5(a)). The sequences of gorilla (SEQ ID NO: 15) and pig (SEQ ID NO: 19) were reminiscent of the human in terms of cysteines, whereas for e.g. *equus caballus* (SEQ ID NO: 17) and *ursus maritimus* (SEQ ID NO: 13) interestingly the first cysteine residue was conserved yet a second one was only found close to the C-terminus (see FIG. 5(a)).

To analyze the impact of the variations on IL-27α secretion, the inventors picked sequences representative of most of the Cys combinations: *Sarcophilus harrisii* (SEQ ID NO: 12) (one cysteine), *Ursus maritimus* (SEQ ID NO: 13) (two cysteines, but one C-terminal) and *Bos taurus* (SEQ ID NO: 11) (no cysteine).

Strikingly, *S. harrisii* IL-27α (SEQ ID NO: 12) was retained in isolation and its secretion could be induced by EBI3, as expected from its "human-like" sequence. *U. maritimus* IL-27α (SEQ ID NO: 13) was secreted even in isolation, suggesting that a C-terminal cysteine could potentially also act stabilizing. *B. taurus* IL-27α (SEQ ID NO: 11) was retained in isolation and secreted upon co-expression of EBI3 (see FIG. 5(b)).

Taken together, a disulfide bridge/Cys pair generally has a stabilizing role on IL-27α and decisively influences whether this subunit can be secreted in isolation and thus potentially perform immunoregulatory roles. For IL-27α derived from all species tested, human EBI3 increased/induced its secretion, arguing for a highly conserved IL-27α-EBI3 interface.

To further confirm the important role of the disulfide bridge in IL-27α secretion, the inventors replaced the second cysteine in mouse IL-27α by a leucine (C158L) (SEQ ID NO: 29), thus providing a construct more similar to the human sequence. mIL-27α$^{C158L}$ (SEQ ID NO: 29) was now retained in the cell in isolation and its secretion could be induced by human EBI3 (see FIG. 5(c)).

Example 6: hIL-27α$^{L162C}$ Increases the Secretion of the Pro-Inflammatory Cytokine IL-6 from LPS-Stimulated THP-1 Macrophages To assess biological consequences of IL-27α-induced signaling in human immune cells, the inventors of the present invention stimulated THP-1 macrophages with LPS either in the absence or presence of hIL-27α$^{L162C}$. hIL-27α$^{L162C}$ increased the secretion of the pro-inflammatory cytokines IL-6 (FIG. 9(a)) and TNF-α (FIG. 9(b)), corroborating its role as a functional cytokine[41] that modulates immune cell function. These findings show that the muteins of the present invention is active on human immune cells. The invention is further characterized by the following items:

Items:
1. A secretion-competent mutein of the α-subunit of human Interleukin 27 (SEQ ID NO: 1), wherein at least one of the amino acid residues of the α-subunit of human Interleukin 27 (SEQ ID NO: 1) selected from the group consisting of sequence positions 160, 161, 162, 163, 180, 181 and 182 is mutated.
2. The mutein of item 1, wherein at least one of the amino acid residues at sequence positions 160 to 163 is mutated
3. The mutein of item 1 or 2, wherein at least one of the amino acid residues at sequence positions 180 to 182 is mutated.
4. The mutein of any of the preceding items, wherein the amino acid residue at sequence position 160 is replaced by cysteine (SEQ ID NO: 3).
5. The mutein of any of the preceding items, wherein the amino acid residue at sequence position 161 is replaced by cysteine (SEQ ID NO: 4).
6. The mutein of any of the preceding items, wherein the amino acid residue at sequence position 162 is replaced by cysteine (SEQ ID NO: 2).

7. The mutein of any of the preceding items, wherein the amino acid residue at sequence position 163 is replaced by cysteine (SEQ ID NO: 5).
8. The mutein of any of the preceding items, wherein the amino acid residue at sequence position 180 is replaced by cysteine (SEQ ID NO: 6).
9. The mutein of any of the preceding items, wherein the amino acid residue at sequence position 181 is replaced by cysteine (SEQ ID NO: 7).
10. The mutein of any of the preceding items, wherein the amino acid residue at sequence position 182 is replaced by cysteine (SEQ ID NO: 8).
11. The mutein of any of the preceding items, wherein the mutein further comprises one or more salt bridges.
12. The mutein of any of the preceding items, wherein the mutein further comprises one or more disulfide-bridges.
13. A secretion-competent mutein of human Interleukin 27, comprising an α-subunit p28 and a β-subunit Ebi3, wherein the α-subunit is a secretion-competent mutein of the α-subunit of human Interleukin 27 (SEQ ID NO: 1) of any of items 1 to 12.
14. The mutein of item 13, wherein at least one of the amino acid residues at sequence positions 160 to 163 is mutated.
15. The mutein of items 13 or 14, wherein at least one of the amino acid residues at sequence positions 180 to 182 is mutated.
16. The mutein of any of items 13 to 15, wherein the amino acid residue at sequence position 160 is replaced by cysteine.
17. The mutein of any of items 13 to 16, wherein the amino acid residue at sequence position 161 is replaced by cysteine.
18. The mutein of any of items 13 to 17, wherein the amino acid residue at sequence position 162 is replaced by cysteine.
19. The mutein of any of items 13 to 18, wherein the amino acid residue at sequence position 163 is replaced by cysteine.
20. The mutein of any of items 13 to 19, wherein the amino acid residue at sequence position 180 is replaced by cysteine.
21. The mutein of any of items 13 to 20, wherein the amino acid residue at sequence position 181 is replaced by cysteine.
22. The mutein of any of items 13 to 21, wherein the amino acid residue at sequence position 182 is replaced by cysteine.
23. The mutein of any of items 13 to 22, wherein the mutein further comprises one or more salt bridges.
24. The mutein of any of items 13 to 23, wherein the mutein further comprises one or more disulfide-bridges.
25. A nucleic acid molecule comprising a nucleotide sequence encoding the secretion-competent mutein of human Interleukin 27 or the secretion-competent mutein of the α-subunit of human Interleukin 27 of any of items 1 to 24.
26. A nucleic acid molecule according to item 25, comprising a nucleotide sequence encoding a mutein of SEQ ID NO: 2, SEQ ID NO: 3, SEQ ID NO: 4, SEQ ID NO: 5, SEQ ID NO: 6, SEQ ID NO: 7, SEQ ID NO: 8.
27. A nucleic acid molecule of items 25 or 26, wherein the nucleic acid molecule is operably linked to a regulatory sequence to allow expression of the nucleic acid molecule.
28. A nucleic acid molecule of item 27, wherein the regulatory sequence comprises a promoter sequence.
29. The nucleic acid molecule of any of items 25 to 28 comprised in a vector.
30. A host cell containing a nucleic acid molecule of any of items 25 to 29.
31. An immune modulator comprising a mutein of any of items 1 to 24.
32. Use of a mutein of any of items 1 to 24 for the manufacture of a medicament for treating infectious diseases, autoimmune diseases, cancer, chronic inflammatory diseases, such as chronic inflammatory bowel disease, acute inflammatory diseases, sepsis, septic shock, diabetes or asthma in a mammal.
33. The mutein of any of items 1 to 24 for use in the treatment of infectious diseases, autoimmune diseases, cancer, chronic inflammatory diseases, such as chronic inflammatory bowel disease, acute inflammatory diseases, sepsis, septic shock, diabetes or asthma.
34. A method of treating an Interleukin 27-mediated disease, preferably an infectious disease, an autoimmune disease, cancer, a chronic inflammatory disease, such as chronic inflammatory bowel disease, acute inflammatory diseases, sepsis, septic shock, diabetes or asthma in a mammal, comprising the step of administering a composition comprising a mutein of any of items 1 to 24 to a mammal in need thereof.
35. Method for producing a mutein according to any of items 1 to 24, comprising the steps of:
    (a) introducing into a nucleic acid molecule encoding the human Interleukin 27 polypeptide or the human Interleukin 27 α-subunit polypeptide a nucleotide sequence mutating at least one amino acid residues of human Interleukin 27 or of the α-subunit of human Interleukin 27 selected from the group consisting of sequence positions 160, 161, 162, 163, 180, 181 and 182, and
    (b) introducing the obtained nucleic acid molecule for expression into a suitable host cell or into a suitable cell extract or cell lysate.
36. The method of item 35, wherein in step (a) into a nucleic acid molecule encoding the human Interleukin 27 polypeptide or the human Interleukin 27 α-subunit polypeptide a nucleotide sequence is introduced mutating at least one of the amino acid residues at sequence positions 160 to 163.
37. The method of item 35 or 36, wherein in step (a) into a nucleic acid molecule encoding the human Interleukin 27 polypeptide or the human Interleukin 27 α-subunit polypeptide a nucleotide sequence is introduced mutating at least one of the amino acid residues at sequence positions 180 to 182.
38. The method of any of items 35 to 37, wherein in step (a) into a nucleic acid molecule encoding the human Interleukin 27 polypeptide or the human Interleukin 27 α-subunit polypeptide a nucleotide sequence is introduced mutating at least one of the amino acid residues at sequence positions 160 to 163 to cysteine.
39. The method of any of items 35 to 38, wherein in step (a) into a nucleic acid molecule encoding the human Interleukin 27 polypeptide or the human Interleukin 27 α-subunit polypeptide a nucleotide sequence is introduced mutating at least one of the amino acid residues at sequence positions 180 to 182 to cysteine.
40. The method of any of items 35 to 39, wherein in step (a) into a nucleic acid molecule encoding the human Interleukin 27 polypeptide or the human Interleukin 27 α-subunit polypeptide a nucleotide sequence is introduced mutating the amino acid residue at sequence position 160 to cysteine.

41. The method of any of items 35 to 40, wherein in step (a) into a nucleic acid molecule encoding the human Interleukin 27 polypeptide or the human Interleukin 27 α-subunit polypeptide a nucleotide sequence is introduced mutating the amino acid residue at sequence position 161 to cysteine.

42. The method of any of items 35 to 41, wherein in step (a) into a nucleic acid molecule encoding the human Interleukin 27 polypeptide or the human Interleukin 27 α-subunit polypeptide a nucleotide sequence is introduced mutating the amino acid residue at sequence position 162 to cysteine.

43. The method of any of items 35 to 42, wherein in step (a) into a nucleic acid molecule encoding the human Interleukin 27 polypeptide or the human Interleukin 27 α-subunit polypeptide a nucleotide sequence is introduced mutating the amino acid residue at sequence position 163 to cysteine.

44. The method of any of items 35 to 43, wherein in step (a) into a nucleic acid molecule encoding the human Interleukin 27 polypeptide or the human Interleukin 27 α-subunit polypeptide a nucleotide sequence is introduced mutating the amino acid residue at sequence position 180 to cysteine.

45. The method of any of items 35 to 44, wherein in step (a) into a nucleic acid molecule encoding the human Interleukin 27 polypeptide or the human Interleukin 27 α-subunit polypeptide a nucleotide sequence is introduced mutating the amino acid residue at sequence position 181 to cysteine.

46. The method of any of items 35 to 45, wherein in step (a) into a nucleic acid molecule encoding the human Interleukin 27 polypeptide or the human Interleukin 27 α-subunit polypeptide a nucleotide sequence is introduced mutating the amino acid residue at sequence position 182 to cysteine.

47. A secretion-incompetent mutein of the α-subunit of mouse Interleukin 27 (SEQ ID NO: 10), wherein at least one of the two cysteine residues at amino acid positions 103 and 158 is/are mutated or deleted.

48. The secretion-incompetent mutein of the α-subunit of mouse Interleukin 27 of item 47, wherein the at least one of the two cysteine residues at amino acid positions 103 and 158 is replaced by hydrophobic amino acid residue.

49. The secretion-incompetent mutein of the α-subunit of mouse Interleukin 27 of item 47 or 48, wherein the at least one of the two cysteines at amino acid positions 103 and 158 is replaced by a serine, leucine, isoleucine or alanine residue.

REFERENCES

1. Vignali, D. A. & Kuchroo, V. K. IL-12 family cytokines: immunological playmakers. *Nat Immunol* 13, 722-8 (2012).
2. Langrish, C. L. et al. IL-12 and IL-23: master regulators of innate and adaptive immunity. *Immunol Rev* 202, 96-105 (2004).
3. Yoshida, H. & Hunter, C. A. The immunobiology of interleukin-27. *Annu Rev Immunol* 33, 417-43 (2015).
4. Pflanz, S. et al. IL-27, a heterodimeric cytokine composed of EBI3 and p28 protein, induces proliferation of naive CD4(+) T cells. *Immunity* 16, 779-90 (2002).
5. Awasthi, A. et al. A dominant function for interleukin 27 in generating interleukin 10-producing anti-inflammatory T cells. *Nat Immunol* 8, 1380-9 (2007).
6. Fitzgerald, D. C. et al. Suppression of autoimmune inflammation of the central nervous system by interleukin 10 secreted by interleukin 27-stimulated T cells. *Nat Immunol* 8, 1372-9 (2007).
7. Stumhofer, J. S. et al. Interleukins 27 and 6 induce STAT3-mediated T cell production of interleukin 10. *Nat Immunol* 8, 1363-71 (2007).
8. Batten, M. et al. Interleukin 27 limits autoimmune encephalomyelitis by suppressing the development of interleukin 17-producing T cells. *Nat Immunol* 7, 929-36 (2006).
9. Stumhofer, J. S. et al. Interleukin 27 negatively regulates the development of interleukin 17-producing T helper cells during chronic inflammation of the central nervous system. *Nat Immunol* 7, 937-45 (2006).
10. Patel, D. D. & Kuchroo, V. K. Th17 Cell Pathway in Human Immunity: Lessons from Genetics and Therapeutic Interventions. *Immunity* 43, 1040-51 (2015).
11. Yoon, C. et al. Charged residues dominate a unique interlocking topography in the heterodimeric cytokine interleukin-12. *EMBO J* 19, 3530-41 (2000).
12. Lupardus, P. J. & Garcia, K. C. The structure of interleukin-23 reveals the molecular basis of p40 subunit sharing with interleukin-12. *J Mol Biol* 382, 931-41 (2008).
13. Wang, X. et al. A novel IL-23p19/Ebi3 (IL-39) cytokine mediates inflammation in Lupus-like mice. *Eur J Immunol* (2016).
14. Gubler, U. et al. Coexpression of two distinct genes is required to generate secreted bioactive cytotoxic lymphocyte maturation factor. *Proc Natl Acad Sci USA* 88, 4143-7 (1991).
15. Oppmann, B. et al. Novel p19 protein engages IL-12p40 to form a cytokine, IL-23, with biological activities similar as well as distinct from IL-12. *Immunity* 13, 715-25 (2000).
16. Reitberger, S., Haimerl, P., Aschenbrenner, I., Esser-von Bieren, J. & Feige, M. J. Assembly-induced folding regulates interleukin 12 biogenesis and secretion. *J Biol Chem* (2017).
17. Stumhofer, J. S. et al. A role for IL-27p28 as an antagonist of gp130-mediated signaling. *Nat Immunol* 11, 1119-26 (2010).
18. Pflanz, S. et al. WSX-1 and glycoprotein 130 constitute a signal-transducing receptor for IL-27. *J Immunol* 172, 2225-31 (2004).
19. Tormo, A. J., Beaupre, L. A., Elson, G., Crabe, S. & Gauchat, J. F. A polyglutamic acid motif confers IL-27 hydroxyapatite and bone-binding properties. *J Immunol* 190, 2931-7 (2013).
20. Braakman, I. & Hebert, D. N. Analysis of disulfide bond formation. *Curr Protoc Protein Sci* Chapter 14, Unit 14 1 (2001).
21. Anelli, T. et al. Thiol-mediated protein retention in the endoplasmic reticulum: the role of ERp44. *EMBO J* 22, 5015-22 (2003).
22. Behnke, J., Mann, M. J., Scruggs, F. L., Feige, M. J. & Hendershot, L. M. Members of the Hsp70 Family Recognize Distinct Types of Sequences to Execute ER Quality Control. *Mol Cell* 63, 739-52 (2016).
23. Flynn, G. C., Pohl, J., Flocco, M. T. & Rothman, J. E. Peptide-binding specificity of the molecular chaperone BiP. *Nature* 353, 726-30 (1991).
24. Feige, M. J., Behnke, J., Mittag, T. & Hendershot, L. M. Dimerization-dependent Folding Underlies Assembly Control of the Clonotypic alphabetaT Cell Receptor Chains. *J Biol Chem* 290, 26821-31 (2015).

25. Elson, G. C. et al. CLF associates with CLC to form a functional heteromeric ligand for the CNTF receptor complex. *Nat Neurosci* 3, 867-72 (2000).
26. Duitman, E. H., Orinska, Z., Bulanova, E., Paus, R. & Bulfone-Paus, S. How a cytokine is chaperoned through the secretory pathway by complexing with its own receptor: lessons from interleukin-15 (IL-15)/IL-15 receptor alpha. *Mol Cell Biol* 28, 4851-61 (2008).
27. Crabe, S. et al. The IL-27 p28 subunit binds cytokine-like factor 1 to form a cytokine regulating NK and T cell activities requiring IL-6R for signaling. *J Immunol* 183, 7692-702 (2009).
28. Garbers, C. et al. An interleukin-6 receptor-dependent molecular switch mediates signal transduction of the IL-27 cytokine subunit p28 (IL-30) via a gp130 protein receptor homodimer. *J Biol Chem* 288, 4346-54 (2013).
29. Dietrich, C., Candon, S., Ruemmele, F. M. & Devergne, O. A soluble form of IL-27Ralpha is a natural IL-27 antagonist. *J Immunol* 192, 5382-9 (2014).
30. Scheller, J., Schuster, B., Holscher, C., Yoshimoto, T. & Rose-John, S. No inhibition of IL-27 signaling by soluble gp130. *Biochem Biophys Res Commun* 326, 724-8 (2005).
31. Wirtz, S. et al. Protection from lethal septic peritonitis by neutralizing the biological function of interleukin 27. *J Exp Med* 203, 1875-81 (2006).
32. Hendershot, L. et al. Inhibition of immunoglobulin folding and secretion by dominant negative BiP ATPase mutants. *Proc Natl Acad Sci USA* 93, 5269-74 (1996).
33. Hendershot, L. M. et al. In vivo expression of mammalian BiP ATPase mutants causes disruption of the endoplasmic reticulum. *Mol Biol Cell* 6, 283-96 (1995).
34. Devergne, O., Coulomb-L'Hermine, A., Capel, F., Moussa, M. & Capron, F. Expression of Epstein-Barr virus-induced gene 3, an interleukin-12 p40-related molecule, throughout human pregnancy: involvement of syncytiotrophoblasts and extravillous trophoblasts. *Am J Pathol* 159, 1763-76 (2001).
35. Sievers, F. et al. Fast, scalable generation of high-quality protein multiple sequence alignments using Clustal Omega. *Mol Syst Biol* 7, 539 (2011).
36. Zhang, Y. I-TASSER server for protein 3D structure prediction. *BMC Bioinformatics* 9, 40 (2008).
37. Case, D. A., Babin, V., Berryman, J. T., Betz, R. M., Cai, Q., Cerutti, D. S., Cheatham III, T. E., Darden, T. A., Duke, R. E., Gohlke, H., et al. (2014). AMBER 14.
38. Maier, J. A., Martinez, C., Kasavajhala, K., Wickstrom, L., Hauser, K. E., and Simmerling, C. (2015). ff14SB: Improving the Accuracy of Protein Side Chain and Backbone Parameters from ff99SB. *J Chem Theory Comput* 11, 3696-3713.
39. Jorgensen, W. L., Chandrasekhar, J., Madura, J. D., Impey, R. W., and Klein, M. L. (1983). Comparison of Simple Potential Functions for Simulating Liquid Water. *J Chem Phys* 79, 926-935.
40. Lund, M. E., To, J., O'Brien, B. A., and Donnelly, S. (2016). The choice of phorbol 12-myristate 13-acetate differentiation protocol influences the response of THP-1 macrophages to a pro-inflammatory stimulus. Journal of immunological methods 430, 64-70.
41. Petes, C., Mariani, M. K., Yang, Y., Grandvaux, N., and Gee, K. (2018). Interleukin (IL)-6 Inhibits IL-27- and IL-30-Mediated Inflammatory Responses in Human Monocytes. Frontiers in immunology 9, 256.
42. Shimozato et al., (2009). The secreted form of p28 subunit of interleukin (IL)-27 inhibits biological functions of IL-27 and suppressess anti-allogeneic immune responses. Immunology 128, 816-826.
43. Yan, J., Mitra, A., Hu, J., Cutrera, J. J., Xia, X., Doetschman, T., Gagea, M., Mishra, L., and Li, S. (2016). Interleukin-30 (IL-27p28) alleviates experimental sepsis by modulating cytokine profile in NKT cells. *J Hepatol* 64, 1128-1136.
44. Shimozato, O., Sato, A., Kawamura, K., Chiyo, M., Ma, G., Li, Q., and Tagawa, M. (2009). The secreted form of p28 subunit of interleukin (IL)-27 inhibits biological functions of IL-27 and suppresses anti-allogeneic immune responses. Immunology 128, e816-825.

SEQUENCE LISTING

```
<160> NUMBER OF SEQ ID NOS: 36

<210> SEQ ID NO 1
<211> LENGTH: 243
<212> TYPE: PRT
<213> ORGANISM: Homo sapiens

<400> SEQUENCE: 1

Met Gly Gln Thr Ala Gly Asp Leu Gly Trp Arg Leu Ser Leu Leu Leu
1               5                   10                  15

Leu Pro Leu Leu Leu Val Gln Ala Gly Val Trp Gly Phe Pro Arg Pro
            20                  25                  30

Pro Gly Arg Pro Gln Leu Ser Leu Gln Glu Leu Arg Arg Glu Phe Thr
        35                  40                  45

Val Ser Leu His Leu Ala Arg Lys Leu Leu Ser Glu Val Arg Gly Gln
    50                  55                  60

Ala His Arg Phe Ala Glu Ser His Leu Pro Gly Val Asn Leu Tyr Leu
65                  70                  75                  80

Leu Pro Leu Gly Glu Gln Leu Pro Asp Val Ser Leu Thr Phe Gln Ala
                85                  90                  95

Trp Arg Arg Leu Ser Asp Pro Glu Arg Leu Cys Phe Ile Ser Thr Thr
            100                 105                 110
```

```
Leu Gln Pro Phe His Ala Leu Leu Gly Gly Leu Gly Thr Gln Gly Arg
            115                 120                 125

Trp Thr Asn Met Glu Arg Met Gln Leu Trp Ala Met Arg Leu Asp Leu
    130                 135                 140

Arg Asp Leu Gln Arg His Leu Arg Phe Gln Val Leu Ala Ala Gly Phe
145                 150                 155                 160

Asn Leu Pro Glu Glu Glu Glu Glu Glu Glu Glu Glu Glu Glu Glu Glu
                165                 170                 175

Arg Lys Gly Leu Leu Pro Gly Ala Leu Gly Ser Ala Leu Gln Gly Pro
                180                 185                 190

Ala Gln Val Ser Trp Pro Gln Leu Leu Ser Thr Tyr Arg Leu Leu His
            195                 200                 205

Ser Leu Glu Leu Val Leu Ser Arg Ala Val Arg Glu Leu Leu Leu Leu
    210                 215                 220

Ser Lys Ala Gly His Ser Val Trp Pro Leu Gly Phe Pro Thr Leu Ser
225                 230                 235                 240

Pro Gln Pro

<210> SEQ ID NO 2
<211> LENGTH: 243
<212> TYPE: PRT
<213> ORGANISM: artificial sequence
<220> FEATURE:
<223> OTHER INFORMATION: mutein of human Interleukin 27 alpha-subunit
      L162C

<400> SEQUENCE: 2

Met Gly Gln Thr Ala Gly Asp Leu Gly Trp Arg Leu Ser Leu Leu Leu
1               5                   10                  15

Leu Pro Leu Leu Leu Val Gln Ala Gly Val Trp Gly Phe Pro Arg Pro
            20                  25                  30

Pro Gly Arg Pro Gln Leu Ser Leu Gln Glu Leu Arg Arg Glu Phe Thr
            35                  40                  45

Val Ser Leu His Leu Ala Arg Lys Leu Leu

Ser Lys Ala Gly His Ser Val Trp Pro Leu Gly Phe Pro Thr Leu Ser
225                 230                 235                 240

Pro Gln Pro

<210> SEQ ID NO 3
<211> LENGTH: 243
<212> TYPE: PRT
<213> ORGANISM: artificial sequence
<220> FEATURE:
<223> OTHER INFORMATION: mutein of human Interleukin 27 alpha-subunit
      F160C

<400> SEQUENCE: 3

Met Gly Gln Thr Ala Gly Asp Leu Gly Trp Arg Leu Ser Leu Leu Leu
1               5                   10                  15

Leu Pro Leu Leu Leu Val Gln Ala Gly Val Trp Gly Phe Pro Arg Pro
                20                  25                  30

Pro Gly Arg Pro Gln Leu Ser Leu Gln Glu Leu Arg Arg Glu Phe Thr
            35                  40                  45

Val Ser Leu His Leu Ala Arg Lys Leu Leu Ser Glu Val Arg Gly Gln
        50                  55                  60

Ala His Arg Phe Ala Glu Ser His Leu Pro Gly Val Asn Leu Tyr Leu
65                  70                  75                  80

Leu Pro Leu Gly Glu Gln Leu Pro Asp Val Ser Leu Thr Phe Gln Ala
                85                  90                  95

Trp Arg Arg Leu Ser Asp Pro Glu Arg Leu Cys Phe Ile Ser Thr Thr
            100                 105                 110

Leu Gln Pro Phe His Ala Leu Leu Gly Gly Leu Gly Thr Gln Gly Arg
        115                 120                 125

Trp Thr Asn Met Glu Arg Met Gln Leu Trp Ala Met Arg Leu Asp Leu
130                 135                 140

Arg Asp Leu Gln Arg His Leu Arg Phe Gln Val Leu Ala Ala Gly Cys
145                 150                 155                 160

Asn Leu Pro Glu Glu Glu Glu Glu Glu Glu Glu Glu Glu Glu Glu Glu
                165                 170                 175

Arg Lys Gly Leu Leu Pro Gly Ala Leu Gly Ser Ala Leu Gln Gly Pro
            180                 185                 190

Ala Gln Val Ser Trp Pro Gln Leu Leu Ser Thr Tyr Arg Leu Leu His
        195                 200                 205

Ser Leu Glu Leu Val Leu Ser Arg Ala Val Arg Glu Leu Leu Leu Leu
210                 215                 220

Ser Lys Ala Gly His Ser Val Trp Pro Leu Gly Phe Pro Thr Leu Ser
225                 230                 235                 240

Pro Gln Pro

<210> SEQ ID NO 4
<211> LENGTH: 243
<212> TYPE: PRT
<213> ORGANISM: artificial sequence
<220> FEATURE:
<223> OTHER INFORMATION: mutein of human Interleukin 27 alpha-subunit
      N161C

<400> SEQUENCE: 4

Met Gly Gln Thr Ala Gly Asp Leu Gly Trp Arg Leu Ser Leu Leu Leu
1               5                   10                  15

Leu Pro Leu Leu Leu Val Gln Ala Gly Val Trp Gly Phe Pro Arg Pro
                20                  25                  30

```
Pro Gly Arg Pro Gln Leu Ser Leu Gln Glu Leu Arg Arg Glu Phe Thr
            35                  40                  45

Val Ser Leu His Leu Ala Arg Lys Leu Leu Ser Glu Val Arg Gly Gln
    50                  55                  60

Ala His Arg Phe Ala Glu Ser His Leu Pro Gly Val Asn Leu Tyr Leu
 65                  70                  75                  80

Leu Pro Leu Gly Glu Gln Leu Pro Asp Val Ser Leu Thr Phe Gln Ala
                85                  90                  95

Trp Arg Arg Leu Ser Asp Pro Glu Arg Leu Cys Phe Ile Ser Thr Thr
                100                 105                 110

Leu Gln Pro Phe His Ala Leu Leu Gly Gly Leu Gly Thr Gln Gly Arg
            115                 120                 125

Trp Thr Asn Met Glu Arg Met Gln Leu Trp Ala Met Arg Leu Asp Leu
130                 135                 140

Arg Asp Leu Gln Arg His Leu Arg Phe Gln Val Leu Ala Ala Gly Phe
145                 150                 155                 160

Cys Leu Pro Glu Glu Glu Glu Glu Glu Glu Glu Glu Glu Glu Glu Glu
                165                 170                 175

Arg Lys Gly Leu Leu Pro Gly Ala Leu Gly Ser Ala Leu Gln Gly Pro
                180                 185                 190

Ala Gln Val Ser Trp Pro Gln Leu Leu Ser Thr Tyr Arg Leu Leu His
            195                 200                 205

Ser Leu Glu Leu Val Leu Ser Arg Ala Val Arg Glu Leu Leu Leu Leu
            210                 215                 220

Ser Lys Ala Gly His Ser Val Trp Pro Leu Gly Phe Pro Thr Leu Ser
225                 230                 235                 240

Pro Gln Pro

<210> SEQ ID NO 5
<211> LENGTH: 243
<212> TYPE: PRT
<213> ORGANISM: artificial sequence
<220> FEATURE:
<223> OTHER INFORMATION: mutein of human Interleukin 27 alpha-subunit
      P163C

<400> SEQUENCE: 5

Met Gly Gln Thr Ala Gly Asp Leu Gly Trp Arg Leu Ser Leu Leu Leu
1               5                   10                  15

Leu Pro Leu Leu Leu Val Gln Ala Gly Val Trp Gly Phe Pro Arg Pro
                20                  25                  30

Pro Gly Arg Pro Gln Leu Ser Leu Gln Glu Leu Arg Arg Glu Phe Thr
            35                  40                  45

Val Ser Leu His Leu Ala Arg Lys Leu Leu Ser Glu Val Arg Gly Gln
    50                  55                  60

Ala His Arg Phe Ala Glu Ser His Leu Pro Gly Val Asn Leu Tyr Leu
 65                  70                  75                  80

Leu Pro Leu Gly Glu Gln Leu Pro Asp Val Ser Leu Thr Phe Gln Ala
                85                  90                  95

Trp Arg Arg Leu Ser Asp Pro Glu Arg Leu Cys Phe Ile Ser Thr Thr
                100                 105                 110

Leu Gln Pro Phe His Ala Leu Leu Gly Gly Leu Gly Thr Gln Gly Arg
            115                 120                 125

Trp Thr Asn Met Glu Arg Met Gln Leu Trp Ala Met Arg Leu Asp Leu
130                 135                 140
```

```
Arg Asp Leu Gln Arg His Leu Arg Phe Gln Val Leu Ala Ala Gly Phe
145                 150                 155                 160

Asn Leu Cys Glu Glu Glu Glu Glu Glu Glu Glu Glu Glu Glu Glu Glu
                165                 170                 175

Arg Lys Gly Leu Leu Pro Gly Ala Leu Gly Ser Ala Leu Gln Gly Pro
                180                 185                 190

Ala Gln Val Ser Trp Pro Gln Leu Leu Ser Thr Tyr Arg Leu Leu His
        195                 200                 205

Ser Leu Glu Leu Val Leu Ser Arg Ala Val Arg Glu Leu Leu Leu Leu
        210                 215                 220

Ser Lys Ala Gly His Ser Val Trp Pro Leu Gly Phe Pro Thr Leu Ser
225                 230                 235                 240

Pro Gln Pro

<210> SEQ ID NO 6
<211> LENGTH: 243
<212> TYPE: PRT
<213> ORGANISM: artificial sequence
<220> FEATURE:
<223> OTHER INFORMATION: mutein of human Interleukin 27 alpha-subunit
      L180C

<400> SEQUENCE: 6

Met Gly Gln Thr Ala Gly Asp Leu Gly Trp Arg Leu Ser Leu Leu Leu
1               5                   10                  15

Leu Pro Leu Leu Leu Val Gln Ala Gly Val Trp Gly Phe Pro Arg Pro
                20                  25                  30

Pro Gly Arg Pro Gln Leu Ser Leu Gln Glu Leu Arg Arg Glu Phe Thr
            35                  40                  45

Val Ser Leu His Leu Ala Arg Lys Leu Leu Ser Glu Val Arg Gly Gln
        50                  55                  60

Ala His Arg Phe Ala Glu Ser His Leu Pro Gly Val Asn Leu Tyr Leu
65                  70                  75                  80

Leu Pro Leu Gly Glu Gln Leu Pro Asp Val Ser Leu Thr Phe Gln Ala
                85                  90                  95

Trp Arg Arg Leu Ser Asp Pro Glu Arg Leu Cys Phe Ile Ser Thr Thr
                100                 105                 110

Leu Gln Pro Phe His Ala Leu Leu Gly Gly Leu Gly Thr Gln Gly Arg
            115                 120                 125

Trp Thr Asn Met Glu Arg Met Gln Leu Trp Ala Met Arg Leu Asp Leu
130                 135                 140

Arg Asp Leu Gln Arg His Leu Arg Phe Gln Val Leu Ala Ala Gly Phe
145                 150                 155                 160

Asn Leu Pro Glu Glu Glu Glu Glu Glu Glu Glu Glu Glu Glu Glu Glu
                165                 170                 175

Arg Lys Gly Cys Leu Pro Gly Ala Leu Gly Ser Ala Leu Gln Gly Pro
            180                 185                 190

Ala Gln Val Ser Trp Pro Gln Leu Leu Ser Thr Tyr Arg Leu Leu His
        195                 200                 205

Ser Leu Glu Leu Val Leu Ser Arg Ala Val Arg Glu Leu Leu Leu Leu
        210                 215                 220

Ser Lys Ala Gly His Ser Val Trp Pro Leu Gly Phe Pro Thr Leu Ser
225                 230                 235                 240

Pro Gln Pro
```

<210> SEQ ID NO 7
<211> LENGTH: 243
<212> TYPE: PRT
<213> ORGANISM: artificial sequence
<220> FEATURE:
<223> OTHER INFORMATION: mutein of human Interleukin 27 alpha-subunit L181C

<400> SEQUENCE: 7

Met Gly Gln Thr Ala Gly Asp Leu Gly Trp Arg Leu Ser Leu Leu Leu
1               5                   10                  15

Leu Pro Leu Leu Leu Val Gln Ala Gly Val Trp Gly Phe Pro Arg Pro
                20                  25                  30

Pro Gly Arg Pro Gln Leu Ser Leu Gln Glu Leu Arg Arg Glu Phe Thr
            35                  40                  45

Val Ser Leu His Leu Ala Arg Lys Leu Leu Ser Glu Val Arg Gly Gln
50                  55                  60

Ala His Arg Phe Ala Glu Ser His Leu Pro Gly Val Asn Leu Tyr Leu
65                  70                  75                  80

Leu Pro Leu Gly Glu Gln Leu Pro Asp Val Ser Leu Thr Phe Gln Ala
                85                  90                  95

Trp Arg Arg Leu Ser Asp Pro Glu Arg Leu Cys Phe Ile Ser Thr Thr
            100                 105                 110

Leu Gln Pro Phe His Ala Leu Leu Gly Gly Leu Gly Thr Gln Gly Arg
        115                 120                 125

Trp Thr Asn Met Glu Arg Met Gln Leu Trp Ala Met Arg Leu Asp Leu
130                 135                 140

Arg Asp Leu Gln Arg His Leu Arg Phe Gln Val Leu Ala Ala Gly Phe
145                 150                 155                 160

Asn Leu Pro Glu Glu Glu Glu Glu Glu Glu Glu Glu Glu Glu Glu Glu
                165                 170                 175

Arg Lys Gly Leu Cys Pro Gly Ala Leu Gly Ser Ala Leu Gln Gly Pro
            180                 185                 190

Ala Gln Val Ser Trp Pro Gln Leu Leu Ser Thr Tyr Arg Leu Leu His
        195                 200                 205

Ser Leu Glu Leu Val Leu Ser Arg Ala Val Arg Glu Leu Leu Leu Leu
    210                 215                 220

Ser Lys Ala Gly His Ser Val Trp Pro Leu Gly Phe Pro Thr Leu Ser
225                 230                 235                 240

Pro Gln Pro

<210> SEQ ID NO 8
<211> LENGTH: 243
<212> TYPE: PRT
<213> ORGANISM: artificial sequence
<220> FEATURE:
<223> OTHER INFORMATION: mutein of human Interleukin 27 alpha-subunit P182C

<400> SEQUENCE: 8

Met Gly Gln Thr Ala Gly Asp Leu Gly Trp Arg Leu Ser Leu Leu Leu
1               5                   10                  15

Leu Pro Leu Leu Leu Val Gln Ala Gly Val Trp Gly Phe Pro Arg Pro
                20                  25                  30

Pro Gly Arg Pro Gln Leu Ser Leu Gln Glu Leu Arg Arg Glu Phe Thr
            35                  40                  45

Val Ser Leu His Leu Ala Arg Lys Leu Leu Ser Glu Val Arg Gly Gln
50                  55                  60

```
Ala His Arg Phe Ala Glu Ser His Leu Pro Gly Val Asn Leu Tyr Leu
 65                  70                  75                  80

Leu Pro Leu Gly Glu Gln Leu Pro Asp Val Ser Leu Thr Phe Gln Ala
                 85                  90                  95

Trp Arg Arg Leu Ser Asp Pro Glu Arg Leu Cys Phe Ile Ser Thr Thr
            100                 105                 110

Leu Gln Pro Phe His Ala Leu Leu Gly Gly Leu Gly Thr Gln Gly Arg
        115                 120                 125

Trp Thr Asn Met Glu Arg Met Gln Leu Trp Ala Met Arg Leu Asp Leu
    130                 135                 140

Arg Asp Leu Gln Arg His Leu Arg Phe Gln Val Leu Ala Ala Gly Phe
145                 150                 155                 160

Asn Leu Pro Glu Glu Glu Glu Glu Glu Glu Glu Glu Glu Glu Glu Glu
                165                 170                 175

Arg Lys Gly Leu Leu Cys Gly Ala Leu Gly Ser Ala Leu Gln Gly Pro
            180                 185                 190

Ala Gln Val Ser Trp Pro Gln Leu Leu Ser Thr Tyr Arg Leu Leu His
        195                 200                 205

Ser Leu Glu Leu Val Leu Ser Arg Ala Val Arg Glu Leu Leu Leu Leu
210                 215                 220

Ser Lys Ala Gly His Ser Val Trp Pro Leu Gly Phe Pro Thr Leu Ser
225                 230                 235                 240

Pro Gln Pro

<210> SEQ ID NO 9
<211> LENGTH: 229
<212> TYPE: PRT
<213> ORGANISM: Homo sapiens

<400> SEQUENCE: 9

Met Thr Pro Gln Leu Leu Ala Leu Val Leu Trp Ala Ser Cys Pro Pro
  1               5                  10                  15

Pro Cys Ser Gly Arg Lys Gly Pro Pro Ala Ala Leu Thr Leu Pro Arg
             20                  25                  30

Val Gln Cys Arg Ala Ser Arg Tyr Pro Ile Ala Val Asp Cys Ser Trp
         35                  40                  45

Thr Leu Pro Pro Ala Pro Asn Ser Thr Ser Pro Val Ser Phe Ile Ala
 50                  55                  60

Thr Tyr Arg Leu Gly Met Ala Ala Arg Gly His Ser Trp Pro Cys Leu
 65                  70                  75                  80

Gln Gln Thr Pro Thr Ser Thr Ser Cys Thr Ile Thr Asp Val Gln Leu
                 85                  90                  95

Phe Ser Met Ala Pro Tyr Val Leu Asn Val Thr Ala Val His Pro Trp
            100                 105                 110

Gly Ser Ser Ser Ser Phe Val Pro Phe Ile Thr Glu His Ile Ile Lys
        115                 120                 125

Pro Asp Pro Pro Glu Gly Val Arg Leu Ser Pro Leu Ala Glu Arg Gln
    130                 135                 140

Leu Gln Val Gln Trp Glu Pro Pro Gly Ser Trp Pro Phe Pro Glu Ile
145                 150                 155                 160

Phe Ser Leu Lys Tyr Trp Ile Arg Tyr Lys Arg Gln Gly Ala Ala Arg
                165                 170                 175

Phe His Arg Val Gly Pro Ile Glu Ala Thr Ser Phe Ile Leu Arg Ala
            180                 185                 190
```

Val Arg Pro Arg Ala Arg Tyr Val Gln Val Ala Ala Gln Asp Leu
        195                 200                 205

Thr Asp Tyr Gly Glu Leu Ser Asp Trp Ser Leu Pro Ala Thr Ala Thr
    210                 215                 220

Met Ser Leu Gly Lys
225

<210> SEQ ID NO 10
<211> LENGTH: 234
<212> TYPE: PRT
<213> ORGANISM: Mus musculus

<400> SEQUENCE: 10

Met Gly Gln Val Thr Gly Asp Leu Gly Trp Arg Leu Ser Leu Leu Leu
1               5                   10                  15

Leu Pro Leu Leu Leu Val Gln Ala Gly Ser Trp Gly Phe Pro Thr Asp
                20                  25                  30

Pro Leu Ser Leu Gln Glu Leu Arg Arg Glu Phe Thr Val Ser Leu Tyr
            35                  40                  45

Leu Ala Arg Lys Leu Leu Ser Glu Val Gln Gly Tyr Val His Ser Phe
        50                  55                  60

Ala Glu Ser Arg Leu Pro Gly Val Asn Leu Asp Leu Leu Pro Leu Gly
65                  70                  75                  80

Tyr His Leu Pro Asn Val Ser Leu Thr Phe Gln Ala Trp His His Leu
                85                  90                  95

Ser Asp Ser Glu Arg Leu Cys Phe Leu Ala Thr Thr Leu Arg Pro Phe
            100                 105                 110

Pro Ala Met Leu Gly Gly Leu Gly Thr Gln Gly Thr Trp Thr Ser Ser
        115                 120                 125

Glu Arg Glu Gln Leu Trp Ala Met Arg Leu Asp Leu Arg Asp Leu His
130                 135                 140

Arg His Leu Arg Phe Gln Val Leu Ala Ala Gly Phe Lys Cys Ser Lys
145                 150                 155                 160

Glu Glu Glu Asp Lys Glu Glu Glu Glu Glu Glu Glu Glu Glu Glu Lys
                165                 170                 175

Lys Leu Pro Leu Gly Ala Leu Gly Gly Pro Asn Gln Val Ser Ser Gln
            180                 185                 190

Val Ser Trp Pro Gln Leu Leu Tyr Thr Tyr Gln Leu Leu His Ser Leu
        195                 200                 205

Glu Leu Val Leu Ser Arg Ala Val Arg Asp Leu Leu Leu Leu Ser Leu
210                 215                 220

Pro Arg Arg Pro Gly Ser Ala Trp Asp Ser
225                 230

<210> SEQ ID NO 11
<211> LENGTH: 235
<212> TYPE: PRT
<213> ORGANISM: Bos taurus

<400> SEQUENCE: 11

Met Gly Gln Thr Ala Gly Asn Leu Gly Trp Arg Leu Ser Leu Leu Leu
1               5                   10                  15

Leu Phe Leu Leu Leu Ala Arg Ala Gly Val Trp Gly Phe Pro Arg Pro
                20                  25                  30

Pro Gly Arg Pro Pro Leu Ser Leu Gln Glu Leu Gln Arg Glu Phe Lys
            35                  40                  45

```
Val Ser Leu His Leu Ala Arg Lys Leu Leu Ser Glu Val Arg Val Gln
 50                  55                  60

Ala His His Phe Ala Glu Ser His Leu Pro Gly Val Asn Leu Asp Leu
 65                  70                  75                  80

Leu Pro Leu Ala Glu Gln Leu Pro Asn Val Ser Thr Thr Phe Gln Ala
                 85                  90                  95

Trp Arg Gly Leu Ser Ala Leu Ser Arg Ile Asp Leu Val Met Glu Trp
                100                 105                 110

Met Glu Thr Gly Val Val Leu Gly Met Gly Pro Arg Glu Ser Trp Thr
            115                 120                 125

Ser Ser Glu Arg Met Gln Leu Gln Ala Thr Arg Leu Asp Leu Arg Asp
130                 135                 140

Leu Gln Gln His Leu Arg Phe Gln Val Leu Ala Ala Gly Phe Asn Leu
145                 150                 155                 160

Pro Glu Glu His Glu Asn Glu Glu Lys Gly Leu Leu Pro Gly Ala
                165                 170                 175

Leu Gly Ala Pro Leu Gln Ile Ser Ala Gln Val Ser Trp Ser Arg Phe
            180                 185                 190

Leu Tyr Thr Tyr Arg Leu Leu His Ser Leu Glu Leu Leu Ser Arg
            195                 200                 205

Thr Val Arg Asp Leu Leu Leu Ser Arg Ala Gly Asn Ser Val Gln
210                 215                 220

Ala Leu Gly Phe Pro Thr Pro Ser Ser Gln Pro
225                 230                 235

<210> SEQ ID NO 12
<211> LENGTH: 224
<212> TYPE: PRT
<213> ORGANISM: Sarcophilus harrisii

<400> SEQUENCE: 12

Met Phe Ser Ser Ile Phe Gln Gly Leu Asn Leu Leu Leu Phe Ser Leu
  1               5                  10                  15

Leu Leu Asn Lys Ala Val Thr Cys Gly Phe Pro Trp Pro Arg Arg Gln
                 20                  25                  30

Pro Pro His Gly Leu Leu Asp Met Arg Ser Glu Phe Lys Ile Ser Leu
             35                  40                  45

Arg Leu Ala Arg Lys Leu Leu Ser Glu Ile Arg Gly Ile Ala His Leu
 50                  55                  60

Phe Ala Asp Thr His Leu Val Gly Val Ser Leu Asp Phe Leu Pro Leu
 65                  70                  75                  80

Thr Glu Gln Leu Pro Asn Val Thr Met Thr Phe Lys Thr Trp Leu Gln
                 85                  90                  95

Leu Ser Asp Pro Asp Arg Leu Cys Leu Ser Ser Leu Leu Gly His
                100                 105                 110

Phe Gln Thr Pro Leu Gly Glu Leu Glu Gly His Gln Gly Trp Lys Gly
            115                 120                 125

Ser Leu Arg Lys Arg Leu Trp Thr Ala Gln Leu Asp Leu Arg Asp Leu
130                 135                 140

Arg Ser His Leu His Tyr Gln Met Lys Ala Ile Gly Tyr Ser Ser Arg
145                 150                 155                 160

Glu Asp Glu Glu Ala Arg Gly Pro Glu Glu Arg Ala Leu Arg Arg Ile
            165                 170                 175

Ser Leu Thr Val Arg Gln Val Ser Trp Pro Gln Leu Leu Arg Thr Tyr
            180                 185                 190
```

```
Gln Leu Leu Arg Ser Leu Glu Leu Val Leu Ala Arg Ala Val Arg Asp
            195                 200                 205

Phe Leu Leu Leu Ser Lys Glu Val Ala Gln Ser Gln Ser Leu Ala Thr
    210                 215                 220
```

<210> SEQ ID NO 13
<211> LENGTH: 236
<212> TYPE: PRT
<213> ORGANISM: Ursus americanus

<400> SEQUENCE: 13

```
Met Gly Gln Met Ala Gly Asp Leu Gly Trp Arg Leu Ser Leu Leu Leu
1               5                   10                  15

Leu Ser Leu Leu Leu Ala Arg Ala Gly Val Trp Gly Phe Pro Arg Pro
                20                  25                  30

Pro Gly Arg Ser Pro Leu Ser Leu Gln Glu Leu Gln Arg Glu Phe Lys
            35                  40                  45

Val Ser Leu Gln Leu Ala Arg Lys Leu Leu Ser Glu Val Arg Thr Gln
    50                  55                  60

Ala His His Phe Ala Glu Ser His Leu Pro Gly Val Ser Leu Asp Leu
65                  70                  75                  80

Leu Pro Leu Gly Asp Gln Leu Pro Asn Val Ser Leu Thr Phe Gln Ala
                85                  90                  95

Trp His Ser Leu Ser Asp Pro Glu Arg Leu Cys Phe Leu Ser Met Met
            100                 105                 110

Leu Arg Pro Phe His Val Leu Leu Gly Arg Leu Gly Asn Gln Gly Gly
        115                 120                 125

Trp Thr Ser Ser Glu Lys Met Gln Leu Trp Thr Val Arg Leu Asp Leu
    130                 135                 140

Arg Asp Leu Gln Arg His Leu Arg Phe Gln Val Leu Ala Ala Gly Leu
145                 150                 155                 160

Asn Leu Pro Glu Glu Asn Glu Glu Arg Lys Gly Leu Leu Glu Trp
                165                 170                 175

Ala Pro Gly Gly Pro Ser Gln Ile Ser Ala Gln Pro Ser Trp Pro Gln
            180                 185                 190

Leu Leu Tyr Thr Tyr Gln Leu Leu His Ser Leu Glu Leu Val Leu Ala
        195                 200                 205

Arg Ala Val Arg Asp Leu Leu Leu Ser Gln Ala Gly Asn Pro Ala
    210                 215                 220

Pro Ala Leu Gly Cys Ser Thr Ser Ser Ser Gln Pro
225                 230                 235
```

<210> SEQ ID NO 14
<211> LENGTH: 237
<212> TYPE: PRT
<213> ORGANISM: Orcinus orca

<400> SEQUENCE: 14

```
Met Gly Gln Thr Ala Gly Asp Leu Gly Trp Arg Val Ser Leu Leu Leu
1               5                   10                  15

Leu Ser Leu Leu Leu Ala Arg Ala Gly Val Trp Gly Phe Pro Arg Pro
                20                  25                  30

Pro Gly Arg Pro Leu Arg Ser Leu Gln Glu Leu Gln Arg Glu Phe Lys
            35                  40                  45

Val Ser Leu His Leu Ser Arg Lys Leu Leu Ser Glu Val Arg Val Gln
    50                  55                  60
```

```
Ala Arg Asp Phe Ala Glu Ser His Leu Pro Gly Val Asn Leu Asp Leu
 65                  70                  75                  80

Leu Pro Leu Gly Glu Gln Leu Pro Asn Val Ser Leu Thr Phe Gln Ala
                 85                  90                  95

Trp Arg Gly Leu Ser Asp Pro Glu Arg Leu Arg Phe Leu Ser Met Thr
            100                 105                 110

Leu His Pro Phe His Thr Leu Leu Gly Gly Leu Gly Ser Gln Gly Phe
        115                 120                 125

Trp Thr Ser Ser Glu Arg Leu Gln Leu Trp Ala Met Arg Leu Asp Leu
    130                 135                 140

Arg Asp Leu Gln Gln His Leu Arg Phe Gln Val Leu Ala Ala Gly Phe
145                 150                 155                 160

Asn Leu Pro Glu Glu Glu Asn Glu Gly Glu Gly Leu Leu Pro
                165                 170                 175

Gly Ala Leu Gly Gly Pro Leu Gln Met Ser Ala Gln Val Ser Trp Pro
            180                 185                 190

Arg Leu Leu Tyr Thr Tyr Gln Ser Leu His Ser Leu Glu Ile Val Leu
            195                 200                 205

Ser Arg Ala Val Arg Asp Leu Leu Leu Ser Gln Ala Gly Asn Pro
210                 215                 220

Ala Gln Ala Leu Gly Phe Pro Thr Pro Ser Ser Gln Pro
225                 230                 235

<210> SEQ ID NO 15
<211> LENGTH: 252
<212> TYPE: PRT
<213> ORGANISM: Gorilla gorilla

<400> SEQUENCE: 15

Met Lys Asp Arg Pro Glu Asp Gly Pro Tyr Pro Gln Val Leu Ala Gly
  1               5                  10                  15

Thr Asn Arg Leu Ser Leu Leu Leu Pro Leu Leu Leu Val Gln Ala
             20                  25                  30

Gly Val Trp Gly Phe Pro Arg Pro Pro Gly Arg Pro Gln Leu Ser Leu
             35                  40                  45

Gln Glu Leu Arg Arg Glu Phe Thr Val Ser Leu His Leu Ala Arg Lys
 50                  55                  60

Leu Leu Ser Glu Val Arg Gly Gln Ala His Arg Phe Ala Glu Ser His
 65                  70                  75                  80

Leu Pro Gly Val Asn Leu Tyr Leu Leu Pro Leu Gly Glu Gln Leu Pro
                 85                  90                  95

Asp Val Ser Leu Thr Phe Gln Ala Trp Arg Arg Leu Ser Asp Pro Glu
            100                 105                 110

Arg Leu Cys Phe Ile Ser Thr Thr Leu Gln Pro Phe His Ala Leu Leu
            115                 120                 125

Gly Gly Leu Gly Thr Gln Gly Arg Trp Thr Asn Met Glu Arg Met Gln
    130                 135                 140

Leu Trp Ala Met Arg Leu Asp Leu Arg Asp Leu Gln Arg His Leu Arg
145                 150                 155                 160

Phe Gln Val Leu Ala Ala Gly Phe Asn Leu Pro Glu Glu Glu Glu
                165                 170                 175

Glu Glu Glu Glu Glu Glu Glu Glu Arg Lys Gly Leu Leu Pro Gly
            180                 185                 190

Ala Leu Gly Ser Ala Leu Gln Gly Pro Ala Gln Val Ser Trp Pro Gln
    195                 200                 205
```

Leu Leu Ser Thr Tyr Arg Leu Leu His Ser Leu Glu Leu Val Leu Ser
    210                 215                 220

Arg Ala Val Arg Glu Leu Leu Leu Ser Gln Ala Gly His Ser Val
225                 230                 235                 240

Trp Pro Leu Gly Phe Pro Thr Ser Ser Pro Gln Pro
                245                 250

<210> SEQ ID NO 16
<211> LENGTH: 234
<212> TYPE: PRT
<213> ORGANISM: Critesion californicum

<400> SEQUENCE: 16

Met Gly Gln Val Thr Gly Gly Leu Gly Trp Arg Leu Ser Leu Leu Leu
1               5                   10                  15

Leu Pro Leu Leu Leu Val Gln Ala Gly Ala Trp Gly Phe Pro Thr Gly
                20                  25                  30

Pro Leu Ser Leu Gln Glu Leu Arg Arg Glu Phe Thr Val Ser Leu Tyr
                35                  40                  45

Leu Ala Arg Lys Leu Leu Ser Glu Ala Gln Gly Tyr Val His Ser Phe
    50                  55                  60

Ala Glu Ser Arg Leu Pro Gly Val Asn Leu Asp Leu Leu Pro Leu Gly
65                  70                  75                  80

His His Leu Pro Asn Val Ser Leu Thr Phe Gln Ala Trp Arg His Leu
                85                  90                  95

Ser Asp Pro Glu Arg Leu Cys Phe Leu Ser Thr Thr Leu Arg Pro Phe
                100                 105                 110

Pro Ala Leu Leu Glu Gly Leu Gly Asn Gln Gly Thr Trp Thr Ser Ser
                115                 120                 125

Glu Arg Gly Gln Leu Trp Ala Met Arg Leu Asp Leu Arg Asp Leu His
    130                 135                 140

Arg His Phe Arg Phe Gln Val Leu Ala Ala Gly Phe Asn Cys Ser Ala
145                 150                 155                 160

Glu Glu Glu Glu Glu Glu Glu Glu Glu Glu Glu Glu Glu Gly Lys
                165                 170                 175

Glu Leu Leu Leu Gly Ala Leu Asp Gly Pro Lys Gln Val Ser Ser Gln
                180                 185                 190

Val Ser Trp Pro Gln Leu Leu Tyr Thr Tyr Gln Leu Leu His Ser Leu
    195                 200                 205

Glu Leu Val Leu Ser Arg Ala Val Arg Asp Leu Leu Leu Leu Thr Met
    210                 215                 220

Ser Pro His Pro Asp Pro Ala Leu Gly Ser
225                 230

<210> SEQ ID NO 17
<211> LENGTH: 237
<212> TYPE: PRT
<213> ORGANISM: Equus caballus

<400> SEQUENCE: 17

Met Gly Gln Thr Ala Gly Asp Leu Gly Trp Arg Leu Ser Leu Leu Leu
1               5                   10                  15

Leu Ser Leu Leu Leu Ala Arg Ala Gly Val Trp Gly Phe Pro Arg Pro
                20                  25                  30

Pro Gly Arg Ser Pro Leu Ser Leu Gln Glu Leu Gln Arg Glu Phe Lys
                35                  40                  45

Val Ser Leu His Leu Ala Arg Lys Leu Leu Ser Glu Val Arg Ala Gln
 50                  55                  60

Ala His Arg Phe Ala Glu Ser His Leu Pro Gly Val Ser Leu Asp Leu
 65                  70                  75                  80

Leu Pro Leu Gly Asp Gln Leu Pro Asn Val Ser Met Thr Phe Gln Ala
                 85                  90                  95

Trp Arg Ser Leu Ser Asp Pro Glu Arg Leu Cys Phe Leu Ser Met Thr
            100                 105                 110

Leu Arg Pro Phe His Ala Leu Leu Gly Gly Leu Gly Ser Gln Gly Gly
        115                 120                 125

Trp Thr Ser Ser Glu Arg Met Gln Leu Trp Ala Met Arg Leu Asp Leu
130                 135                 140

Arg Asp Leu Gln Arg His Leu His Phe Gln Val Leu Ala Ala Gly Phe
145                 150                 155                 160

Asn Leu Pro Glu Glu Glu Asn Glu Lys Gly Lys Glu Leu Leu Thr
                165                 170                 175

Gly Ala Pro Gly Ser Pro Ser Gln Thr Ser Val Gln Val Ser Trp Pro
            180                 185                 190

Gln Leu Leu Tyr Thr Tyr Gln Leu Leu His Ser Leu Glu Leu Val Leu
        195                 200                 205

Ser Arg Ala Val Arg Asp Leu Leu Leu Ser Gln Ala Gly Asn Pro
210                 215                 220

Ala Gln Ala Leu Gly Cys Pro Thr Pro Ser Ser Gln Pro
225                 230                 235

<210> SEQ ID NO 18
<211> LENGTH: 243
<212> TYPE: PRT
<213> ORGANISM: Macaca mulatta

<400> SEQUENCE: 18

Met Gly Gln Thr Ala Gly Asn Leu Gly Trp Arg Leu Ser Leu Leu Leu
1               5                   10                  15

Leu Pro Leu Leu Leu Val Gln Ala Gly Val Trp Gly Phe Pro Arg Pro
            20                  25                  30

Pro Gly Arg Pro Gln Leu Ser Val Gln Lys Leu Gln Arg Glu Phe Thr
        35                  40                  45

Val Ser Leu His Leu Ala Arg Lys Leu Leu Ser Glu Val Arg Gly Gln
 50                  55                  60

Ala His Arg Phe Ala Glu Ser His Leu Pro Gly Val Asn Leu Asp Leu
 65                  70                  75                  80

Leu Pro Leu Gly Glu Gln Phe Pro Asp Val Ser Leu Thr Phe Gln Thr
                 85                  90                  95

Trp Arg Arg Leu Ser Asp Leu Glu Arg Leu Cys Phe Leu Ser Thr Thr
            100                 105                 110

Leu Gln Pro Phe Arg Ala Leu Leu Gly Gly Leu Gly Thr Gln Gly Arg
        115                 120                 125

Trp Thr Asn Thr Glu Arg Met Gln Leu Trp Ala Met Arg Leu Asp Leu
130                 135                 140

Arg Asp Leu Gln Arg His Leu Arg Phe Gln Val Leu Ala Ala Gly Phe
145                 150                 155                 160

His Leu Pro Glu Glu Glu Glu Glu Glu Glu Glu Glu Glu Glu Glu Glu
                165                 170                 175

Arg Lys Gly Leu Leu Pro Gly Ala Leu Gly Asn Ala Ser Gln Gly Pro
            180                 185                 190

```
Ala Gln Val Ser Trp Pro Gln Leu Leu Ser Thr Tyr Arg Leu Leu His
            195                 200                 205

Ser Leu Glu Leu Val Leu Ser Arg Ala Val Arg Asp Leu Leu Leu Leu
210                 215                 220

Ser Lys Ala Gly His Ser Val Trp Pro Leu Gly Phe Pro Thr Leu Gly
225                 230                 235                 240

Pro Gln Pro
```

<210> SEQ ID NO 19
<211> LENGTH: 238
<212> TYPE: PRT
<213> ORGANISM: Sus scrofa

<400> SEQUENCE: 19

```
Met Gly Gln Met Ala Asp Asp Leu Gly Trp Arg Leu Ser Leu Leu Leu
1               5                   10                  15

Leu Ser Leu Leu Leu Ala Arg Ala Gly Val Trp Gly Phe Pro Arg Pro
                20                  25                  30

Pro Gly Arg Pro Pro Leu Ser Leu Gln Glu Leu Gln Arg Glu Phe Lys
            35                  40                  45

Val Ser Leu His Leu Ala Arg Lys Leu Leu Ser Glu Val Arg Val Gln
50                  55                  60

Ala Arg His Phe Ala Glu Ser His Leu Pro Gly Val Asn Leu Asp Leu
65                  70                  75                  80

Leu Pro Leu Gly Glu Gln Leu Pro Asn Val Ser Leu Asn Phe Gln Ala
                85                  90                  95

Trp Arg Gly Leu Ser Asp Pro Glu Arg Leu Cys Phe Leu Ser Met Thr
            100                 105                 110

Leu Arg Pro Phe His Thr Leu Leu Gly Gly Leu Gly Ser Gln Gly Phe
        115                 120                 125

Trp Thr Ser Ser Glu Arg Met Gln Trp Ala Ile Arg Leu Asp Leu Arg
130                 135                 140

Asp Leu Gln Gln His Leu Arg Phe Gln Val Leu Ala Ala Gly Phe Asn
145                 150                 155                 160

Leu Pro Gly Gln Glu Glu Glu Glu Asn Glu Ala Gly Arg Glu Leu Leu
                165                 170                 175

Pro Gly Ala Pro Gly Pro Ser Lys Pro Ala Ala Gln Val Ser Trp Pro
            180                 185                 190

Pro Arg Leu Leu Tyr Thr Tyr Gln Leu Leu His Ser Leu Glu Leu Val
        195                 200                 205

Leu Ser Arg Ala Met Arg Asp Phe Leu Leu Ser Arg Ala Gly Asn
210                 215                 220

Pro Ala Pro Ala Leu Gly Phe Pro Thr Pro Ser Ser Pro Pro
225                 230                 235
```

<210> SEQ ID NO 20
<211> LENGTH: 218
<212> TYPE: PRT
<213> ORGANISM: Oryctolagus cuniculus

<400> SEQUENCE: 20

```
Met Gly Gln Thr Ala Gly Asn Leu Gly Trp Arg Leu Ser Leu Leu Leu
1               5                   10                  15

Leu Ser Leu Leu Leu Val Arg Ala Gly Val Trp Gly Phe Pro Arg Pro
                20                  25                  30
```

```
Pro Gln Ser Pro Gln Glu Leu Arg Arg Glu Phe Thr Val Ser Leu His
         35                  40                  45

Leu Ala Arg Lys Leu Leu Ser Glu Val Arg Gly Gln Ala His Arg Phe
 50                  55                  60

Ala Glu Ala His Leu Pro Gly Val Asn Leu Asp Leu Leu Pro Leu Gly
 65                  70                  75                  80

Glu Gln Phe Pro Asn Val Ser Leu Thr Phe Gln Val Trp Arg Gln Leu
                 85                  90                  95

Ser Asp Ser Glu Arg Leu Cys Phe Leu Ser Ala Ala Leu Arg Pro Phe
             100                 105                 110

Arg Gly Leu Leu Gly Glu Leu Gly Thr Ser Gln Pro Gly His Cys Leu
         115                 120                 125

Thr Pro Gly Leu Leu Leu Gln Val Leu Ala Ala Gly Cys Asp Leu Pro
130                 135                 140

Glu Gln Glu Glu Arg Glu Glu Gly Lys Gly Leu Leu Pro Gly Ala Pro
145                 150                 155                 160

Gly Gly Pro Ser Pro Ala Trp Ala Gln Leu Ser Trp Pro Gln Leu Leu
                165                 170                 175

Tyr Asn Tyr Gln Leu Leu His Ser Leu Glu Leu Val Leu Ser Arg Ala
            180                 185                 190

Val Arg Asp Leu Leu Leu Ser Lys Ala Gly His Pro Val Gln Ala
        195                 200                 205

Leu Gly Leu Pro Thr Thr Gln Pro Gln Pro
    210                 215

<210> SEQ ID NO 21
<211> LENGTH: 234
<212> TYPE: PRT
<213> ORGANISM: Rattus norvegicus

<400> SEQUENCE: 21

Met Gly Gln Val Thr Gly Gly Leu Gly Trp Arg Leu Ser Leu Leu Leu
 1               5                  10                  15

Leu Pro Leu Leu Met Val Gln Thr Gly Ser Trp Gly Phe Pro Ala Asp
             20                  25                  30

Pro Leu Ser Leu Gln Glu Leu Arg Arg Glu Phe Thr Val Ser Leu Tyr
         35                  40                  45

Leu Ala Arg Lys Leu Leu Ser Glu Val Gln Gly Tyr Val His Ser Phe
 50                  55                  60

Ala Glu Ser Arg Leu Pro Gly Val Asn Leu Asp Leu Leu Pro Val Gly
 65                  70                  75                  80

His His Leu Pro Asn Val Ser Leu Thr Phe Gln Ala Trp Arg His Leu
                 85                  90                  95

Ser Asp Ser Asp Arg Leu Cys Phe Leu Ala Thr Thr Leu Arg Pro Phe
             100                 105                 110

Pro Ala Leu Leu Gly Gly Leu Glu Thr Gln Arg Thr Trp Thr Ser Ser
         115                 120                 125

Glu Arg Glu Gln Leu Trp Ala Met Arg Leu Asp Leu Arg Asp Leu His
130                 135                 140

Arg His Leu Arg Phe Gln Val Leu Ala Val Gly Phe Ser Cys Ser Glu
145                 150                 155                 160

Glu Glu Lys Glu Glu Glu Glu Asp Glu Glu Glu Glu Gly Lys
                165                 170                 175

Glu Leu Leu Leu Gly Ala Leu Gly Gly Pro Asn Gln Val Ser Ser Gln
            180                 185                 190
```

Val Ser Trp Pro Gln Leu Leu Tyr Ala Tyr Gln Leu His Ser Leu
        195                 200                 205

Glu Leu Val Leu Ser Arg Ala Val Arg Asp Leu Leu Leu Ser Leu
    210                 215                 220

Pro Arg Arg Pro Asp Ser Ala Cys Asp Pro
225                 230

<210> SEQ ID NO 22
<211> LENGTH: 197
<212> TYPE: PRT
<213> ORGANISM: Callorhinus ursinus

<400> SEQUENCE: 22

Met Ala Val Phe Phe Leu Leu Leu Ser Leu Thr Glu Leu Val Leu
1               5                   10                  15

Ser Ala Pro Thr Asp Pro Asn Ala Leu Asn Leu Ser Phe His Gln Ser
            20                  25                  30

Leu Asn Leu Ser Arg Lys Ile Leu Gln Asp Val Gln His Leu Leu Leu
        35                  40                  45

Lys Tyr Lys Gln Glu Lys Ile Gly Asn Pro Ser Phe Glu Asp Tyr Asn
    50                  55                  60

Leu Met Leu Gly Ser Leu Pro Ser Cys Gln Val Asp Tyr Arg Ser Trp
65                  70                  75                  80

Leu Glu Gln Gln Asp Glu Glu Arg Leu Leu Asn Cys Arg Asp Leu
                85                  90                  95

Gln Val Phe Trp Met His Val Asp Thr Lys Arg Val His Glu Leu Gly
                100                 105                 110

Gln Ser Gln Asp Ser Ala Leu Leu Glu Ser Met Glu Ala Ile Ser Leu
            115                 120                 125

Asp Leu Arg Asp Leu Ile Ser Gln Leu Asn Ser Gln Ile Ser Ala Leu
        130                 135                 140

Asn Gly Ser Ser Pro Asp Thr Ser Thr Leu Thr Leu Pro Asn Asp Val
145                 150                 155                 160

Leu Asn Pro Leu Tyr Asp Trp His Ser Arg Leu Gln Gly Tyr Ile Ile
                165                 170                 175

Phe Arg Asp Leu Glu Val Tyr Leu Asn Lys Val Val Arg Asp Phe Thr
            180                 185                 190

Val Leu Lys Lys His
        195

<210> SEQ ID NO 23
<211> LENGTH: 199
<212> TYPE: PRT
<213> ORGANISM: Alligator mississippiensis

<400> SEQUENCE: 23

Met Arg Thr Leu Gly Leu Ala Val Val Leu Ser Ala Leu Leu Gly Ala
1               5                   10                  15

Gly Gly Ser Arg Pro Pro Pro Pro Arg Trp Ala Leu Gly Leu Gly
            20                  25                  30

Pro Glu Phe Arg Ser Ser Trp Lys Leu Ala Gln Lys Leu Leu Val Glu
        35                  40                  45

Thr Arg Glu Leu Thr Arg Asp Phe Val Leu Arg His Leu Pro Gly Val
    50                  55                  60

Gln Leu Gln Leu Leu Pro Leu Ser Glu Gln Leu Leu Pro Gly Ser Leu
65                  70                  75                  80

```
Arg Thr Arg Asp Trp Leu Gly Leu Thr Val Leu Ala Arg Leu Gln Gly
                85                  90                  95

Leu Gly Ala Ala Leu Pro Gln Tyr Arg Gly Ala Leu Ala Arg Leu Gly
            100                 105                 110

Leu Pro Gly Gly Asp Pro Glu Phe Ala Gln Arg Leu Gln Asp Val Asp
            115                 120                 125

Trp Asp Leu Arg Asp Leu Ala His His Val Ala Tyr Gln Leu Ser Val
130                 135                 140

Ala Arg Ala Pro Ala Ala Pro Pro Pro Arg Pro Pro Pro Ala Pro
145                 150                 155                 160

Arg Ala Val Trp Arg Arg Leu Gln Ala Thr Ala Val Thr Leu Arg Ser
                165                 170                 175

Leu Glu Ala Val Leu Ala Arg Ala Arg Asp Phe Ala Leu Leu Arg
            180                 185                 190

Arg Leu Val Pro Ala Pro Leu
            195

<210> SEQ ID NO 24
<211> LENGTH: 243
<212> TYPE: PRT
<213> ORGANISM: Homo sapiens
<220> FEATURE:
<221> NAME/KEY: MISC_FEATURE
<222> LOCATION: (164)..(176)
<223> OTHER INFORMATION: deleted amino acids

<400> SEQUENCE: 24

Met Gly Gln Thr Ala Gly Asp Leu Gly Trp Arg Leu Ser Leu Leu Leu
1               5                   10                  15

Leu Pro Leu Leu Leu Val Gln Ala Gly Val Trp Gly Phe Pro Arg Pro
            20                  25                  30

Pro Gly Arg Pro Gln Leu Ser Leu Gln Glu Leu Arg Arg Glu Phe Thr
        35                  40                  45

Val Ser Leu His Leu Ala Arg Lys Leu Leu Ser Glu Val Arg Gly Gln
    50                  55                  60

Ala His Arg Phe Ala Glu Ser His Leu Pro Gly Val Asn Leu Tyr Leu
65                  70                  75                  80

Leu Pro Leu Gly Glu Gln Leu Pro Asp Val Ser Leu Thr Phe Gln Ala
                85                  90                  95

Trp Arg Arg Leu Ser Asp Pro Glu Arg Leu Cys Phe Ile Ser Thr Thr
            100                 105                 110

Leu Gln Pro Phe His Ala Leu Leu Gly Gly Leu Gly Thr Gln Gly Arg
        115                 120                 125

Trp Thr Asn Met Glu Arg Met Gln Leu Trp Ala Met Arg Leu Asp Leu
130                 135                 140

Arg Asp Leu Gln Arg His Leu Arg Phe Gln Val Leu Ala Ala Gly Phe
145                 150                 155                 160

Asn Leu Pro Xaa Xaa Xaa Xaa Xaa Xaa Xaa Xaa Xaa Xaa Xaa Xaa Xaa
                165                 170                 175

Arg Lys Gly Leu Leu Pro Gly Ala Leu Gly Ser Ala Leu Gln Gly Pro
            180                 185                 190

Ala Gln Val Ser Trp Pro Gln Leu Leu Ser Thr Tyr Arg Leu Leu His
        195                 200                 205

Ser Leu Glu Leu Val Leu Ser Arg Ala Val Arg Glu Leu Leu Leu Leu
210                 215                 220
```

```
Ser Lys Ala Gly His Ser Val Trp Pro Leu Gly Phe Pro Thr Leu Ser
225                 230                 235                 240

Pro Gln Pro

<210> SEQ ID NO 25
<211> LENGTH: 243
<212> TYPE: PRT
<213> ORGANISM: Homo sapiens
<220> FEATURE:
<221> NAME/KEY: MISC_FEATURE
<222> LOCATION: (164)..(180)
<223> OTHER INFORMATION: deleted amino acids

<400> SEQUENCE: 25

Met Gly Gln Thr Ala Gly Asp Leu Gly Trp Arg Leu Ser Leu Leu Leu
1               5                   10                  15

Leu Pro Leu Leu Leu Val Gln Ala Gly Val Trp Gly Phe Pro Arg Pro
            20                  25                  30

Pro Gly Arg Pro Gln Leu Ser Leu Gln Glu Leu Arg Arg Glu Phe Thr
        35                  40                  45

Val Ser Leu His Leu Ala Arg Lys Leu Leu Ser Glu Val Arg Gly Gln
50                  55                  60

Ala His Arg Phe Ala Glu Ser His Leu Pro Gly Val Asn Leu Tyr Leu
65                  70                  75                  80

Leu Pro Leu Gly Glu Gln Leu Pro Asp Val Ser Leu Thr Phe Gln Ala
            85                  90                  95

Trp Arg Arg Leu Ser Asp Pro Glu Arg Leu Cys Phe Ile Ser Thr Thr
        100                 105                 110

Leu Gln Pro Phe His Ala Leu Leu Gly Gly Leu Gly Thr Gln Gly Arg
    115                 120                 125

Trp Thr Asn Met Glu Arg Met Gln Leu Trp Ala Met Arg Leu Asp Leu
130                 135                 140

Arg Asp Leu Gln Arg His Leu Arg Phe Gln Val Leu Ala Ala Gly Phe
145                 150                 155                 160

Asn Leu Pro Xaa Xaa Xaa Xaa Xaa Xaa Xaa Xaa Xaa Xaa Xaa Xaa Xaa
            165                 170                 175

Xaa Xaa Xaa Xaa Leu Pro Gly Ala Leu Gly Ser Ala Leu Gln Gly Pro
        180                 185                 190

Ala Gln Val Ser Trp Pro Gln Leu Leu Ser Thr Tyr Arg Leu Leu His
    195                 200                 205

Ser Leu Glu Leu Val Leu Ser Arg Ala Val Arg Glu Leu Leu Leu Leu
    210                 215                 220

Ser Lys Ala Gly His Ser Val Trp Pro Leu Gly Phe Pro Thr Leu Ser
225                 230                 235                 240

Pro Gln Pro

<210> SEQ ID NO 26
<211> LENGTH: 243
<212> TYPE: PRT
<213> ORGANISM: Homo sapiens
<220> FEATURE:
<221> NAME/KEY: MISC_FEATURE
<222> LOCATION: (164)..(180)
<223> OTHER INFORMATION: amino acid deletion, replacement by GS
```

<400> SEQUENCE: 26

```
Met Gly Gln Thr Ala Gly Asp Leu Gly Trp Arg Leu Ser Leu Leu Leu
1               5                   10                  15

Leu Pro Leu Leu Leu Val Gln Ala Gly Val Trp Gly Phe Pro Arg Pro
            20                  25                  30

Pro Gly Arg Pro Gln Leu Ser Leu Gln Glu Leu Arg Arg Glu Phe Thr
        35                  40                  45

Val Ser Leu His Leu Ala Arg Lys Leu Leu Ser Glu Val Arg Gly Gln
    50                  55                  60

Ala His Arg Phe Ala Glu Ser His Leu Pro Gly Val Asn Leu Tyr Leu
65                  70                  75                  80

Leu Pro Leu Gly Glu Gln Leu Pro Asp Val Ser Leu Thr Phe Gln Ala
                85                  90                  95

Trp Arg Arg Leu Ser Asp Pro Glu Arg Leu Cys Phe Ile Ser Thr Thr
            100                 105                 110

Leu Gln Pro Phe His Ala Leu Leu Gly Gly Leu Gly Thr Gln Gly Arg
        115                 120                 125

Trp Thr Asn Met Glu Arg Met Gln Leu Trp Ala Met Arg Leu Asp Leu
    130                 135                 140

Arg Asp Leu Gln Arg His Leu Arg Phe Gln Val Leu Ala Ala Gly Phe
145                 150                 155                 160

Asn Leu Pro Xaa Xaa Xaa Xaa Xaa Xaa Xaa Xaa Xaa Xaa Xaa Xaa Xaa
                165                 170                 175

Xaa Xaa Gly Ser Leu Pro Gly Ala Leu Gly Ser Ala Leu Gln Gly Pro
            180                 185                 190

Ala Gln Val Ser Trp Pro Gln Leu Leu Ser Thr Tyr Arg Leu Leu His
        195                 200                 205

Ser Leu Glu Leu Val Leu Ser Arg Ala Val Arg Glu Leu Leu Leu Leu
    210                 215                 220

Ser Lys Ala Gly His Ser Val Trp Pro Leu Gly Phe Pro Thr Leu Ser
225                 230                 235                 240

Pro Gln Pro
```

<210> SEQ ID NO 27
<211> LENGTH: 233
<212> TYPE: PRT
<213> ORGANISM: artificial sequence
<220> FEATURE:
<223> OTHER INFORMATION: humanEbi3 with KDEL at C-Terminus

<400> SEQUENCE: 27

```
Met Thr Pro Gln Leu Leu Leu Ala Leu Val Leu Trp Ala Ser Cys Pro
1               5                   10                  15

Pro Cys Ser Gly Arg Lys Gly Pro Pro Ala Ala Leu Thr Leu Pro Arg
            20                  25                  30

Val Gln Cys Arg Ala Ser Arg Tyr Pro Ile Ala Val Asp Cys Ser Trp
        35                  40                  45

Thr Leu Pro Pro Ala Pro Asn Ser Thr Ser Pro Val Ser Phe Ile Ala
    50                  55                  60

Thr Tyr Arg Leu Gly Met Ala Ala Arg Gly His Ser Trp Pro Cys Leu
65                  70                  75                  80

Gln Gln Thr Pro Thr Ser Thr Ser Cys Thr Ile Thr Asp Val Gln Leu
                85                  90                  95

Phe Ser Met Ala Pro Tyr Val Leu Asn Val Thr Ala Val His Pro Trp
            100                 105                 110
```

```
Gly Ser Ser Ser Ser Phe Val Pro Phe Ile Thr Glu His Ile Ile Lys
            115                 120                 125

Pro Asp Pro Pro Glu Gly Val Arg Leu Ser Pro Leu Ala Glu Arg Gln
    130                 135                 140

Leu Gln Val Gln Trp Glu Pro Pro Gly Ser Trp Pro Phe Pro Glu Ile
145                 150                 155                 160

Phe Ser Leu Lys Tyr Trp Ile Arg Tyr Lys Arg Gln Gly Ala Ala Arg
                165                 170                 175

Phe His Arg Val Gly Pro Ile Glu Ala Thr Ser Phe Ile Leu Arg Ala
                180                 185                 190

Val Arg Pro Arg Ala Arg Tyr Tyr Val Gln Val Ala Ala Gln Asp Leu
                195                 200                 205

Thr Asp Tyr Gly Glu Leu Ser Asp Trp Ser Leu Pro Ala Thr Ala Thr
                210                 215                 220

Met Ser Leu Gly Lys Lys Asp Glu Leu
225                 230
```

<210> SEQ ID NO 28
<211> LENGTH: 243
<212> TYPE: PRT
<213> ORGANISM: artificial sequence
<220> FEATURE:
<223> OTHER INFORMATION: human IL27 alpha C107L

<400> SEQUENCE: 28

```
Met Gly Gln Thr Ala Gly Asp Leu Gly Trp Arg Leu Ser Leu Leu Leu
1               5                   10                  15

Leu Pro Leu Leu Leu Val Gln Ala Gly Val Trp Gly Phe Pro Arg Pro
                20                  25                  30

Pro Gly Arg Pro Gln Leu Ser Leu Gln Glu Leu Arg Arg Glu Phe Thr
            35                  40                  45

Val Ser Leu His Leu Ala Arg Lys Leu Leu Ser Glu Val Arg Gly Gln
    50                  55                  60

Ala His Arg Phe Ala Glu Ser His Leu Pro Gly Val Asn Leu Tyr Leu
65                  70                  75                  80

Leu Pro Leu Gly Glu Gln Leu Pro Asp Val Ser Leu Thr Phe Gln Ala
                85                  90                  95

Trp Arg Arg Leu Ser Asp Pro Glu Arg Leu Leu Phe Ile Ser Thr Thr
                100                 105                 110

Leu Gln Pro Phe His Ala Leu Leu Gly Gly Leu Gly Thr Gln Gly Arg
            115                 120                 125

Trp Thr Asn Met Glu Arg Met Gln Leu Trp Ala Met Arg Leu Asp Leu
    130                 135                 140

Arg Asp Leu Gln Arg His Leu Arg Phe Gln Val Leu Ala Ala Gly Phe
145                 150                 155                 160

Asn Leu Pro Glu Glu Glu Glu Glu Glu Glu Glu Glu Glu Glu Glu Glu
                165                 170                 175

Arg Lys Gly Leu Leu Pro Gly Ala Leu Gly Ser Ala Leu Gln Gly Pro
                180                 185                 190

Ala Gln Val Ser Trp Pro Gln Leu Leu Ser Thr Tyr Arg Leu Leu His
            195                 200                 205

Ser Leu Glu Leu Val Leu Ser Arg Ala Val Arg Glu Leu Leu Leu Leu
    210                 215                 220
```

Ser Lys Ala Gly His Ser Val Trp Pro Leu Gly Phe Pro Thr Leu Ser
225                 230                 235                 240

Pro Gln Pro

<210> SEQ ID NO 29
<211> LENGTH: 234
<212> TYPE: PRT
<213> ORGANISM: artificial sequence
<220> FEATURE:
<223> OTHER INFORMATION: mouse IL27 alpha C158L

<400> SEQUENCE: 29

Met Gly Gln Val Thr Gly Asp Leu Gly Trp Arg Leu Ser Leu Leu Leu
1               5                   10                  15

Leu Pro Leu Leu Leu Val Gln Ala Gly Ser Trp Gly Phe Pro Thr Asp
                20                  25                  30

Pro Leu Ser Leu Gln Glu Leu Arg Arg Glu Phe Thr Val Ser Leu Tyr
            35                  40                  45

Leu Ala Arg Lys Leu Leu Ser Glu Val Gln Gly Tyr Val His Ser Phe
    50                  55                  60

Ala Glu Ser Arg Leu Pro Gly Val Asn Leu Asp Leu Leu Pro Leu Gly
65                  70                  75                  80

Tyr His Leu Pro Asn Val Ser Leu Thr Phe Gln Ala Trp His His Leu
                85                  90                  95

Ser Asp Ser Glu Arg Leu Cys Phe Leu Ala Thr Thr Leu Arg Pro Phe
            100                 105                 110

Pro Ala Met Leu Gly Gly Leu Gly Thr Gln Gly Thr Trp Thr Ser Ser
        115                 120                 125

Glu Arg Glu Gln Leu Trp Ala Met Arg Leu Asp Leu Arg Asp Leu His
130                 135                 140

Arg His Leu Arg Phe Gln Val Leu Ala Ala Gly Phe Lys Leu Ser Lys
145                 150                 155                 160

Glu Glu Glu Asp Lys Glu Glu Glu Glu Glu Glu Glu Glu Glu Glu Lys
                165                 170                 175

Lys Leu Pro Leu Gly Ala Leu Gly Gly Pro Asn Gln Val Ser Ser Gln
            180                 185                 190

Val Ser Trp Pro Gln Leu Leu Tyr Thr Tyr Gln Leu Leu His Ser Leu
        195                 200                 205

Glu Leu Val Leu Ser Arg Ala Val Arg Asp Leu Leu Leu Leu Ser Leu
    210                 215                 220

Pro Arg Arg Pro Gly Ser Ala Trp Asp Ser
225                 230

<210> SEQ ID NO 30
<211> LENGTH: 228
<212> TYPE: PRT
<213> ORGANISM: Mus musculus

<400> SEQUENCE: 30

Met Ser Lys Leu Leu Phe Leu Ser Leu Ala Leu Trp Ala Ser Arg Ser
1               5                   10                  15

Pro Gly Tyr Thr Glu Thr Ala Leu Val Ala Leu Ser Gln Pro Arg Val
                20                  25                  30

Gln Cys His Ala Ser Arg Tyr Pro Val Ala Val Asp Cys Ser Trp Thr
            35                  40                  45

Pro Leu Gln Ala Pro Asn Ser Thr Arg Ser Thr Ser Phe Ile Ala Thr
    50                  55                  60

Tyr Arg Leu Gly Val Ala Thr Gln Gln Ser Gln Pro Cys Leu Gln
65                  70                  75                  80

Arg Ser Pro Gln Ala Ser Arg Cys Thr Ile Pro Asp Val His Leu Phe
            85                  90                  95

Ser Thr Val Pro Tyr Met Leu Asn Val Thr Ala Val His Pro Gly Gly
            100                 105                 110

Ala Ser Ser Ser Leu Leu Ala Phe Val Ala Glu Arg Ile Ile Lys Pro
            115                 120                 125

Asp Pro Pro Glu Gly Val Arg Leu Arg Thr Ala Gly Gln Arg Leu Gln
        130                 135                 140

Val Leu Trp His Pro Pro Ala Ser Trp Pro Phe Pro Asp Ile Phe Ser
145                 150                 155                 160

Leu Lys Tyr Arg Leu Arg Tyr Arg Arg Gly Ala Ser His Phe Arg
                165                 170                 175

Gln Val Gly Pro Ile Glu Ala Thr Thr Phe Thr Leu Arg Asn Ser Lys
            180                 185                 190

Pro His Ala Lys Tyr Cys Ile Gln Val Ser Ala Gln Asp Leu Thr Asp
            195                 200                 205

Tyr Gly Lys Pro Ser Asp Trp Ser Leu Pro Gly Gln Val Glu Ser Ala
        210                 215                 220

Pro His Lys Pro
225

<210> SEQ ID NO 31
<211> LENGTH: 243
<212> TYPE: PRT
<213> ORGANISM: artificial sequence
<220> FEATURE:
<223> OTHER INFORMATION: human Interleukin27 alpha D89N

<400> SEQUENCE: 31

Met Gly Gln Thr Ala Gly Asp Leu Gly Trp Arg Leu Ser Leu Leu Leu
1               5                   10                  15

Leu Pro Leu Leu Leu Val Gln Ala Gly Val Tr

```
Ala Gln Val Ser Trp Pro Gln Leu Leu Ser Thr Tyr Arg Leu Leu His
            195                 200                 205

Ser Leu Glu Leu Val Leu Ser Arg Ala Val Arg Glu Leu Leu Leu
    210                 215                 220

Ser Lys Ala Gly His Ser Val Trp Pro Leu Gly Phe Pro Thr Leu Ser
225                 230                 235                 240

Pro Gln Pro

<210> SEQ ID NO 32
<211> LENGTH: 244
<212> TYPE: PRT
<213> ORGANISM: artificial sequence
<220> FEATURE:
<223> OTHER INFORMATION: human Interleukin27 alpha K168 insertion

<400> SEQUENCE: 32

Met Gly Gln Thr Ala Gly Asp Leu Gly Trp Arg Leu Ser Leu Leu Leu
1               5                   10                  15

Leu Pro Leu Leu Leu Val Gln Ala Gly Val Trp Gly Phe Pro Arg Pro
                20                  25                  30

Pro Gly Arg Pro Gln Leu Ser Leu Gln Glu Leu Arg Arg Glu Phe Thr
            35                  40                  45

Val Ser Leu His Leu Ala Arg Lys Leu Leu Ser Glu Val Arg Gly Gln
    50                  55                  60

Ala His Arg Phe Ala Glu Ser His Leu Pro Gly Val Asn Leu Tyr Leu
65                  70                  75                  80

Leu Pro Leu Gly Glu Gln Leu Pro Asp Val Ser Leu Thr Phe Gln Ala
                85                  90                  95

Trp Arg Arg Leu Ser Asp Pro Glu Arg Leu Cys Phe Ile Ser Thr Thr
            100                 105                 110

Leu Gln Pro Phe His Ala Leu Leu Gly Gly Leu Gly Thr Gln Gly Arg
        115                 120                 125

Trp Thr Asn Met Glu Arg Met Gln Leu Trp Ala Met Arg Leu Asp Leu
130                 135                 140

Arg Asp Leu Gln Arg His Leu Arg Phe Gln Val Leu Ala Ala Gly Phe
145                 150                 155                 160

Asn Leu Pro Glu Glu Glu Lys Glu Glu Glu Glu Glu Glu Glu Glu Glu
                165                 170                 175

Glu Arg Lys Gly Leu Leu Pro Gly Ala Leu Gly Ser Ala Leu Gln Gly
            180                 185                 190

Pro Ala Gln Val Ser Trp Pro Gln Leu Leu Ser Thr Tyr Arg Leu Leu
        195                 200                 205

His Ser Leu Glu Leu Val Leu Ser Arg Ala Val Arg Glu Leu Leu Leu
    210                 215                 220

Leu Ser Lys Ala Gly His Ser Val Trp Pro Leu Gly Phe Pro Thr Leu
225                 230                 235                 240

Ser Pro Gln Pro

<210> SEQ ID NO 33
<211> LENGTH: 243
<212> TYPE: PRT
<213> ORGANISM: artificial sequence
<220> FEATURE:
<223> OTHER INFORMATION: mutein of human Interleukin 27 alpha-subunit
      E164C
```

<400> SEQUENCE: 33

Met Gly Gln Thr Ala Gly Asp Leu Gly Trp Arg Leu Ser Leu Leu Leu
1               5                   10                  15

Leu Pro Leu Leu Leu Val Gln Ala Gly Val Trp Gly Phe Pro Arg Pro
            20                  25                  30

Pro Gly Arg Pro Gln Leu Ser Leu Gln Glu Leu Arg Arg Glu Phe Thr
        35                  40                  45

Val Ser Leu His Leu Ala Arg Lys Leu Leu Ser Glu Val Arg Gly Gln
    50                  55                  60

Ala His Arg Phe Ala Glu Ser His Leu Pro Gly Val Asn Leu Tyr Leu
65                  70                  75                  80

Leu Pro Leu Gly Glu Gln Leu Pro Asp Val Ser Leu Thr Phe Gln Ala
            85                  90                  95

Trp Arg Arg Leu Ser Asp Pro Glu Arg Leu Cys Phe Ile Ser Thr Thr
            100                 105                 110

Leu Gln Pro Phe His Ala Leu Leu Gly Gly Leu Gly Thr Gln Gly Arg
        115                 120                 125

Trp Thr Asn Met Glu Arg Met Gln Leu Trp Ala Met Arg Leu Asp Leu
130                 135                 140

Arg Asp Leu Gln Arg His Leu Arg Phe Gln Val Leu Ala Ala Gly Phe
145                 150                 155                 160

Asn Leu Pro Cys Glu Glu Glu Glu Glu Glu Glu Glu Glu Glu Glu Glu
            165                 170                 175

Arg Lys Gly Leu Leu Pro Gly Ala Leu Gly Ser Ala Leu Gln Gly Pro
        180                 185                 190

Ala Gln Val Ser Trp Pro Gln Leu Leu Ser Thr Tyr Arg Leu Leu His
        195                 200                 205

Ser Leu Glu Leu Val Leu Ser Arg Ala Val Arg Glu Leu Leu Leu Leu
        210                 215                 220

Ser Lys Ala Gly His Ser Val Trp Pro Leu Gly Phe Pro Thr Leu Ser
225                 230                 235                 240

Pro Gln Pro

<210> SEQ ID NO 34
<211> LENGTH: 243
<212> TYPE: PRT
<213> ORGANISM: artificial sequence
<220> FEATURE:
<223> OTHER INFORMATION: mutein of human Interleukin 27 alpha-subunit E165C

<400> SEQUENCE: 34

Met Gly Gln Thr Ala Gly Asp Leu Gly Trp Arg Leu Ser Leu Leu Leu
1               5                   10                  15

Leu Pro Leu Leu Leu Val Gln Ala Gly Val Trp Gly Phe Pro Arg Pro
            20                  25                  30

Pro Gly Arg Pro Gln Leu Ser Leu Gln Glu Leu Arg Arg Glu Phe Thr
        35                  40                  45

Val Ser Leu His Leu Ala Arg Lys Leu Leu Ser Glu Val Arg Gly Gln
    50                  55                  60

Ala His Arg Phe Ala Glu Ser His Leu Pro Gly Val Asn Leu Tyr Leu
65                  70                  75                  80

Leu Pro Leu Gly Glu Gln Leu Pro Asp Val Ser Leu Thr Phe Gln Ala
            85                  90                  95

```
Trp Arg Arg Leu Ser Asp Pro Glu Arg Leu Cys Phe Ile Ser Thr Thr
            100                 105                 110

Leu Gln Pro Phe His Ala Leu Leu Gly Gly Leu Gly Thr Gln Gly Arg
        115                 120                 125

Trp Thr Asn Met Glu Arg Met Gln Leu Trp Ala Met Arg Leu Asp Leu
    130                 135                 140

Arg Asp Leu Gln Arg His Leu Arg Phe Gln Val Leu Ala Ala Gly Phe
145                 150                 155                 160

Asn Leu Pro Glu Cys Glu Glu Glu Glu Glu Glu Glu Glu Glu Glu Glu
                165                 170                 175

Arg Lys Gly Leu Leu Pro Gly Ala Leu Gly Ser Ala Leu Gln Gly Pro
                180                 185                 190

Ala Gln Val Ser Trp Pro Gln Leu Leu Ser Thr Tyr Arg Leu Leu His
        195                 200                 205

Ser Leu Glu Leu Val Leu Ser Arg Ala Val Arg Glu Leu Leu Leu Leu
        210                 215                 220

Ser Lys Ala Gly His Ser Val Trp Pro Leu Gly Phe Pro Thr Leu Ser
225                 230                 235                 240

Pro Gln Pro

<210> SEQ ID NO 35
<211> LENGTH: 228
<212> TYPE: PRT
<213> ORGANISM: Mus musculus

<400> SEQUENCE: 35

Met Ser Lys Leu Leu Phe Leu Ser Leu Ala Leu Trp Ala Ser Arg Ser
1               5                   10                  15

Pro Gly Tyr Thr Glu Thr Ala Leu Val Ala Leu Ser Gln Pro Arg Val
                20                  25                  30

Gln Cys His Ala Ser Arg Tyr Pro Val Ala Val Asp Cys Ser Trp Thr
            35                  40                  45

Pro Leu Gln Ala Pro Asn Ser Thr Arg Ser Thr Ser Phe Ile Ala Thr
        50                  55                  60

Tyr Arg Leu Gly Val Ala Thr Gln Gln Gln Ser Gln Pro Cys Leu Gln
65                  70                  75                  80

Arg Ser Pro Gln Ala Ser Arg Cys Thr Ile Pro Asp Val His Leu Phe
                85                  90                  95

Ser Thr Val Pro Tyr Met Leu Asn Val Thr Ala Val His Pro Gly Gly
                100                 105                 110

Ala Ser Ser Ser Leu Leu Ala Phe Val Ala Glu Arg Ile Ile Lys Pro
        115                 120                 125

Asp Pro Pro Glu Gly Val Arg Leu Arg Thr Ala Gly Gln Arg Leu Gln
        130                 135                 140

Val Leu Trp His Pro Pro Ala Ser Trp Pro Phe Pro Asp Ile Phe Ser
145                 150                 155                 160

Leu Lys Tyr Arg Leu Arg Tyr Arg Arg Gly Ala Ser His Phe Arg
                165                 170                 175

Gln Val Gly Pro Ile Glu Ala Thr Thr Phe Thr Leu Arg Asn Ser Lys
        180                 185                 190

Pro His Ala Lys Tyr Cys Ile Gln Val Ser Ala Gln Asp Leu Thr Asp
        195                 200                 205
```

Tyr Gly Lys Pro Ser Asp Trp Ser Leu Pro Gly Gln Val Glu Ser Ala
    210                 215                 220

Pro His Lys Pro
225

<210> SEQ ID NO 36
<211> LENGTH: 228
<212> TYPE: PRT
<213> ORGANISM: artificial sequence
<220> FEATURE:
<223> OTHER INFORMATION: mutein of murine Interleukin 27 beta-subunit
      C198Y

<400> SEQUENCE: 36

Met Ser Lys Leu Leu Phe Leu Ser Leu Ala Leu Trp Ala Ser Arg Ser
1               5                   10                  15

Pro Gly Tyr Thr Glu Thr Ala Leu Val Ala Leu Ser Gln Pro Arg Val
            20                  25                  30

Gln Cys His Ala Ser Arg Tyr Pro Val Ala Val Asp Cys Ser Trp Thr
        35                  40                  45

Pro Leu Gln Ala Pro Asn Ser Thr Arg Ser Thr Ser Phe Ile Ala Thr
    50                  55                  60

Tyr Arg Leu Gly Val Ala Thr Gln Gln Gln Ser Gln Pro Cys Leu Gln
65                  70                  75                  80

Arg Ser Pro Gln Ala Ser Arg Cys Thr Ile Pro Asp Val His Leu Phe
                85                  90                  95

Ser Thr Val Pro Tyr Met Leu Asn Val Thr Ala Val His Pro Gly Gly
            100                 105                 110

Ala Ser Ser Ser Leu Leu Ala Phe Val Ala Glu Arg Ile Ile Lys Pro
        115                 120                 125

Asp Pro Pro Glu Gly Val Arg Leu Arg Thr Ala Gly Gln Arg Leu Gln
    130                 135                 140

Val Leu Trp His Pro Pro Ala Ser Trp Pro Phe Pro Asp Ile Phe Ser
145                 150                 155                 160

Leu Lys Tyr Arg Leu Arg Tyr Arg Arg Arg Gly Ala Ser His Phe Arg
                165                 170                 175

Gln Val Gly Pro Ile Glu Ala Thr Thr Phe Thr Leu Arg Asn Ser Lys
            180                 185                 190

Pro His Ala Lys Tyr Tyr Ile Gln Val Ser Ala Gln Asp Leu Thr Asp
        195                 200                 205

Tyr Gly Lys Pro Ser Asp Trp Ser Leu Pro Gly Gln Val Glu Ser Ala
    210                 215                 220

Pro His Lys Pro
225

The invention claimed is:

1. A secretion-competent mutein of the human Interleukin 27 α-subunit of SEQ ID NO: 1 in which the amino acid residue at one of sequence positions 160, 161, 162, 163, 164, 165, 180, 181 and 182 according to SEQ ID NO: 1 is substituted by cysteine, wherein the mutein has the activity of the human Interleukin 27 α-subunit.

2. The secretion-competent mutein of the human Interleukin 27 α-subunit of claim 1, wherein the mutein comprises one or more salt bridges, one or more disulfide bridges, or both one or more salt bridges and one or more disulfide bridges.

3. A secretion-competent mutein of human Interleukin 27, comprising an α-subunit p28 and a β-subunit EBI3, wherein the α-subunit p28 is the secretion-competent mutein of the Interleukin 27 α-subunit of claim 1.

4. The secretion-competent mutein of human Interleukin 27 of claim 3, wherein the secretion-competent mutein of human Interleukin 27 comprises one or more salt bridges.

5. The secretion-competent mutein of human Interleukin 27 of claim 3, wherein the secretion-competent mutein of human Interleukin 27 comprises one or more disulfide bridges.

6. A composition comprising the secretion-competent mutein of the human Interleukin 27 α-subunit of claim 1 and a pharmacologically acceptable excipient.

7. A method of treating a disease selected from the group consisting of an infectious disease, an autoimmune disease, cancer, Graft-versus-Host-disease, an inflammatory disease, sepsis, septic shock, and asthma, comprising the step of administering the composition of claim 6 to a subject in need thereof.

8. A nucleic acid molecule comprising a nucleotide sequence encoding the secretion-competent mutein of the human Interleukin 27 α-subunit of claim 1.

9. A vector comprising the nucleic acid molecule of claim 8.

10. A host cell comprising the nucleic acid molecule of claim 8.

11. A method for producing a secretion-competent mutein of the human Interleukin 27 α-subunit, which mutein is encoded by the nucleic acid molecule of claim 8, comprising the steps of: introducing the nucleic acid molecule operably linked to a regulatory sequence for expression of the mutein into a suitable host cell, cell extract or cell lysate, and expressing the mutein under suitable conditions.

12. The method of claim 11, wherein the secretion-competent mutein of the human Interleukin 27 α-subunit comprises the L162C substitution.

13. The nucleic acid molecule according to claim 8, further comprising a nucleotide sequence that encodes a β-subunit EBI3 of human Interleukin 27.

14. A method for producing a secretion-competent mutein of the human Interleukin 27, which mutein is encoded by the nucleic acid molecule of claim 13, comprising the steps of: introducing the nucleic acid molecule operably linked to a regulatory sequence for expression of the mutein into a suitable host cell, cell extract or cell lysate, and expressing the mutein under suitable conditions.

* * * * *